United States Patent
Korb et al.

(12) 
(10) Patent No.: US 8,128,673 B2
(45) Date of Patent: *Mar. 6, 2012

(54) SYSTEM FOR INNER EYELID HEAT AND PRESSURE TREATMENT FOR TREATING MEIBOMIAN GLAND DYSFUNCTION

(75) Inventors: Donald R. Korb, Boston, MA (US); Stephen M. Grenon, Durham, NC (US)

(73) Assignee: TearScience, Inc., Morrisville, NC (US)

( * ) Notice: Subject to any disclaimer, the term of this patent is extended or adjusted under 35 U.S.C. 154(b) by 1015 days.

This patent is subject to a terminal disclaimer.

(21) Appl. No.: 12/015,675

(22) Filed: Jan. 17, 2008

(65) Prior Publication Data

US 2008/0114425 A1 May 15, 2008

Related U.S. Application Data

(63) Continuation-in-part of application No. 11/893,669, filed on Aug. 17, 2007, and a continuation-in-part of application No. 11/541,308, filed on Sep. 29, 2006, and a continuation-in-part of application No. 11/541,418, filed on Sep. 29, 2006, now Pat. No. 7,981,145, and a continuation-in-part of application No. 11/541,291, filed on Sep. 29, 2006, now Pat. No. 7,981,095, and a continuation-in-part of application No. 11/434,054, filed on May 15, 2006, now Pat. No. 8,083,787, and a continuation-in-part of application No. 11/434,446, filed on May 15, 2006, now abandoned, and a continuation-in-part of application No. 11/434,033, filed on May 15, 2006.

(60) Provisional application No. 60/880,850, filed on Jan. 17, 2007.

(51) Int. Cl.
*A61F 7/00* (2006.01)

(52) U.S. Cl. ............................................. 607/96; 607/1

(58) Field of Classification Search ...................... 607/96
See application file for complete search history.

(56) References Cited

U.S. PATENT DOCUMENTS
1,006,945 A 10/1911 Houston
(Continued)

FOREIGN PATENT DOCUMENTS
CA 2679448 A1 9/2008
(Continued)

OTHER PUBLICATIONS
Non-Final Rejection mailed Jun. 17, 2009, for U.S. Appl. No. 11/434,446.
(Continued)

*Primary Examiner* — Linda Dvorak
*Assistant Examiner* — Kaitlyn Smith
(74) *Attorney, Agent, or Firm* — Withrow & Terranova, PLLC

(57) ABSTRACT

A system for treating meibomian gland dysfunction. A controller controls heat applied to the inside of the eyelid to provide conductive heat transfer to the meibomian glands. The application of heat assists in the expression of obstructions or occlusions in the meibomian glands to restore sufficient sebum flow to the lipid layer to treat dry eye. Temperatures at the meibomian glands reach desired levels more quickly and efficiently when heating the inside of the eyelid. Reaching such higher temperature levels may be instrumental in removing obstructions in the meibomian glands. Less time may also be required to reach desired temperature levels when applying heat to the inside of the eyelid. A force may also be applied to the inside of the patient's eyelid to improve conductive heat transfer and reduce blood flow in the eyelid that causes convective heat loss. Thus, the application of force can further increase the temperature level and/or reduce the time to reach desired temperature levels for removing obstructions.

24 Claims, 43 Drawing Sheets

U.S. PATENT DOCUMENTS

| | | |
|---|---|---|
| 1,924,315 A | 8/1933 | Hemphill et al. |
| 2,545,724 A | 3/1951 | Curtis |
| 2,891,252 A | 6/1959 | Lazo |
| 3,333,586 A | 8/1967 | Bellis et al. |
| 3,404,678 A | 10/1968 | Von Ardenne |
| 3,667,476 A | 6/1972 | Muller |
| 4,261,364 A | 4/1981 | Haddad et al. |
| 4,778,457 A | 10/1988 | York |
| 4,883,454 A | 11/1989 | Hamburg |
| 4,914,088 A | 4/1990 | Glonek et al. |
| 4,955,377 A | 9/1990 | Lennox et al. |
| 4,958,632 A | 9/1990 | Duggan |
| 5,030,214 A | 7/1991 | Spector |
| 5,151,100 A | 9/1992 | Abele et al. |
| 5,158,082 A | 10/1992 | Jones |
| 5,213,097 A | 5/1993 | Zeindler |
| 5,251,627 A | 10/1993 | Morris |
| 5,283,063 A | 2/1994 | Freeman |
| 5,314,456 A | 5/1994 | Cohen |
| 5,343,561 A | 9/1994 | Adamo |
| D352,106 S | 11/1994 | Fanney et al. |
| 5,368,582 A | 11/1994 | Bertera |
| 5,368,591 A | 11/1994 | Lennox et al. |
| 5,425,380 A | 6/1995 | Hudson et al. |
| 5,496,311 A | 3/1996 | Abele et al. |
| 5,601,548 A | 2/1997 | Smith et al. |
| 5,643,336 A | 7/1997 | Lopez-Claros |
| 5,700,238 A | 12/1997 | Hyson |
| 5,720,773 A | 2/1998 | Lopez-Claros |
| 5,807,357 A | 9/1998 | Kang |
| 5,836,927 A | 11/1998 | Fried |
| 5,958,912 A | 9/1999 | Sullivan |
| 5,964,723 A | 10/1999 | Augustine |
| 6,024,095 A | 2/2000 | Stanley, III |
| 6,107,289 A | 8/2000 | Sullivan |
| 6,110,292 A | 8/2000 | Jewett et al. |
| 6,112,900 A | 9/2000 | Adkins, Jr. |
| 6,113,561 A | 9/2000 | Augustine |
| 6,153,607 A | 11/2000 | Pflugfelder et al. |
| 6,155,995 A | 12/2000 | Lin |
| 6,181,970 B1 | 1/2001 | Kasevich |
| 6,193,740 B1 | 2/2001 | Rodriguez |
| 6,206,842 B1 | 3/2001 | Tu et al. |
| 6,213,966 B1 | 4/2001 | Augustine |
| 6,273,886 B1 | 8/2001 | Edwards et al. |
| D456,079 S | 4/2002 | Fujii |
| 6,423,018 B1 | 7/2002 | Augustine |
| 6,425,888 B1 | 7/2002 | Embleton et al. |
| 6,438,398 B1 | 8/2002 | Pflugfelder et al. |
| 6,455,583 B1 | 9/2002 | Pflugfelder et al. |
| 6,482,203 B2 | 11/2002 | Paddock et al. |
| 6,490,488 B1 | 12/2002 | Rudie et al. |
| D472,637 S | 4/2003 | Cooper et al. |
| 6,544,257 B2 | 4/2003 | Nagase et al. |
| D477,084 S | 7/2003 | Menezes et al. |
| 6,641,264 B1 | 11/2003 | Schwebel |
| 6,788,977 B2 | 9/2004 | Fenn et al. |
| 6,827,898 B1 | 12/2004 | Fausset et al. |
| 6,840,954 B2 | 1/2005 | Dietz et al. |
| 6,860,852 B2 | 3/2005 | Schonenberger et al. |
| 6,860,880 B2 | 3/2005 | Treat et al. |
| 6,874,884 B2 | 4/2005 | Schwebel |
| 6,882,885 B2 | 4/2005 | Levy, Jr. et al. |
| 6,886,933 B2 | 5/2005 | Schwebel |
| 6,908,195 B2 | 6/2005 | Fuller |
| 6,925,317 B1 | 8/2005 | Samuels et al. |
| 6,974,454 B2 | 12/2005 | Hooven |
| 7,001,379 B2 | 2/2006 | Behl et al. |
| 7,004,942 B2 | 2/2006 | Laird et al. |
| 7,036,928 B2 | 5/2006 | Schwebel |
| 7,069,084 B2 | 6/2006 | Yee |
| 7,108,694 B2 | 9/2006 | Miura et al. |
| 7,118,591 B2 | 10/2006 | Frank et al. |
| 7,123,968 B1 | 10/2006 | Casscells, III et al. |
| 7,211,070 B2 | 5/2007 | Soroudi |
| 7,231,922 B2 | 6/2007 | Davison et al. |
| D546,459 S | 7/2007 | Banryu |
| D552,736 S | 10/2007 | Yamaoka |
| D553,750 S | 10/2007 | Yamaoka |
| 7,357,500 B2 | 4/2008 | Schwebel |
| 7,442,174 B2 | 10/2008 | Butler |
| 7,513,893 B2 | 4/2009 | Soroudi |
| 7,594,728 B2 | 9/2009 | Seal et al. |
| D612,941 S | 3/2010 | Youngquist et al. |
| D614,774 S | 4/2010 | Gausmann et al. |
| 7,712,899 B2 | 5/2010 | Tanassi et al. |
| 7,976,573 B2 | 7/2011 | Korb et al. |
| D645,565 S | 9/2011 | Smith et al. |
| 2001/0041886 A1 | 11/2001 | Durkin et al. |
| 2002/0035345 A1 | 3/2002 | Beck |
| 2002/0099094 A1 | 7/2002 | Anderson |
| 2002/0111608 A1 | 8/2002 | Baerveldt et al. |
| 2002/0128696 A1 | 9/2002 | Pearl et al. |
| 2003/0056281 A1 | 3/2003 | Hasegawa |
| 2003/0065277 A1 | 4/2003 | Covington |
| 2003/0114426 A1 | 6/2003 | Pflugfelder et al. |
| 2003/0139790 A1 | 7/2003 | Ingle et al. |
| 2003/0195438 A1 | 10/2003 | Petillo |
| 2003/0211043 A1 | 11/2003 | Korb |
| 2003/0233135 A1 | 12/2003 | Yee |
| 2004/0064169 A1 | 4/2004 | Briscoe et al. |
| 2004/0064171 A1 | 4/2004 | Briscoe et al. |
| 2004/0076695 A1 | 4/2004 | Gilbard |
| 2004/0111138 A1 | 6/2004 | Bleam et al. |
| 2004/0153093 A1 | 8/2004 | Donovan |
| 2004/0237969 A1 | 12/2004 | Fuller |
| 2004/0249427 A1 | 12/2004 | Nabilsi |
| 2005/0022823 A1 | 2/2005 | Davison et al. |
| 2005/0119629 A1 | 6/2005 | Soroudi |
| 2005/0143798 A1 | 6/2005 | Bleam et al. |
| 2005/0220742 A1 | 10/2005 | Breen |
| 2006/0018953 A1 | 1/2006 | Guillon et al. |
| 2006/0030604 A1 | 2/2006 | Elsinger et al. |
| 2006/0055878 A1 | 3/2006 | Yee |
| 2006/0104914 A1 | 5/2006 | Soroudi |
| 2006/0139569 A1 | 6/2006 | Schwebel |
| 2006/0154901 A1 | 7/2006 | Pflugfelder et al. |
| 2006/0157064 A1 | 7/2006 | Davison et al. |
| 2006/0183698 A1 | 8/2006 | Abelson |
| 2006/0233859 A1 | 10/2006 | Whitcup et al. |
| 2007/0016256 A1 | 1/2007 | Korb et al. |
| 2007/0049913 A1 | 3/2007 | Grenon et al. |
| 2007/0173799 A1 | 7/2007 | Hsia |
| 2007/0203462 A1 | 8/2007 | Soroudi |
| 2007/0280924 A1 | 12/2007 | Daniels et al. |
| 2008/0051741 A1 | 2/2008 | Grenon et al. |
| 2008/0075787 A1 | 3/2008 | Hibino |
| 2008/0132973 A1 | 6/2008 | Lord et al. |
| 2009/0043365 A1 | 2/2009 | Friedland et al. |
| 2009/0137533 A1 | 5/2009 | Adkins, Jr. |
| 2009/0306111 A1 | 12/2009 | Nakamura et al. |
| 2010/0100029 A1 | 4/2010 | Maskin |
| 2010/0292630 A1 | 11/2010 | Maskin |
| 2011/0039805 A1 | 2/2011 | Pflugfelder et al. |
| 2011/0059902 A1 | 3/2011 | Sullivan et al. |
| 2011/0059925 A1 | 3/2011 | Donnenfeld |
| 2011/0124725 A1 | 5/2011 | Maskin |
| 2011/0172302 A1 | 7/2011 | Dalton et al. |

FOREIGN PATENT DOCUMENTS

| | | |
|---|---|---|
| DE | 202005011496 U1 | 7/2006 |
| EP | 2151438 A1 | 2/2010 |
| EP | 1587468 B1 | 1/2011 |
| JP | 06269473 | 9/1994 |
| JP | 10085248 A | 4/1998 |
| JP | 11221247 | 8/1999 |
| JP | 200278727 | 3/2002 |
| JP | 2006198249 | 8/2006 |
| JP | 2010155012 A | 7/2010 |
| WO | 99/09965 | 3/1999 |
| WO | 99/58131 A1 | 11/1999 |
| WO | 2004/041134 A1 | 5/2004 |
| WO | 2006058189 A2 | 6/2006 |
| WO | 2008024100 A2 | 2/2008 |
| WO | 2008106228 A2 | 9/2008 |
| WO | 2009064834 A2 | 5/2009 |
| WO | 2011085385 A1 | 7/2011 |

OTHER PUBLICATIONS

Final Rejection mailed Dec. 23, 2009, for U.S. Appl. No. 11/434,446.
Advisory Action mailed Mar. 4, 2010, for U.S. Appl. No. 11/434,446.
Non-Final Rejection mailed Apr. 9, 2010, for U.S. Appl. No. 11/434,446.
Restriction/Election Requirement mailed Oct. 1, 2010, for U.S. Appl. No. 11/434,033.
Non-Final Rejection mailed Jan. 24, 2011, for U.S. Appl. No. 11/434,033.
Korb, Donald et al., "The Effect of Two Novel Lubricant Eye Drops on Tear Film Lipid Layer Thickness in Subjects with Dry Eye Symptoms," Optom. Vis. Sci., vol. 82, No. 7, 2005, pp. 594-601.
Korb, Donald R. et al., "Tear Film Lipid Layer Thickness as a Function of Blinking," Cornea, vol. 13, No. 4, 1994, pp. 354-359.
Knop, E et al., "Meibomian Glands: Part III—Dysfunction—Argument for a Discrete Disease Entity and as an Important Cause of Dry Eye," Ophthalmologe, vol. 106, No. 11, Nov. 2009, pp. 966-979. (Abstract Only).
Knop, E. et al., "Meibomian Glands: Part IV—Functional Interactions in the Pathogenesis of Meibomian Gland Dysfunction (MGD)," Ophthalmologe, vol. 106, No. 11, Nov. 2009, pp. 980-987. (Abstract Only).
Sullivan, David et al., "Do Sex Steroids Exert Sex-Specific and/or Opposite Effects on Gene Expression in Lacrimal and Meibomian Glands?" Molecular Vision, vol. 15, No. 166, Aug. 10, 2009, pp. 1553-1572.
Paugh, Jerry R. et al., "Precorneal Residence Time of Artificial Tears Measured in Dry Eye Subjects," Optometry and Vision Science, vol. 85, No. 8, Aug. 2008, pp. 725-731.
Lemp, Michael A. et al., "Blepharitis in the United States 2009: A Survey-Based Perspective on Prevalence and Treatment." Ocul. Surf, vol. 7, No. 2 Suppl, Apr. 2009, pp. S1-S14.
Matsumoto, Yukihiro et al., "The Evaluation of the Treatment Response in Obstructive Meibomian Gland Disease by In Vivo Laser Confocal Microscopy," Graefes Arch Clin Exp Ophthalmol, vol. 247, No. 6, Jun. 2009, pp. 821-829.
Toyos, Rolando, "Intense Pulsed Light for Dry Eye Syndrome," Cataract & Refractive Surgery Today, Apr. 2009, pp. 1-3.
Donnenfeld, Eric et al., "Topical Ophthalmic Cyclosporine: Pharmacology and Clinical Uses," Survey of Ophthalmology, vol. 54, No. 3, May/Jun. 2009, pp. 321-338.
Suzuki, Tomo et al., "Estrogen and Progesterone Control of Gene Expression in the Mouse Meibomian Gland," Invest. Ophthalmol. Vis. Sci., vol. 49, No. 5, Apr. 2008, pp. 1797-1818.
Vasta, Stephanie, "Aggressive Treatments Developed for Meibomian Gland Dysfunction," Primary Care Optometry News, Nov. 1, 2009, 3 pages.
Korb, Donald R., O.D., et al., "Meibomian Gland Dysfunction and Contact Lens Intolerance" Jnl American Optometric Association, vol. 51, No. 3, Mar. 1980, 9 pages (pp. 243-251).
Korb, Donald R. et al., "Increase in Tear Film Lipid Layer Thickness Following Treatment of Meibomian Gland Dysfunction" Lacrimal Gland, Tear Film and Dry Eye Syndromes: Basic Science Clinical Relevance. Adv. Exp. Med. Biol., vol. 350, 1994, 6 pages (pp. 293-298).
Sullivan, Benjamin D., et al., "Impact of Antiandrogen Treatment on the Fatty Acid Profile of Neutral Lipids in Human Meibomian Gland Secretions," The Journal of Clinical Endocrinology & Metabolism, vol. 85, No. 12, 2000, 8 pages (pp. 4866-4873).
Goto, E., et al. "Treatment of Non-Inflamed Obstructive Meibomian Gland Dysfunction by an Infrared Warm Compression Device" British Journal of Ophthalmology, BJO Online, http://www.bmjjournals.com/cgi/reprintform, vol. 26, 2002, 6 pages (pp. 1402-1407).
Goto, Eiki, et al., "Tear Evaporation Dynamics in Normal Subjects and Subjects with Obstructive Meibomian Gland Dysfunction," Investigative Ophthalmology & Visual Science, vol. 44, No. 2, Feb. 2003, 7 pages (pp. 533-539).
Kuscu, Naci Kemal, et al., "Tear Function Changes of Postmenopausal Women in Response to Hormone Replacement Therapy," Maturitas 44, 63-68, 2003, 6 pages.
Mori, Asako, et al., "Disposable Eyelid-Warming Device for the Treatment of Meibomian Gland Dysfunction," Jpn J Ophthalmol, vol. 47: 578-586, 2003, 9 pages (pp. 578-586).
Olson, Mary Catherine, B.A., et al., "Increase in Tear Film Lipid Layer Thickness Following Treatment with Warm Compresses in Patients with Meibomian Gland Dysfunction" Eye & Contact Lens, vol. 29(2), 2003, 6 pages.
Romero, Juan M., et al., "Conservative Treatment of Meibomian Gland Dysfunction," Eye and Contact Lens, vol. 30, No. 1, 2004, 6 pages (pp. 14-19).
Lemp, Michael A., et al., "The Therapeutic Role of Lipids—Managing Ocular Surface Disease," Refractive Eyecare for Ophthalmologists, vol. 9, No. 6, Jun. 2005, 14 pages.
Mitra, M. et al., "Tear Film Lipid Layer Thickness and Ocular Comfort after Meibomian Therapy via Latent Heat with a Novel Device in Normal Subjects" Eye, vol. 19, 2005, 4 pages (pp. 657-660).
Paugh, J.R. et al., "Meibomian Therapy in Problematic Contact Lens Wear," Entrez PubMed, Optom Vis Sci. Nov. 1990; 68(11): 803-6, 1 page.
Foulks, Gary N. et al., "Topical Azithromycin Therapy for Meibomian Gland Dysfunction: Clinical Response and Lipid Alterations," Cornea, vol. 29, No. 7, Jul. 2010, pp. 781-788.
Butovich, Igor et al., "Meibomian Lipid Glands and the Impact of Temperature," Investigative Opthalmology & Visual Science, vol. 51, No. 11, Nov. 2010, pp. 5508-5518.
Korb, Donald R. et al., "Restoration of Meibomian Gland Functionality with Novel Thermodynamic Treatment Device—A Case Report," Cornea, vol. 29, No. 8, Aug. 2010, pp. 930-933.
Akyol-Salman, Ilknur et al., "Efficacy of Topical N-Acetylcysteine in the Treatment of Meibomian Gland Dysfunction," Journal of Ocular Pharmacology and Therapeutics, vol. 26, No. 4, Aug. 1, 2010, pp. 329-333.
Wang, Y. et al., "Baseline Profiles of Ocular Surface and Tear Dynamics After Allogeneic Hematopoietic Stem Cell Transplantation in Patients With or Without Chronic GVHD-Related Dry Eye," Bone Marrow Transplantation, vol. 45, No. 6, Jun. 2010, pp. 1077-1083.
Korb, Donald R. et al., "Lid Wiper Epitheliopathy and Dry Eye Symptoms," Eye & Contact Lens, vol. 31, No. 1, 2005, pp. 2-8.
Foulks, Gary N., "Meibomian Gland Dysfunction: The Past, Present, and Future," Eye and Contact Lens, vol. 36, No. 5, Sep. 2010, pp. 249-253.
Blackie, Caroline a. et al., "Nonobvious Obstructive Meibomian Gland Dysfunction" Cornea, vol. 29, No. 12, Dec. 2010, pp. 1333-1345.
Haque, Reza M. et al., "Multicenter Open-label Study Evaluating the Efficacy of Azithromycin Opthalmic Solution 1% on the Signs and Symptoms of Subjects with Blepharitis," Cornea, vol. 29, No. 8, Aug. 2010, pp. 871-877.
Maskin, Steven L., "Intraductal Meibomian Gland Probing Relieves Symptoms of Obstructive Meibomian Gland Dysfunction," Cornea, vol. 29, No. 10, Oct. 2010, pp. 1145-1152.
Dausch, Eva et al., "Dry Eye Syndrome in Women's Health and Gynecology: Etiology, Pathogenesis and Current Therapeutic Strategies," Geburtshilfe and Frauenheilkunde, vol. 70, No. 9, Jan. 1, 2010, pp. 707-711. (Abstract Only).
"New Over-the-Counter Dry Eye Drop Now Available to Help Estimated 40 Percent of Americans Who Suffer from Occasional or Chronic Dry Eye" Business Wire News Release, Published Mar. 31, 2008.
Gupta, S. et al. "Docetaxel-induced Meibomian Duct Inflammation and Blockage Leading to Chalazion Formation" Prostate Cancer Prostatic Diseases, vol. 10, No. 4, 2007.
Aronowicz, J D et al. "Short Term Oral Minocycline Treatment of Meibomiantis" Br. J Opthalmol, vol. 90, No. 7, Jul. 2006.
Goto, E. et al, "Treatment of Non-Inflamed Obstructive Meibomian Gland Dysfunction by an Infrared Warm Compression Device" Br J Opthalmol, vol. 86, No. 12, Dec. 2002.
"arGentis Licenses Third Treatment for Dry Eye Syndrome" www.businesswire.com, May 12, 2008.
Blackie, Caroline k et al., "Recovery Time of an Optimally Secreting Meibomian Gland," Cornea, vol. 28, No. 3, Apr. 2009, pp. 293-297.

Blackie, Caroline A. et al., "Inner Eyelid Surface Temperature as a Function of Warm Compress Methodology," Optometry and Vision Science, vol. 85, No. 8, Aug. 2008, pp. 675-683.

Kokke, K.H. et al., "Oral Omega-6 Essential Fatty Acid Treatment in Contact Lens Associated Dry Eye," Contact Lens and Anterior Eye, vol. 31, No. 3, 2008, pp. 141-146.

Korb, Donald R., Slide entitled "Inner Eyelid Surface Temperature as a Function of Warm Compress Methodology," from presentation entitled "The Tear Film and Dry Eye States a Fertile Research Area," University of California at Berkeley, School of Optometry, Apr. 11, 2008. 2 pages.

Korb, Donald R. et al., Slide entitled "Inner Eyelid Surface Temperature as a Function of Warm Compress Methodology," from presentation entitled "The Greatest Anterior Segment Disease and Contact Lens Complications Course," AOA Meeting, Seattle, Washington, Jun. 27, 2008, 2 pages.

Geerling, G., et al., "The international workshop on meibomian gland dysfunction: report of the subcommittee on management and treatment of meibomian gland dysfunction," Mar. 2011, pp. 2050-2064, Investigative Ophthalmology & Visual Science, vol. 52, No. 4.

Korb, Donald R. and Blackie, Caroline A., "Meibomian gland therapeutic expression: Quantifying the applied pressure and the limitation of resulting pain," Eye and Contact Lens, Sep. 2011, pp. 298-301, vol. 37, No. 5, Philadelphia, PA.

Holifield, Karintha and Lazzaro, Douglas R., "Case report: Spontaneous *Stenotrophomonas maltophilia* keratitis in a diabetic patient," Eye and Contact Lens, Sep. 2011, pp. 326-327, vol. 37, No. 5, Philadelphia PA.

Cunniffe, M. Geraldine et al., "Topical antiglaucoma treatment with prostaglandin analogues may precipitate meibomian gland disease," Ophthalmic Plastic and Reconstructive Surgery, Sep.-Oct. 2011, p. 128-129, vol. 27, No. 9, Lippincott Williams and Wilkins, Philadelphia, PA.

Official Action Issued May, 10 2011 for Japanese Patent Application No. 2009-525529.

Partial Translation of Japanese Patent Publication No. 11-221247A, previously submitted in IDS dated Feb. 14, 2008.

Partial Translation of Japanese Patent Publication No. 2006-198249A, previously submitted in IDS dated Feb. 14, 2008.

Wolff, Eugene, "Eugene Wolffs Anatomy of the eye and orbit : including the central connexions, development, and comparative anatomy of the visual apparatus (book)," 1976, p. 170.

Tobler, David, et al., "Nanotech Silver Fights Microbes in Medical Devices," Medical Device and Diagnostic Industry, May 1, 2005, p. 164.

Unknown, "Introducing: Thermofoil Heaters", Minco Bulletin HS-202, 2002, 9 pages.

Unknown, "IFU Manual for PNT Model 1000—Rev H," Feb. 11, 2009, http://www.oi-pnt.com/files/IFU_Manual_Model_1000_English_with_Bargode_Rev_H.pdf, 24 pages.

Mori, A., et al., "Efficacy of the Treatment by the Disposable Eyelid Warming Instrument for Meibomian Gland Dysfunction," Poster Presentation, Hall A, The Association for Research and Vision in Ophthalmology Annual Meeting, Fort Lauderdale, Florida, Apr. 30, 2000, 1 page.

Unknown, "TearScience Launches Breakthrough Technology in Canada to Address the Root Cause of Evaporative Dry Eye," Business Wire, Jun. 9, 2011, http://www.businesswire.com/news/home/20110609005860/en/TearScience-Launches-Breakthrough-Technology-Canada-Address-Root, 2 pages.

Friedland, B., et al., "A novel thermodynamic treatment for meibomian gland dysfunction," Current Eye Research, vol. 36, No. 2, Feb. 2011, pp. 79-87.

SYSTEM FOR INNER EYELID HEAT AND PRESSURE TREATMENT FOR TREATING MEIBOMIAN GLAND DYSFUNCTION

RELATED APPLICATIONS

The present application claims priority to U.S. Provisional Patent Application No. 60/880,850 entitled "Method and Apparatus for Treating Meibomian Gland Obstructive Disease," filed on Jan. 17, 2007, which is incorporated herein by reference in its entirety.

The present application is also a continuation-in-part patent application of U.S. application Ser. No. 11/434,033 entitled "Method and Apparatus for Treating Gland Dysfunction Employing Heated Medium," filed on May 15, 2006, which is incorporated herein by reference in its entirety.

The present application is also a continuation-in-part patent application of U.S. application Ser. No. 11/434,446 entitled "Method and Apparatus for Treating Gland Dysfunction," filed on May 15, 2006, now abandoned which is incorporated herein by reference in its entirety.

The present application is also a continuation-in-part patent application of U.S. application Ser. No. 11/434,054, now U.S. Pat. No. 8,083,787 entitled "Method and Apparatus for Treating Meibomian Gland Dysfunction," filed on May 15, 2006, which is incorporated herein by reference in its entirety.

The present application is also a continuation-in-part patent application of U.S. application Ser. No. 11/541,291 entitled "Method and Apparatus for Treating Meibomian Gland Dysfunction Employing Fluid Jet," filed on Sep. 29, 2006, now U.S. Pat. No. 7,981,095 which is incorporated herein by reference in its entirety.

The present application is also a continuation-in-part patent application of U.S. application Ser. No. 11/541,418, not U.S. Pat. No. 7,981,145 entitled "Treatment of Meibomian Glands," filed on Sep. 29, 2006, which is incorporated herein by reference in its entirety.

The present application is also a continuation-in-part patent application of U.S. application Ser. No. 11/541,308 entitled "Melting Meibomian Gland Obstructions," filed on Sep. 29, 2006, which is incorporated herein by reference in its entirety.

The present application is also a continuation-in-part patent application of U.S. application Ser. No. 11/893,669 entitled "Meibomian Gland Illuminating and Imaging," filed on Aug. 17, 2007, which is incorporated herein by reference in its entirety.

FIELD OF THE INVENTION

The field of the invention relates in general to treatment of mammalian eyes. More particularly, the present invention relates to treatment of meibomian gland dysfunction (MGD), which may be either responsible for or be a contributing factor to a patient suffering from a "dry eye" condition. A patient's meibomian glands are treated to aid in facilitating a sufficient protective lipid layer being generated and retained on the tear film of the eye to retain aqueous.

BACKGROUND OF THE INVENTION

In the human eye, the tear film covering the ocular surfaces is composed of three layers. The innermost layer in contact with the ocular surface is the mucus layer. The mucus layer is comprised of many mucins. The middle layer comprising the bulk of the tear film is the aqueous layer. The aqueous layer is important in that it provides a protective layer and lubrication to prevent dryness of the eye. Dryness of the eye can cause symptoms such as itchiness, burning, and irritation, which can result in discomfort. The outermost layer is comprised of many lipids known as "meibum" or "sebum." This outermost lipid layer is very thin, typically less than 250 nm in thickness. The lipid layer provides a protective coating over the aqueous and mucus layers to limit the rate at which these underlying layers evaporate. A higher rate of evaporation of the aqueous layer can cause dryness of the eye. Thus, if the lipid layer is not sufficient to limit the rate of evaporation of the aqueous layer, dryness of the eye may result. The lipid layer also lubricates the eyelid during blinking, which prevents dry eye. Dryness of the eye is a recognized ocular disease, which is generally known as "dry eye." If the lipid layer can be improved, the rate of evaporation is decreased, lubrication is improved, and partial or complete relief of the dry eye state is achieved.

The sebum that forms the outermost lipid layer is secreted by meibomian glands 10 of the eye, as illustrated in FIGS. 1-3 of this application. The meibomian glands are enlarged, specialized sebaceous-type glands (hence, the use of "sebum" to describe the secretion) located on both the upper eyelid 12 and lower eyelid 14. The meibomian glands contain orifices 16 that are designed to discharge lipid secretions onto the lid margins, thus forming the lipid layer of the tear film as the mammal blinks and spreads the lipid secretion. The typical human upper eyelid 12 has about twenty five (25) meibomian glands and the lower eyelid 14 has about twenty (20) meibomian glands, which are somewhat larger than those located in the upper lid. Each meibomian gland 10 has a straight long central duct 18 lined with four epithelial layers on the inner surface of the duct 18. Along the length of the central duct 18 are multiple lateral out-pouching structures 20, termed acini, where the secretion of the gland is manufactured. The inner lining of each acinus 20 differs from the main central duct 18 in that these specialized cells provide the secretions of the meibomian gland. The secretions flow from each acinus 20 to the duct 18.

While it has not been established with certainty, there appears to be a valve system between each acinus 20 and the central duct 18 to retain the secretion until it is required, at which time it is discharged into the central duct 18. The meibomian secretion is then stored in the central duct 18 and is released through the orifice of each gland onto the lid margin. Blinking and the squeezing action of the muscle of Riolan surrounding the meibomian glands 10 are thought to be the primary mechanism to open the orifice for the release of secretion from the meibomian gland 10. Blinking causes the upper lid 12 to pull a sheet of the lipids secreted by the meibomian glands 10 over the other two layers of the tear film, thus forming a type of protective coating which limits the rate at which the underlying layers evaporate. Thus, a defective lipid layer or an insufficient quantity of such lipids can result in accelerated evaporation of the aqueous layer which, in turn, causes symptoms such as itchiness, burning, irritation, and dryness, which are collectively referred to as "dry eye."

Various treatment modalities have been developed to treat the dry eye condition. These modalities include drops, which are intended to replicate and replace the natural aqueous tear film and pharmaceuticals which are intended to stimulate the tear producing cells. For example, eye drops such as Refresh Endura™, Soothe™, and Systane™ brand eye drops are designed to closely replicate the naturally occurring healthy tear film. However, their use and administration are merely a treatment of symptoms and not of the underlying cause. Further, the use of aqueous drops is generally for an indefinite length of time and consequently, extended use can become burdensome and costly.

Pharmaceutical modalities, such as the use of tetracycline, have also been suggested to treat meibomian gland dysfunction. One such treatment is disclosed in U.S. Patent Application Publication No. 2003/0114426 entitled "Method for Treating Meibomian Gland Disease," U.S. Pat. No. 6,455,583 entitled "Method for Treating Meibomian Gland Disease" to Pflugfelder et al., and PCT Publication Application No. WO 99/58131 entitled "Use of Tetracyclines for Treating Meibomian Gland Disease." However, this treatment has not proven to be universally clinically effective, and it may be unnecessary in cases where MGD is the result of obstruction of the gland without infection.

The use of corticosteroids has also been proposed to treat MGD as disclosed in U.S. Pat. No. 6,153,607 entitled "Non-preserved Topical Corticosteroid for Treatment of Dry Eye, filamentary Keratitis, and Delayed Tear Clearance (or Turnover)" to Pflugfelder et al. Again, this proposed treatment appears to treat the symptoms of dry eye, as opposed to treatment of the underlying cause.

Additionally, the use of topically applied androgens or androgen analogues has also been used to treat acute dry eye signs and symptoms in keratoconjuctivitis sicca. This is disclosed in U.S. Pat. Nos. 5,958,912 and 6,107,289, both entitled "Ocular Therapy in Keratoconjunctivitis Sicca Using Topically Applied Androgens or TGF-beta." and both to Sullivan.

There is a correlation between the tear film lipid layer and dry eye disease. The various different medical conditions and damage to the eye and the relationship of the lipid layer to those conditions are reviewed in Surv Opthalmol 52:369-374, 2007. It is clear that the lipid layer condition has the greatest effect on dry eye disease when compared to the aqueous layer or other causes. Thus, while dry eye states have many etiologies, the inability of the meibomian gland 10 to sufficiently generate the lipid layer is a common cause of common dry eye state. This state is the condition known as "meibomian gland dysfunction" (MGD). MGD is a disorder where the meibomian glands 10 are obstructed or occluded. FIG. 3 illustrates an example of such obstructions 22, 24 or occlusions 22, 24. Plug obstructions 22 can occur in the orifice 16 of the central duct 18. Alternatively, obstructions and occlusions 22, 24 can occur that block particular acinus 20. The obstructions or occlusions 22, 24 can mean that the meibomian glands 10 are partially blocked or plugged, completely blocked or plugged, or any variation thereof. Obstructions and occlusions 22, 24 can be in a solid, semi-solid, or thickened, congealed secretion and/or a plug, leading to a compromise, or more specifically, a decrease in or cessation of secretion. Also, with a reduced or limited secretion, the meibomian gland 10 may be compromised by the occluded or obstructive condition often evidenced by a yellowish color, indicating a possible infection state. Alternatively, the meibomian gland 10 may be otherwise compromised so that the resulting protective lipid film is not adequate for preventing evaporation of the underlying layers on the eye.

MGD is frequently the result of keratotic obstructions, which partially or completely block the meibomian gland orifices 16 and/or the central duct (canal) 18 of the gland 10, or possibly the acini or acini valves (assuming they do in fact exist) or the acini's junction 20 with the central duct 18. Such obstructions 22, 24 compromise the secretory functions of the individual meibomian glands 10. More particularly, these keratotic obstructions may be associated with or result in various combinations of bacteria, sebaceous ground substance, dead, and/or desquamated epithelial cells (see, Meibomian Gland Dysfunction and Contact Lens Intolerance, Journal of the Optometric Association, Vol. 51, No. 3, Korb et al., (1980), pp. 243-51).

Hormonal changes, which occur during menopause and particularly changing estrogen levels, can result in thickening of the oils secreted by the meibomian glands 10. This may result in clogged gland orifices. Further, decreased estrogen levels may also enhance conditions under which staphylococcal bacteria can proliferate. This can cause migration of the bacteria into the glands 10 compromising glandular function and further contributing to occlusion, thus resulting in a decreased secretion rate of the meibomian gland 10.

When the flow of secretions from the meibomian gland 10 is restricted due to the existence of an occlusion 22, 24, cells on the eyelid margin have been observed to grow over the gland orifice 16. This may further restrict sebum flow and exacerbate a dry eye condition. Additional factors may also cause or exacerbate meibomian gland dysfunction including age, disorders of blinking, activities such as computer use which compromise normal blinking, contact lens use, contact lens hygiene, cosmetic use, or other illness, particularly diabetes. It has been theorized that the acini 20 of the glands 10 may have valves at their junction with the main channel of the gland 10. The inventors theorize that if these valves exist, they may also become obstructed in some instances leading to reduced or blocked flow from the acini 20. These obstructions or occlusions 22, 24 may have various compositions.

The state of an individual meibomian gland 10 can vary from optimal, where clear meibomian fluid is produced; to mild or moderate meibomian gland dysfunction where milky fluid or inspissated or creamy secretion is produced; to total blockage, where no secretion of any sort can be obtained (see "Increase in Tear Film Lipid Layer Thickness Following Treatment of Meibomian Gland Dysfunction," Lacrimal Gland, Tear Film, and Dry Eye Syndromes," Korb, et al., pp. 293-98, Edited by D. A. Sullivan, Plenum Press, New York (1994)). Significant chemical changes of the meibomian gland 10 secretions occur with meibomian gland dysfunction and consequently, the composition of the naturally occurring tear film is altered, which in turn, contributes to dry eye.

MGD may be difficult to diagnose, because visible indicators are not always present. For example, meibomitis, an inflammation of the meibomian glands 10, can lead to MGD. Meibomitis may also be accompanied by blepharitis (inflammation of the lids). While meibomitis is obvious by inspection of the external lids, MGD may not be obvious even when examined with the magnification of the slit-lamp biomicroscope. This is because there may not be external signs or the external signs may be so minimal that they are overlooked. The external signs of MGD without obvious lid inflammation may be limited to subtle alterations of the meibomian gland orifices 16, overgrowth of epithelium over the orifices 16, and pouting of the orifices 16 of the glands 10 with congealed material acting as obstructions. In severe instances of MGD without obvious lid inflammation, the changes may be obvious, including serrated or undulated lid margins, orifice recession and more obvious overgrowth of epithelium over the orifices 16, and pouting of the orifices 16.

Thus to summarize, the meibomian glands 10 of mammalian (e.g., human) eyelids secrete oils that prevent evaporation of the tear film and provide lubrication to the eye and eyelids. These glands can become blocked or plugged (occluded) by various mechanisms leading to so-called "dry eye syndrome." While not the only cause, MGD is a known cause of dry eye syndrome. The disorder is characterized by a blockage of some sort within the meibomian glands 10 or at their surface preventing normal lipid secretions from flowing from the meibomian glands 10 to form the lipid layer of the tear film. Such secretions serve to prevent evaporation of the aqueous tear film and lubricate the eye and eyelids 12, 14, hence, their absence can cause dry eye syndrome. Obstructions or occlusions 22, 24 of the meibomian glands 10 may be present over or at the orifice 16 of the gland 10, in the main channel 18 of the gland 10, which may be narrowed or blocked, or possibly in other locations including the passages from the acini 20 to the main channel 18.

While the present state of the art provides a number of treatments for dry eye, there is a need to treat the underlying cause, as opposed to the symptom. Many patients suffer from dry eye as a result of obstructions or occlusions in the meibomian glands. Thus, a need exists to provide effective treatment of the meibomian glands to restore a sufficient flow of sebum to the lipid layer of the eye to limit the rate of evaporation of the underlying layers. This includes loosening or removing possible obstructions or occlusions 22, 24 in the meibomian glands 10. FIG. 2 of the application shows the obstructions or occlusions 22, 24 of FIG. 3 in the meibomian glands 10 removed to restore sebum flow to the lipid layer.

SUMMARY OF THE DETAILED DESCRIPTION

One embodiment of the present invention includes the breakthrough and previously unknown method of applying heat to the inner surface of the eyelid to treat dry eye caused by meibomian gland dysfunction (MGD). Applying heat to the inside of the eyelid can effectively and efficiently raise the temperature at the meibomian glands to a temperature sufficient to melt, loosen, or soften more serious occlusions or obstructions in the meibomian glands. The occlusions or obstructions can then be physically expressed to improve sebum flow from the meibomian glands to reduce evaporation of the aqueous layer.

Some patients have obstructions or occlusions in their meibomian glands that will not sufficiently melt, loosen, or soften to be expressed without attaining heightened temperatures at the meibomian glands. In many instances, these temperatures either cannot be achieved when applying heat to the outside of the eyelid, or these temperatures may be achievable, but only after applying heat to the outside of the eyelid for a significant period of time. Heightened temperatures may also only be achieved by applying heat at unsafe temperatures that would either produce an unacceptable pain response to the patient or damage to the patient's eyelid. This is because of the temperature drop between the outside of the eyelid and the meibomian glands due to conductive heat loss. Heat applied to the outside of the eyelid must conductively travel through the eyelid tissue and through the tarsal plate that encases the meibomian glands inside the eyelid. As an example, it may take twenty to thirty minutes for the temperature at the meibomian glands to reach only a temperature of 41 to 42 degrees Celsius when applying heat to the outside of the eyelid that will not burn or damage the patient's eyelid or surrounding tissue. Temperatures may need to reach between 43 to 45 degrees Celsius, for example, for melting, loosening, or softening of certain obstructions or occlusions in a patient's meibomian glands.

Until the present application, it was only known to apply heat to the outside of the eyelid to treat meibomian gland dysfunction (MGD). Medical professionals would have thought it counterintuitive to apply heat to the inside of the eyelid. It was thought that applying heat to the inside of the eyelid would risk damage to the eyelid or the eyeball itself. Previous studies of heat application to skin showed that damage could occur for temperatures at or above 45 degrees Celsius. These studies were conducted on external keratinized skin. The tissue on the inner eyelids is non-keratinized epithelium, and as such, is not as well protected from heat as keratinized skin. Thus, one would naturally believe that applying heat to the inside of the eyelid would produce a pain response at lower temperatures than on the outer eyelid surface. However, it has been surprisingly discovered that applying heat to the inside of the eyelid is not only safe, but effective at dislodging obstructions and/or occlusions in the meibomian glands as part of a MGD treatment.

It was hypothesized that heating the inside of the eyelid may provide a more efficient conductive heat transfer to the meibomian glands. Attaining a more efficient heat transfer may allow higher temperatures to be attained at the meibomian glands and/or in a more efficient time to melt, loosen, or soften more serious obstructions or occlusions in the meibomian glands. Heat conduction increases with thinner tissue. The meibomian glands are located closer to the inside surface of the eyelid than the outside surface of the eyelid. Further, there is no tarsal plate located between the inside of the eyelid and the meibomian glands. Thus, it was discovered than conductive heat transfer to the meibomian glands is more efficient when heating the inside of the eyelid.

In this regard, an experiment was carried out where heat was applied to the inside of the eyelid (and more particularly the palpebral conjunctiva) against traditional notions and known principles. It was discovered that heat could be applied to the inside of the eyelid without damaging the patient's eye if temperature is regulated. For example, it was determined that most patients can tolerate a surface temperature of 43-44.5 degrees Celsius without anesthesia and without significant pain. It was found that some patients could tolerate temperatures over 44.5 degrees Celsius without anesthesia. Further, it was discovered that heightened temperatures at the meibomian glands could be attained and in less time when applying heat to the inside of the eyelid than to the outside of the eyelid due to more effective conductive heat transfer and the proximity of the heating to the eyelid surface.

While not limiting to the present invention, the ability to effectively and more efficiently raise the temperature at the meibomian glands by applying heat to the inside or inner surface of the eyelid may prove instrumental in reaching the melting, loosening, or softening points of obstructions or occlusions. Applying heat to the inside of the eyelid can also include applying heat to the meibomian glands orifices that are located at the inner surface of the eyelid at the lid margin. The orifices may also be obstructed or occluded. The application of heat to the inside of the eyelid and proximate or directly to the meibomian glands orifices may also prove instrumental in restoring sufficient sebum flow for the lipid layer. When the term or phrase applying heat to the "inside" or "inner surface" of the eyelid is referenced in this application, such also encompasses the application of heat to the meibomian glands orifices.

The application of heat may be regulated, meaning that a heating means or element is controlled to be within the temperatures and means that are safe for the inner surface of the eyelid and at a sufficient temperature for melting, loosening, or softening an occlusion or obstruction in the meibomian gland. The heat is maintained for a period of time sufficient to melt, loosen, or soften the occlusions or obstructions. Either during heat application or after heat application is removed, the occlusions or obstructions in the meibomian glands are expressed to remove obstructions or occlusions thus providing an improved pathway to restore or improve sebum flow from the gland.

In one embodiment, increasing the temperature of the surface of the palpebral conjunctiva to at least 37 degrees Celsius can begin to provide therapeutic effect for milder cases of MGD. A therapeutic temperature can be any temperature above body temperature. One preferred range for treatment is 43 to 45 degrees Celsius, with a target of 43 to 44.5 degrees Celsius. A time range to apply heat may be a period between 1-10 minutes, and may be limited to a range of 3-6 minutes. Temperature in this range has been found effective and comfortable to the patient when treating MGD.

In one embodiment, the application of heat may be regulated. Regulated heat can include controlling heat according to a temperature profile. The temperature profile may be a constant temperature, include ramp-ups, ramp-downs, peaks and valleys. Further, the temperature profile may include heat pulses or be modulated with various characteristics, including the use of on/off switching or pulse width modulation (PWM) techniques for example. The use of modulated heat may allow the temperature to be raised even higher at the eyelid without damages to the patient's eyelid since the increased temperatures are applied for shorter periods of time. Obstructions or occlusions in the meibomian glands may have melting, loosening, or softening points that are beyond temperatures that may be applied without the use of modulated heat. The temperature needed to melt, loosen, or soften obstructions or occlusions may depend on how keratinized the obstruction or occlusion is. Not all obstructions or occlusions have the same melting, loosening, or softening points.

By example only, elevated temperatures between 45 and 55 degrees Celsius may be possible when applying regulated heat, especially if the eyelid has been anesthetized. However, heat should always be applied to the eyelid at temperatures that take into consideration the pain response of the patient as well as whether damage will occur to the patient's eyelid and/or surrounding tissues. Depending on the severity of the patient's MGD or the patient's pain tolerance, elevated temperatures may be used with patients on an individualized basis when applying heat. It has been found that lighter skinned patients can generally tolerate less heat than darker skinned patients, and darker skinned patients tend to exhibit less inflammation as a result of exposure to the heat. Other factors, including humidity, may contribute to a patient's tolerance of greater temperatures. For example, humans can generally tolerate heat up to 70 to 80 degrees Celsius in dry saunas where humidity is low. Application of heat in higher humidity environments may cause pain and/or burns to occur at lower temperatures.

Severe cases of MGD that cause substantial irritation or risk to the patient may call for temperatures that would produce category one or two burns to the patient's eyelid, since these burns generally heal. Temperatures that cause category three burns should be avoided. In summary, treatment times and/or temperature can be adjusted to account for these differences. The present invention is not limited to any particular temperature or time ranges as long as therapeutic temperature is being applied to the meibomian glands.

The regulated heat can be maintained at a therapeutic temperature for a treatment period. The treatment period can be approximately 1 to 10 minutes for example. The heat could also be repeatedly applied and maintained for a desired period of time to keep the occlusion or obstruction in a melted, loosened, or softened state. Either during or after such treatment by regulated heat, mechanical expression of lipids and other fluids from the meibomian glands has been found to clear obstructions which have essentially melted or been placed in a suspension state (by virtue of melting materials binding solids together).

In one embodiment, after expression of the occlusions or obstructions is performed, an optional pharmacological agent may be applied to the meibomian gland to promote the free flow of sebum and/or reduce or prevent inflammation or infections of the eye or eyelids. Many pharmacological agents have been proposed for treatment of dry eye syndrome, any of which may be effective or more effective upon clearing of obstructions within the meibomian glands. Some of the pharmacological agents that may be utilized include, but are not limited to: antibiotics such as topical or oral tetracycline and chemically modified tetracycline, testosterone, topical or oral corticosteroids, topical androgens or androgen analogues, omega 3 fatty acid compounds such as fish oils, Laennec, enzymes that promote lipid production, agents that stimulate production of enzymes that promote lipid production, and/or any agent which acts as a secretagogue to enhance meibomian gland secretion or secretion of other tear components. For example, androgen and androgen analogues and TGF-beta have been reported to act as a secretagogue to enhance meibomian gland secretion.

These compounds are illustrative examples of appropriate pharmacological agents, but those skilled in the art will appreciate that other pharmacological compounds may be utilized.

Also, agents, such as Restasis (cyclosporine A), that replace or promote production of the tear component may also be applied more effectively after treating the meibomian glands according to the present invention. Treating the meibomian glands improves the lipid layer thus reducing evaporation and conserving the aqueous layer. Conservation of the aqueous layer reduces the need for tear substitutes to be applied through tear component agents. Thus, tear component agents may not have to be used as often when employing the present invention to treat a patient's MGD.

In the course of experimenting with the application of heat to the inside of the eyelid, it was also discovered that convective heat losses occur due to blood flow in the blood vessels located inside the eyelid. Blood flow through blood vessels located inside the eyelid produces convective heat losses. The blood flow serves as a natural "heat sink" provided by the body. Convective heat loss is lessened when applying heat to the inside of the eyelid than when applying heat to the outside of the eyelid. This is because fewer blood vessels are located between the meibomian glands and the inside of the eyelid than the outside of the eyelid. The meibomian glands are located closer to the inside of the eyelid. However, convective heat loss still occurs when heating the inside of the eyelid. However, it was discovered that if the blood flow was reduced, convective heat losses could be minimized allowing for temperatures to be attained and sustained at the meibomian glands in an even more efficient manner and in less time.

Thus, one embodiment of the present invention also includes the further application of force to the patient's eyelid in addition to heat. The application of force can further assist in obtaining higher temperatures more efficiently inside the eyelid at the palpebral conjunctiva and at the meibomian gland in a shorter period of time and thus more efficiently. This is because the application of force may reduce blood flow to the eyelid to reduce convective heat loss, as discussed above.

Applying force can also result in a more efficient conductive heat transfer from an applied heat source, because the pressure created by the force causes the heat source to be compressed against the tissue of the eyelid. This compression can have several benefits. Compression spreads out the tissue to which heating is applied thus making it thinner and improving conductive heat transfer. Compression can also "squeeze out" air pockets at the surface of the eyelid due to the microscopic roughness of skin. Thus, compression of the heat source against the eyelid increases the surface contact between the heat source and the surface of the eyelid (which increases the heat transfer equation) to provide a more effective conductive heat transfer to the meibomian glands. This results in the meibomian glands being heated to the desired temperature level in a shorter period of time due to these gained efficiencies. Further, increased temperatures may be attained that may not have otherwise been obtained, or obtained using less heat or thermal energy. Because the heating is located in close proximity to the eyelid surface and heating is further compressed against the eyelid surface, heat transfer is very efficient providing for the temperature at the surface of the eyelid to be very close to the temperature at the meiboimian glands.

The applied force may be regulated, meaning that a force generating means is controlled to be within pressure ranges that are safe to be applied to the eyelid and at sufficient pressure to allow the temperature at the meibomian gland to be raised sufficiently. The force can also be a constant force and be provided manually. The force may be applied during heating, after heating, or both during and after heating. In either case, the force may assist in expressing occlusions or obstructions when in a loosened, softened, or melted state from the meibomian glands. The force may include vibratory type forces, including those generated mechanically or those using fluid type devices or mechanisms. The level of force needed to express obstructions or occlusions in the glands may be greatly reduced when heat is applied to the obstructions or occlusions to place them in a melted, softened, or loosened state.

The application of force can also stimulate the movement of fluids or suspensions of occlusions or obstructions from the glands. The present invention can be used with devices, which generally apply a regulated force or milking action to the eyelid to express the fluids or suspensions or to otherwise mechanically stimulate the movement of fluids from the glands. In some instances, a small, gentle, continuous force applied to the eyelid will assist in expression of the fluids and suspensions. Vibration can also be used when applying force simultaneously or immediately after the heating to further assist in the expression.

Any apparatus, device, or tool can be used to apply heat and/or force to the eyelids to treat MGD. In one embodiment, a force can be applied to the outside of the eyelid while heat is applied to the inside of the eyelid to treat MGD. The heating of the inner surface of the upper or lower eyelid can be done by any convenient method. The lids can be heated one at a time or both at once, depending on the time available to remove the occlusions once heated and the device or method to heat being employed is removed. Several heat and force application devices are disclosed.

One device for heating the palpebral conjunctiva is disclosed in U.S. Provisional Patent Application Ser. No. 60/880,850, previously referenced above and to which the present application claims priority. In this application, a lid warmer containing a heating element is placed in-between the eyeball and against the palpebral conjunctiva. The heating element is energized or powered to generate a heat to the inside of the eyelids when the lens in placed on the eyeball. The lid warmer may also contain an integrated insulator that prevents substantial heat from reaching the eyeball and thus protects the cornea and sclera. The heating element may be biased according to its location in the lid warmer, and in particular to be located behind the insulator proximate the eyelid, to produce more heat on the insides of the eyelid than on the eyeball. The lid warmer may also contain a platform. The platform provides a handle for insertion or adjustment of the heating element, and an area to encapsulate heating components, including an electrical interface to allow an attached heating controller to generate an electrical signal to the heating element to produce a regulated heat to the inside of the eyelid.

The lid warmer may also be used in conjunction with a device that generates a regulated force to the outside of the eyelid when heat is applied to the inside of the eyelid. In one embodiment, an eyecup having an inflatable bladder is placed on the outside of the eyelid while the lens is sitting on the eyeball. The eyecup may include an interface that allows the eyecup to be placed onto the platform extending from the lid warmer. In this manner, when the eyecup is engaged onto the platform and the bladder is inflated, a regulated force is applied to the outside of the eyelid, thus compressing the eyelid against the lid warmer at the inside of the eyelid. Thus, the meibomian glands are "sandwiched" between, meaning surrounded by, the eyecup and the lid warmer, wherein the eyecup applies a force vector towards the lid warmer to create a pressure on the eyelid and at the meibomian glands within the eyelid. This assists in loosening obstructions or occlusions in the meibomian glands as well as reduces blood flow in the eyelids to prevent convective heat loss of the heat generated by the lid warmer.

Alternatively, a membrane could be attached to the eyecup and employed to generate force. The membrane could be made of different materials and materials that stretch, and are resilient. Several embodiments are disclosed involving a lid warmer and eyecup to be used to apply heat and force to the eyelid as part of treating MGD. The present invention is not limited to any particular type of lid warmer and/or force generating apparatus or device.

In another embodiment, force and heat can be applied to tissue proximate the meibomian glands to treat MGD. As discussed above, the application of force can further assist in obtaining higher temperatures at the meibomian glands and in a shorter period of time and thus more efficiently. The application of force can improve conductive heat transfer efficiency and/or reduce convective heat loss. Any apparatus, device, or tool can be used to apply heat and force to the tissue proximate the meibomian glands. The application of force may also allow heat to be maintained for a longer period of time. This is because the application of force may reduce blood flow to the eyelid, thus reducing convective heat loss and increasing conductive heat transfer into the eyelid and to the glands. The heat and/or force applied to the tissue can be regulated, as discussed above. The force may be applied during heating, after heating, or both during and after heating. The force can remain after the heat is removed, thus increasing the time before the body's heat sink effect returns the eyelid to normal temperature. The application of force may also assist in expressing the occlusions or obstructions when in a loosened, softened, or melted state from the meibomian glands.

In another embodiment, force can be applied to the inside of the eyelid and heat applied to the outside of the eyelid to treat MGD. As discussed above, the application of force can further assist in obtaining higher temperatures at the meibomian gland and in a shorter period of time and thus more efficiently. The application of force can to improve conductive heat transfer efficiency and/or reduce convective heat loss. Any apparatus, device, or tool can be used to apply heat and force to the outside of the eyelid. The application of force may also allow heat to be maintained on the outside of the eyelid for a longer period of time. This is because the application of force may reduce blood flow to the eyelid, thus reducing convective heat loss and increasing conductive heat transfer into the eyelid and to the glands. The heat applied to the outside of the eyelid and/or the force applied to the inside of the eyelid can be regulated, as discussed above. The force may be applied during heating, after heating, or both during and after heating. The force can remain after the heat is removed, thus increasing the time before the body's heat sink effect returns the eyelid to normal temperature. The application of force may also assist in expressing the occlusions or obstructions when in a loosened, softened, or melted state from the meibomian glands.

In another embodiment, force and heat can both be applied to the outside of the eyelid to treat MGD. As discussed above, the application of force can further assist in obtaining higher temperatures at the meibomian gland and in a shorter period of time and thus more efficiently. The application of force can improve conductive heat transfer efficiency and/or reduce convective heat loss. Any apparatus, device, or tool can be used to apply heat and force to the outside of the eyelid. The application of force may also allow heat to be maintained on the outside of the eyelid for a longer period of time. This is because the application of force may reduce blood flow to the eyelid, thus reducing convective heat loss and increasing conductive heat transfer into the eyelid and to the glands. The heat and/or force applied to the outside of the eyelid can be regulated, as discussed above. The force may be applied during heating, after heating, or both during and after heating. The force can remain after the heat is removed, thus increasing the time before the body's heat sink effect returns the eyelid to normal temperature. The application of force may also assist in expressing the occlusions or obstructions when in a loosened, softened, or melted state from the meibomian glands.

In yet another embodiment, heat can be applied to both the inside and outside of the eyelid to treat MGD. Force can also be applied to the eyelid. As discussed above, the application of force can further assist in obtaining higher temperatures at the meibomian gland and in a shorter period of time and thus more efficiently. The application of force can improve conductive heat transfer efficiency and/or reduce convective heat loss. Any apparatus, device, or tool can be used to apply heat and force to the outside of the eyelid. The application of force may also allow heat to be maintained on the outside of the eyelid for a longer period of time. This is because the application of force may reduce blood flow to the eyelid, thus reducing convective heat loss and increasing conductive heat transfer into the eyelid and to the glands. The heat and/or force applied to the outside of the eyelid can be regulated, as discussed above. The force may be applied during heating, after heating, or both during and after heating. The force can remain after the heat is removed, thus increasing the time before the body's heat sink effect returns the eyelid to normal temperature. The application of force may also assist in expressing the occlusions or obstructions.

Those skilled in the art will appreciate the scope of the present invention and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the invention, and together with the description serve to explain the principles of the invention.

FIGS. 31A and 3B are illustrations of another alternative heat and force application device, according to one embodiment of the present invention;

DETAILED DESCRIPTION OF THE PREFERRED EMBODIMENTS

Figure 1:
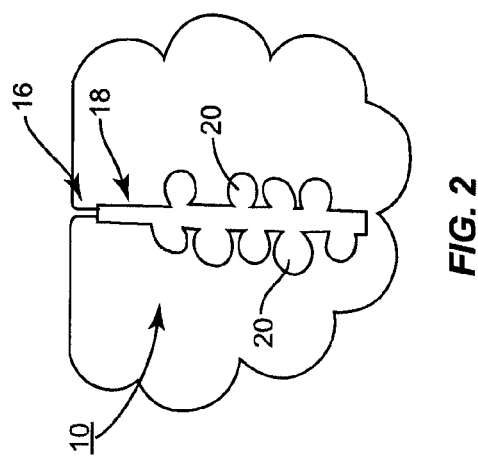
FIG. 1 illustrates an exemplary upper and lower human eyelid showing the meibomian glands.
Figure 2:
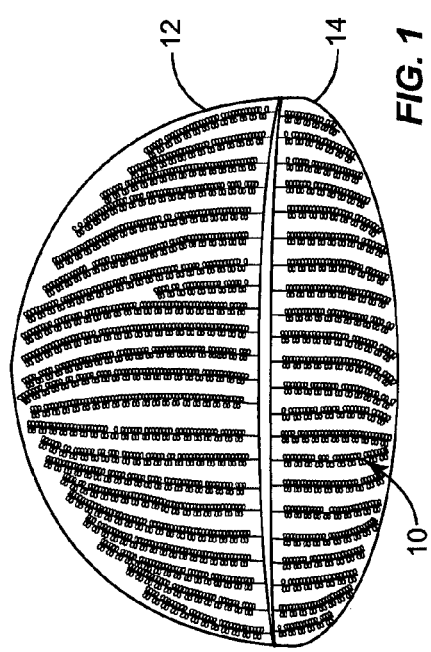
FIG. 2 illustrates an exemplary cutaway view of a meibomian gland.
Figure 3:
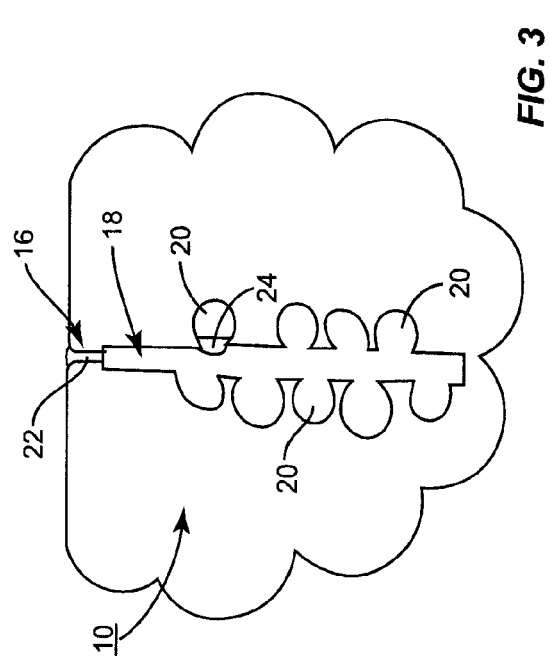
FIG. 3 illustrates an exemplary cutaway view of a meibomian gland having several clogging mechanisms.

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

One embodiment of the present invention includes the breakthrough and previously unknown method of applying heat to the inner surface of the eyelid to treat dry eye caused by meibomian gland dysfunction (MGD). Applying heat to the inside of the eyelid can effectively and efficiently raise the temperature at the meibomian glands to a temperature sufficient to melt, loosen, or soften more serious occlusions or obstructions in the meibomian glands. The occlusions or obstructions can then be physically expressed to improve sebum flow from the meibomian glands to reduce evaporation of the aqueous layer.

Some patients have obstructions or occlusions in their meibomian glands that will not sufficiently melt, loosen, or soften to be expressed without attaining heightened temperatures at the meibomian glands. In many instances, these temperatures either cannot be achieved when applying heat to the outside of the eyelid, or these temperatures may be achievable, but only after applying heat to the outside of the eyelid for a significant period of time. Heightened temperatures may only be achieved by applying heat at unsafe temperatures that would either produce an unacceptable pain response to the patient or damage to the patient's eyelid. This is because of the temperature drop between the outside of the eyelid and the meibomian glands due to conductive heat loss. Heat applied to the outside of the eyelid must conductively travel through the eyelid tissue and through the tarsal plate that encases the meibomian glands inside the eyelid. As an example, it may take twenty to thirty minutes for the temperature at the meibomian glands to reach only a temperature of 41 to 42 degrees Celsius when applying heat to the outside of the eyelid that will not burn or damage the patient's eyelid or surrounding tissue. Temperatures may need to reach between 43 to 45 degrees Celsius, for example, for melting, loosening, or softening of certain obstructions or occlusions in a patient's meibomian glands.

Until the present application, it was only known to apply heat to the outside of the eyelid to treat meibomian gland dysfunction (MGD). Medical professionals would have thought it counterintuitive to apply heat to the inside of the eyelid. It was thought that applying heat to the inside of the eyelid would risk damage to the eyelid or the eyeball itself. Previous studies of heat application to skin showed that damage could occur for temperatures at or above 45 degrees Celsius. These studies were made on external keratinized skin. The tissue on the inner eyelids is non-keratinized epithelium, and as such, is not as well protected from heat as keratinized skin. Thus, one would naturally believe that applying heat to the inside of the eyelid would produce a pain response at lower temperatures than on the outer eyelid surface. However, it has been surprisingly discovered that applying heat to the inside of the eyelid is not only safe, but effective at dislodging obstructions and/or occlusions in the meibomian glands as part of a MGD treatment.

It was hypothesized that heating the inside of the eyelids may provide a more efficient conductive heat transfer to the meibomian glands. Attaining a more efficient heat transfer may allow higher temperatures to be attained at the meibomian glands and in a more efficient time to melt, loosen, or soften more serious obstructions or occlusions in the meibomian glands. The meibomian glands are located closer to the inside surface of the eyelid than the outside surface of the eyelid. Further, there is no tarsal plate located between the inside of the eyelid and the meibomian glands. Thus, it was discovered than conductive heat transfer to the meibomian glands is more efficient when heating the inside of the eyelid. Heat conduction increases with thinner tissue.

In this regard, an experiment was carried out where heat was applied to the inside of the eyelid (and more particularly the palpebral conjunctiva) against traditional notions and known principles. It was discovered that heat could be applied to the inside of the eyelid without damaging the patient's eye if regulated. For example, it was determined that most patients can tolerate a surface temperature of 43-44.5 degrees Celsius without anesthesia and without significant pain. It was found that some patients could tolerate temperatures over 44.5 degrees Celsius without anesthesia. Further, it was discovered than heightened temperatures could be attained and in less time when applying heat to the inside of the eyelid than to the outside of the eyelid due to more effective conductive heat transfer and the proximity to the heating device.

Figure 4:
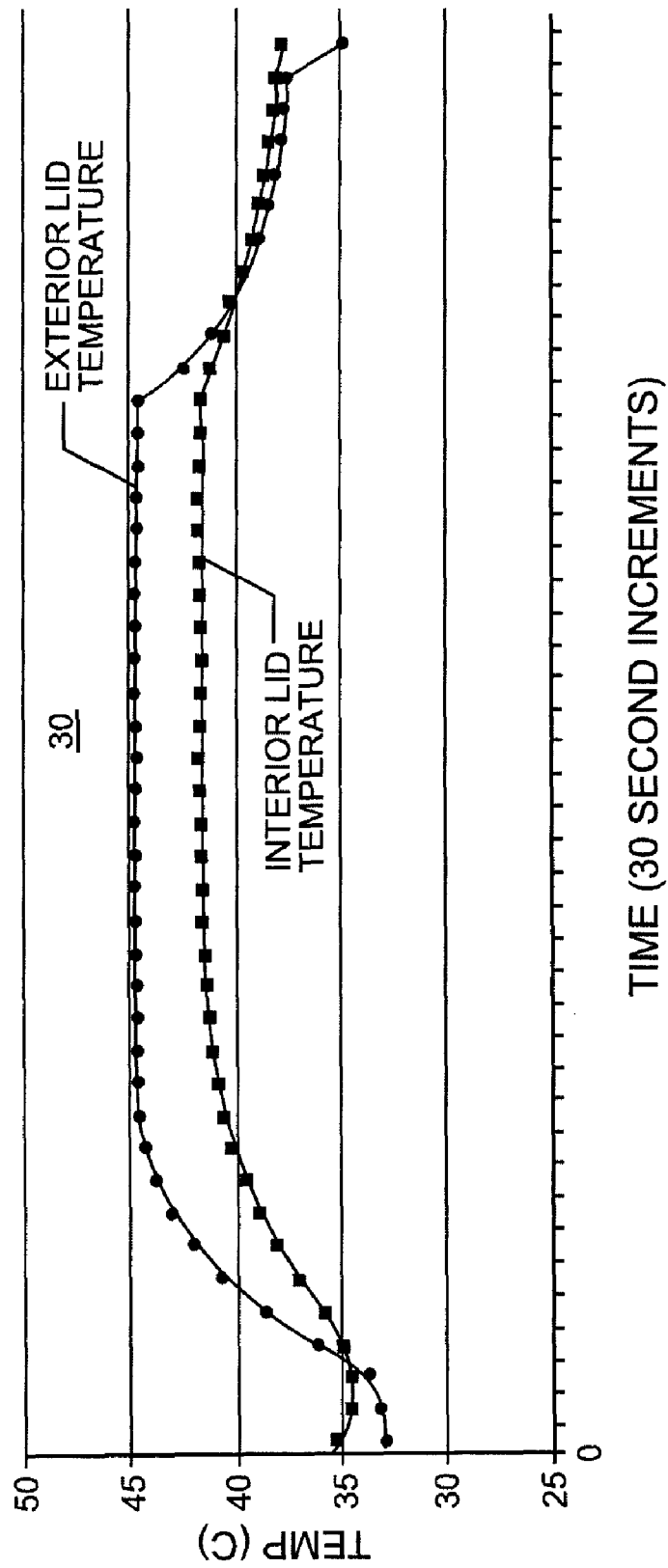
FIG. 4 illustrates an exemplary eyelid temperature profile of an inner and outer eyelid temperature versus time when heat is applied to the exterior of the eyelid.
Figure 5:
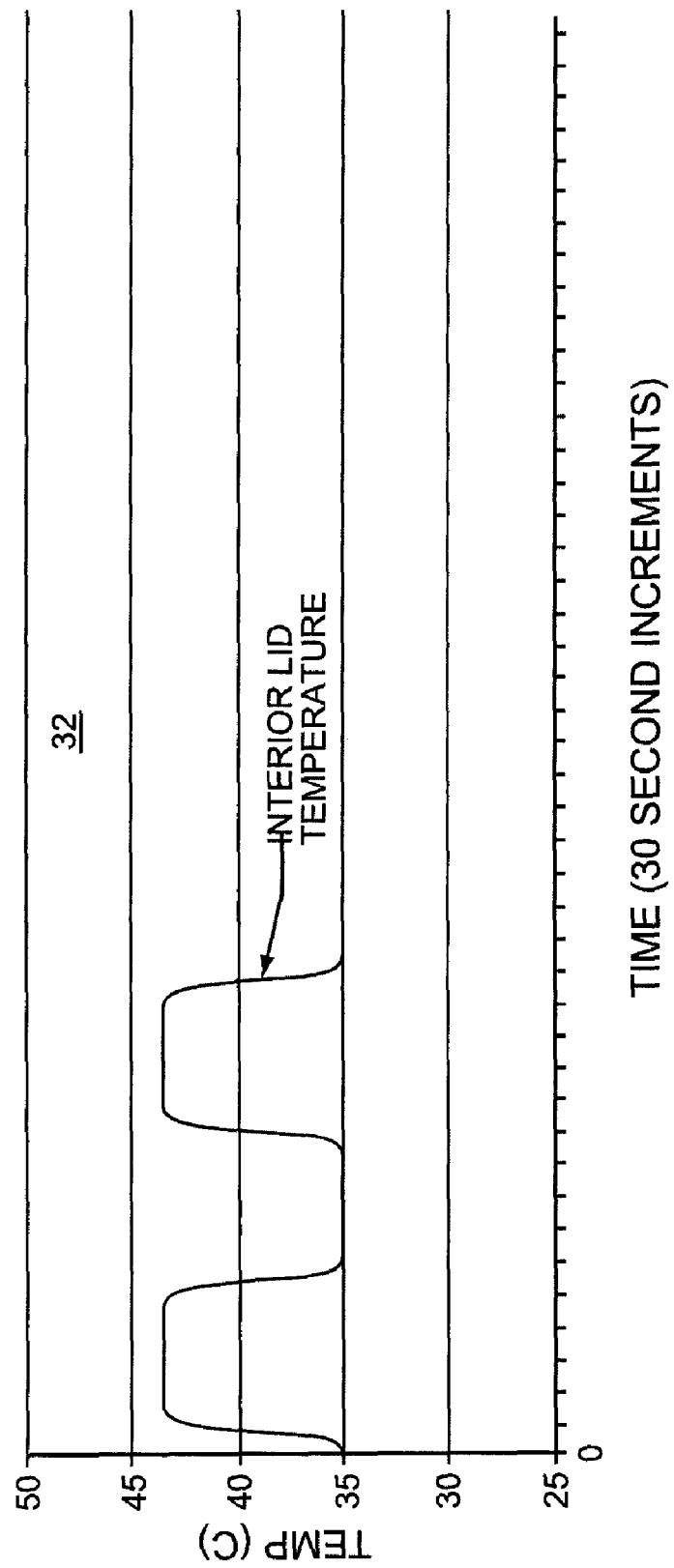
FIG. 5 illustrates an exemplary eyelid lid temperature profile of inside and outside eyelid temperature versus time when heat is applied to the inside the eyelid.

An exemplary lid temperature profile 32 that may be generated when heat is applied to the inside of the eyelid is illustrated in FIG. 5. There, a graph depicts what the temperature of the inner surface of an eyelid may be as a function of time when a source of constant heat is applied to an example subject patient. A heat source attached to the inside of the patient's eyelid is turned on for a period of time. For this patient, it took approximately 30 seconds for the eyelid's inner surface to reach about 44 degrees Celsius. Unlike the lid temperature profile illustrated in FIG. 4, the inner surface of the patient's eyelid did reach a higher temperature when heat was applied to the inside of the eyelid. For example, it may only take two to three minutes to bring the temperature at the meibomian glands to 43-45 degrees Celsius or higher when applying heat to the inside of the eyelid. While not limiting to the present invention, the ability to raise the temperature at the meibomian glands may prove instrumental in melting, loosening, or softening obstructions or occlusions in the meibomian gland to reach the loosening, softening, or melting point of the obstruction or occlusion.

Figure 6:
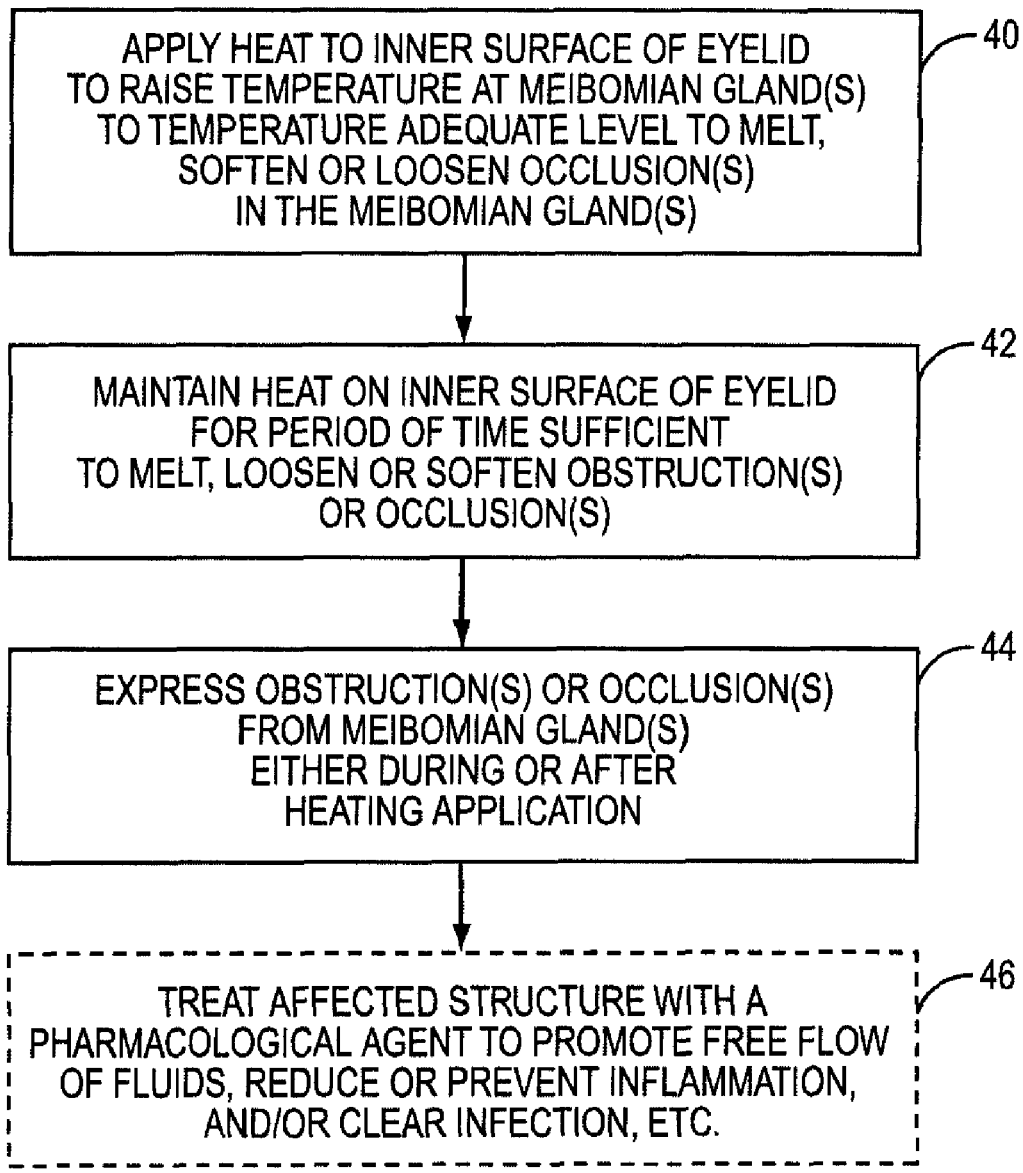
FIG. 6 is a flowchart illustrating an exemplary process of applying heat to the inner eyelid relating to treating meibomian glands.

In this regard, an embodiment of the present invention to apply heat to the inside or inner surface of the eyelid proximate the meibomian glands to treat MGD in basic form is illustrated in the flowchart of FIG. 6. This has the advantage in that it typically takes less time to raise the temperature at the meibomian glands sufficient to melt, loosen, or soften an obstruction or occlusion than if heat were applied directly to the outside of the eyelid. Further, heating the inside of the eyelid may allow higher temperatures to be achieved than if the outside of the eyelid were heated.

First, heat is applied to the inner surface of the eyelid to a temperature adequate to melt, loosen, or soften obstructions or occlusions in the meibomian glands (step 40). For example, heat may be applied to raise the temperature at the inside of the eyelid to 43-47 degrees Celsius, although the present invention is not limited to this temperature range. A time range to apply heat may be a period between 1-10 minutes, and may be limited to a range of 3-6 minutes. The heat may be regulated meaning that a heating means or element is controlled to be within the temperatures and means that are safe for the inner surface of the eyelid and at a sufficient temperature for melting, loosening, or softening an occlusion or obstruction in the meibomian gland. By sufficient temperature, this refers to the amount of heating needed to heat the palpebral conjunctiva to achieve the desired melting, loosening, or softening of the obstruction. The heat may be maintained for a period of time until the temperature reaches the desired level sufficient to melt, loosen, or soften the obstructions or occlusions (step 42). For example, the heat may be applied for 1 to 10 minutes, although the present invention is not limited to any particular amount of heat application time. Thereafter, either during heating or after, obstructions or occlusions in the meibomian glands may be expressed so that sebum flow is restored from the glands to establish a sufficient lipid layer (step 44).

While not limiting to the present invention, the ability to effectively and more efficiently raise the temperature at the meibomian glands may prove instrumental in melting, loosening, or softening obstructions or occlusions in the meibomian gland to reach the loosening or melting point of the obstruction or occlusion.

As used herein, the terms "melt," "loosen," and "soften" and variants thereof are to be interpreted broadly. These terms broadly encompass any change in form or state of the obstructive or occluding material causing or contributing to an obstruction or occlusion related to a disorder of the eye or eyelid structure to a form such that the obstruction or occlusion can be more easily freed or expressed. This includes, but is not limited to, changing form from less of a solid form or state to more of a liquefied form or state, including but not limited to dissolving, loosening, liquefying, and/or softening of the obstructive or occluding material to be removed, and/or dissolving, loosening, liquefying, or softening of material that holds together particulate matters causing or contributing towards the obstruction or occlusion related to a disorder of the eye or eyelid structure and other modalities.

The application of heat may be regulated, meaning that a heating means or element is controlled to be within the temperatures and means that are safe for the inner surface of the eyelid and at a sufficient temperature for melting, loosening, or softening an occlusion or obstruction in the meibomian gland. The heat is maintained for a period of time sufficient to melt, loosen, or soften the occlusions or obstructions. Either during heat application or after heat application is removed, the occlusions or obstructions in the meibomian glands are expressed to remove obstructions or occlusions thus providing an improved pathway to restore or improve sebum flow from the gland.

In one embodiment, increasing the temperature of the surface of the palpebral conjunctiva to at least 37 degrees Celsius can begin to provide therapeutic effect for milder cases of MGD. A therapeutic temperature can be any temperature above body temperature. One preferred range for treatment is 43 to 45 degrees Celsius, with a target of 43 to 44.5 degrees Celsius. A time range to apply heat may be a period between 1-10 minutes, and may be limited to a range of 3-6 minutes. Temperature in this range has been found effective and comfortable to the patient when treating MGD.

In one embodiment, the application of heat may be regulated. Regulated heat can include controlling heat according to a temperature profile. The temperature profile may be a constant temperature, include ramp-ups, ramp-downs, peaks and valleys. Further, the temperature profile may include heat pulses or be modulated with various characteristics, including the use of on/off switching or pulse width modulation (PWM) techniques for example. The use of modulated heat may allow the temperature to be raised even higher at the eyelid without damages to the patient's eyelid since the increased temperatures are applied for shorter periods of time. Obstructions or occlusions in the meibomian glands may have melting, loosening, or softening points that are beyond temperatures that may be applied without the use of modulated heat. The temperature needed to melt, loosen, or soften obstructions or occlusions may depend on how keratinized the obstruction or occlusion is. Not all obstructions or occlusions have the same melting, loosening, or softening points.

By example only, elevated temperatures between 45 and 55 degrees Celsius may be possible when applying regulated heat, especially if the eyelid has been anesthetized. However, heat must always be applied to the eyelid at temperatures that take into consideration the pain response of the patient as well as whether damage will occur to the patient's eyelid and/or surrounding tissues. Depending on the severity of the patient's MGD or the patient's pain tolerance, elevated temperatures may be used with patient's on an individualized basis when applying heat. It has been found that lighter skinned patients can generally tolerate less heat than darker skinned patients, and darker skinned patients tend to exhibit less inflammation as a result of exposure to the heat. Other factors, including humidity, may contribute to a patient's tolerate to greater temperatures. For example, humans can generally tolerate heat up to 70 to 80 degrees Celsius in dry saunas where humidity is low. Application of heat in higher humidity environments may cause pain and/or burns to occur at lower temperatures.

Severe cases of MGD that cause substantial irritation or risk to the patient may even call for temperatures that would produce category one or two burns to the patient's eyelid, since these burns generally heal. Temperatures that cause category three burns should be avoided. In summary, treatment times and/or temperature can be adjusted to account for these differences. The present invention is not limited to any particular temperature or time ranges as long as therapeutic temperature is being applied.

The regulated heat can be maintained at a therapeutic temperature for a treatment period. The treatment period can be approximately 1 to 10 minutes for example. The heat could also be repeatedly applied and maintained for a desired period of time to keep the occlusion or obstruction in a melted, loosened, or softened state. Either during or after such treatment by regulated heat, mechanical expression of lipids and other fluids from the meibomian glands has been found to clear obstructions which have essentially melted or been placed in a suspension state (by virtue of melting materials binding solids together).

Optionally, after expression of the occlusions or obstructions is performed (step 44), an optional pharmacological agent may be applied to the meibomian gland to promote the free flow of sebum and/or reduce or prevent inflammation or infections of the eye or eyelids (step 46). Many pharmacological agents have been proposed for treatment of dry eye syndrome, any of which may be effective or more effective upon clearing of obstructions within the meibomian glands. Some of the pharmacological agents that may be utilized include, but are not limited to: antibiotics such as topical or oral tetracycline and chemically modified tetracycline, testosterone, topical or oral corticosteroids, topical androgens or androgen analogues, omega 3 fatty acid compounds such as fish oils, Laennec, enzymes that promote lipid production, agents that stimulate production of enzymes that promote lipid production, and/or any agent which acts as a secretagogue to enhance meibomian gland secretion or secretion of other tear components. For example, androgen and androgen analogues and TGF-beta have been reported to act as a secretagogue to enhance meibomian gland secretion. These compounds are illustrative examples of appropriate pharmacological agents, but those skilled in the art will appreciate that other pharmacological compounds may be utilized.

Also, agents, such as Restasis (cyclosporine A), that replace or promote production of the tear component may also be applied more effectively after treating the meibomian glands according to the present invention. Treating the meibomian glands improves the lipid layer, thus reducing evaporation and conserving the aqueous layer. Conservation of the aqueous layer reduces the need for tear substitutes to be applied through tear component agents. Thus, tear component agents may not have to be used as often when employing the present invention to treat a patient's MGD.

In the course of experimenting with the application of heat to the inside of the eyelid, it was also discovered that convective heat losses occur due to blood flow in the blood vessels located inside the eyelid. Blood flow through blood vessels located inside the eyelid produces convective heat losses. The blood flow serves as a natural "heat sink" provided by the body. Convective heat loss is lessened when applying heat to the inside of the eyelid than when applying heat to the outside of the eyelid. This is because fewer blood vessels are located between the meibomian glands and the inside of the eyelid than the outside of the eyelid. The meibomian glands are located closer to the inside of the eyelid. However, convective heat loss still occurs when heating the inside of the eyelid. However, if the blood flow were reduced, convective heat losses could be minimized allowing for temperatures to be attained and sustained at the meibomian glands in an even more efficient manner and in less time.

Figure 7:
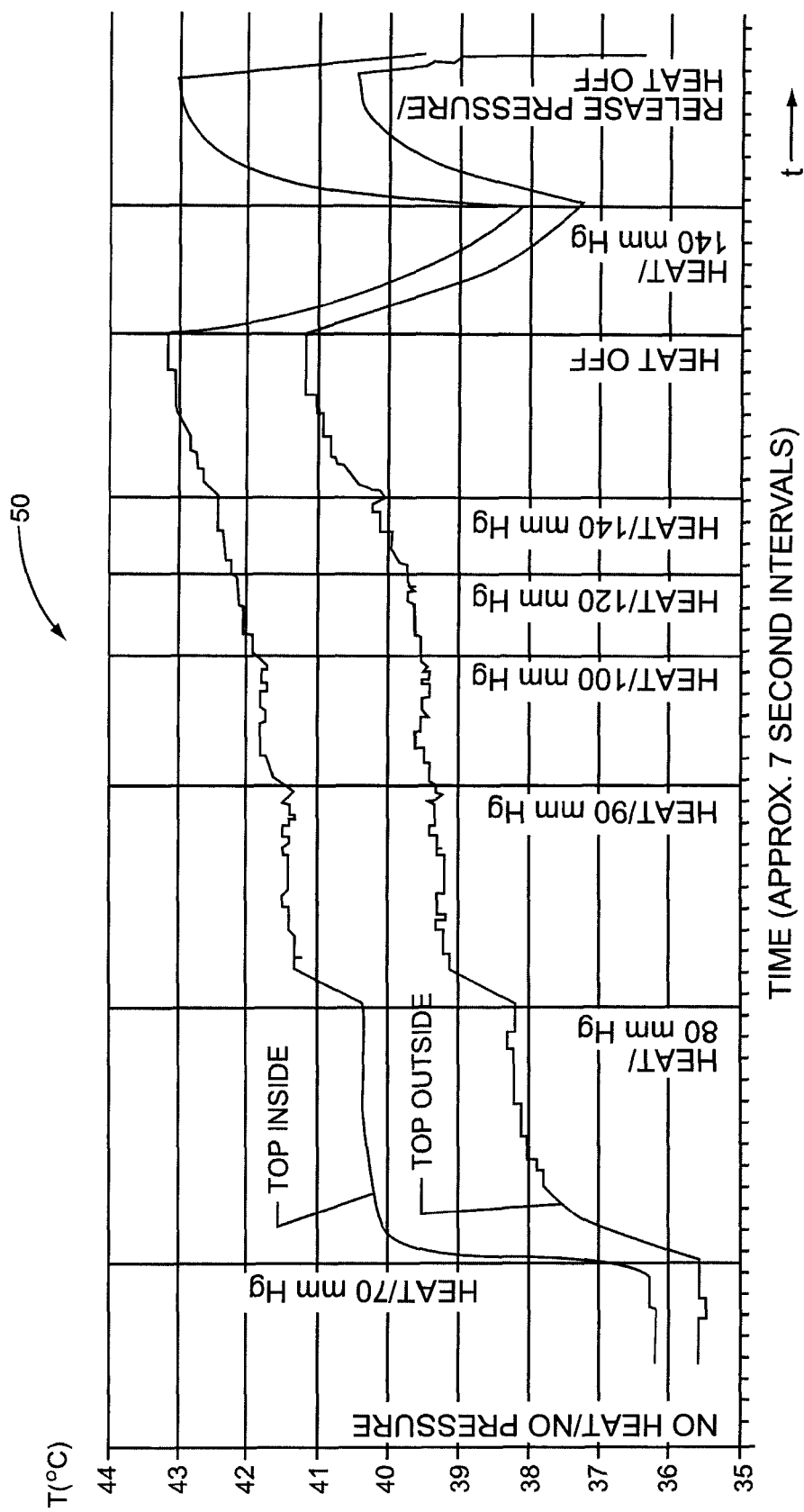
FIG. 7 illustrates an exemplary lid temperature profile of eyelid temperature versus time when heat and force is applied to inside the eyelid.

In this regard, an exemplary lid temperature profile 50 when heat is applied to the inside of the eyelid and force at various pressure levels is applied to the outside of the eyelid is illustrated in FIG. 7. There, a graph depicts the temperature at the inner and outer surface of an eyelid as a function of time when a source of constant heat and pressure is applied to an example subject patient. Initially, no heat or pressure is applied to the eyelid. In this example, the temperature at the inside of the eyelid is approximately 36 degrees Celsius while the temperature at the outside of the eyelid is approximately 35 degrees Celsius. When the heat source is turned on to apply heat to the inside of the eyelid and a 70 mm Hg pressure is applied to the outside of the eyelid, the temperature at the inside of the eyelid dramatically increases quickly. The pressure being applied to the eyelid is reducing blood flow in the eyelid, which reduces convective heat loss and increases conductive heat gain. The temperature at the outside of the eyelid increases quickly as well, but less dramatically than at the inside of the eyelid since the heat source is at the inside of the eyelid. A nominal temperature of approximately 40.5 and 38.3 degrees Celsius is reached at the inside and outside of the eyelid, respectively.

If the pressure is increased, even higher temperatures are attained as illustrated in FIG. 4. Finally, when the heat source is completely shut off, the temperature degrades. However, the temperature at the eyelid does not degrade immediately due to the force continuing to be applied. Again, the force reduces blood flow to prevent convective heat loss. If both heat and force are shut off after being applied, the temperature at the eyelid does degrade more rapidly. This is because blood flow in the eyelid is unobstructed, allowing the body's blow flow to quickly convect the heat away. Thus, the lid temperature profile 50 of FIG. 7 illustrates temperature at the eyelid can be increased effectively and quickly with the application of force in addition to heat. Note that the application of force to reduce convective heat loss can be applied whether heat is applied to the inside or outside of the eyelid. As illustrated in FIG. 7, the application of force is effective in both scenarios.

Thus, one embodiment of the present invention also includes the further application of force to the patient's eyelid in addition to heat. The application of force can further assist in obtaining higher temperatures more efficiently inside the eyelid at the palpebral conjunctiva and at the meibomian gland in a shorter period of time and thus more efficiently. This is because the application of force may reduce blood flow to the eyelid to reduce convective heat loss, as discussed above.

Figure 8:
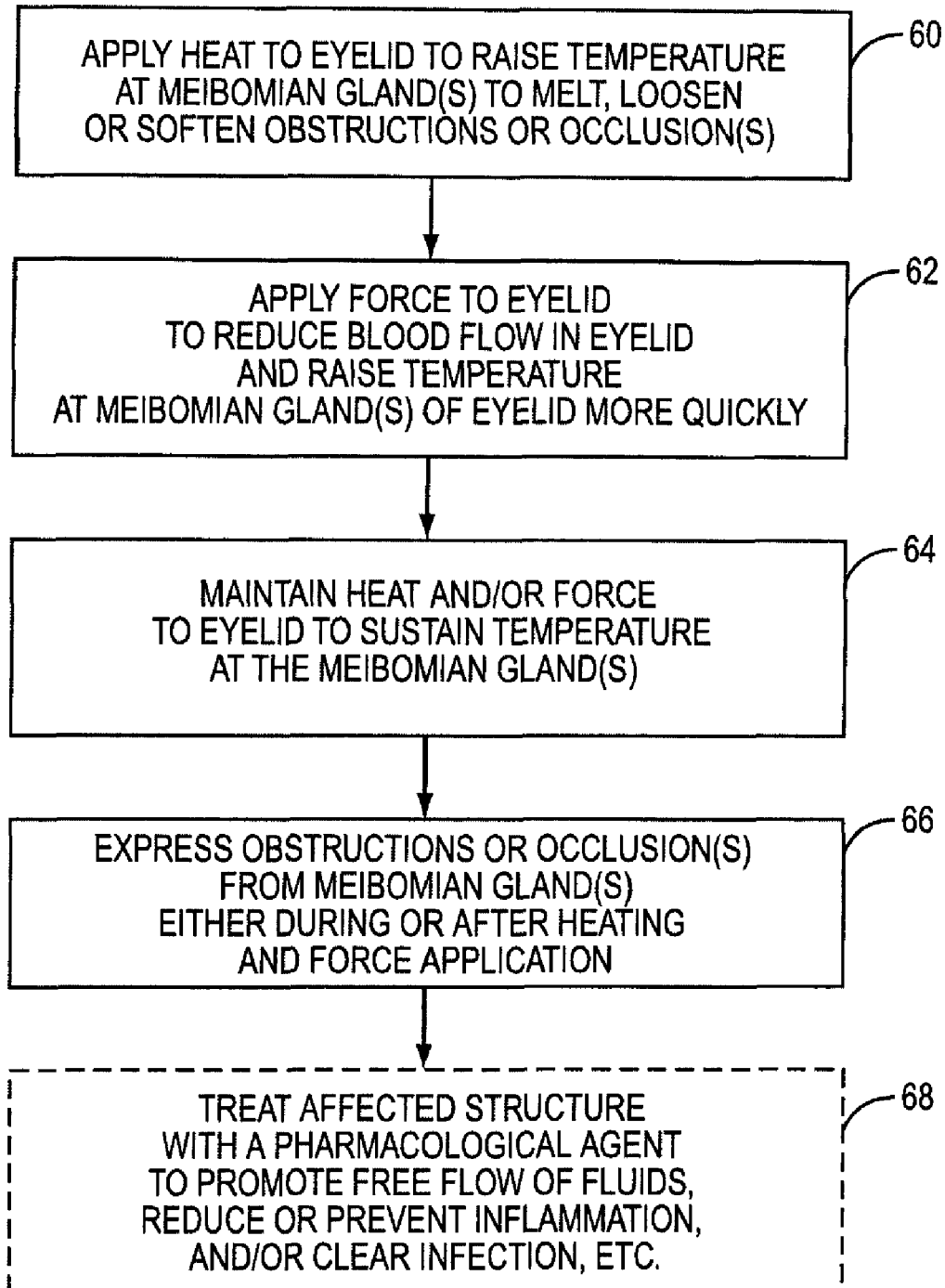
FIG. 8 is a flowchart illustrating an exemplary process of applying heat to the inner eyelid with the addition of force applied to the outside or outer surface of the eyelid relating to treating the meibomian glands.

In this regard, an embodiment of the present invention to apply heat and force to the eyelid to treat MGD is illustrated in the flowchart of FIG. 8. First, heat is applied to the eyelid to raise the temperature at the meibomian glands to the desired level (step 60). For example, heat may be applied to raise the temperature at the inside of the eyelid to 44-47 degrees Celsius. The heat may be applied to the inside or outside of the eyelid, or both sides of the eyelid. The heat may also be regulated, meaning that a heating means or element is controlled to be within the temperatures and means that are safe for the eyelid and at a sufficient temperature for melting, loosening, or softening an occlusion or obstruction in the meibomian gland. A force is also applied to the eyelid to reduce blood flow in the eyelid to allow the applied heat to more quickly raise the temperature at the meibomian glands (step 62). The force may be applied to the inside or outside of the eyelid.

The heat and/or force may be maintained for a period of time sufficient to raise the temperature at the meibomian glands sufficient to melt, loosen, or soften the obstructions or occlusions (step 64). The force may be maintained after heat is removed, or vice versa depending on the treatment technique desired. Maintaining force after heat is removed may cause the temperature at the meibomian glands to dissipate more slowly than if force is removed. Maintaining heat without maintaining force may be employed to allow blood flow in the eyelids, such as between successive treatments. For example, it may be desirable to maintain heat to lessen the total amount of treatment time while applying and removing force between treatments. Also, it may not be necessary to apply significant amounts of force or for the same duration as heat if the obstruction or occlusion is located in close proximity to the lid margin rather than in the deeper portions of the meibomian gland.

Applying force can also result in a more efficient conductive heat transfer from an applied heat source, because the pressure created by the force causes the heat source to be compressed against the tissue of the eyelid. This compression can have several benefits. Compression spreads out the tissue to which heating is applied thus making it thinner and improving conductive heat transfer. Compression can also "squeeze out" air pockets at the surface of the eyelid due to the microscopic roughness of skin. Thus, compression of the heat source against the eyelid increases the surface contact between the heat source and the surface of the eyelid (which increases the heat transfer equation) to provide a more effective conductive heat transfer to the meibomian glands. This results in the meibomian glands being heated to the desired temperature level in a shorter period of time due to these gained efficiencies. Further, increased temperatures may be attained that may not have otherwise been obtained, or obtained using less heat or thermal energy. Because the heating is located in close proximity to the eyelid surface and heating is further compressed against the eyelid surface, heat transfer is very efficient providing for the temperature at the surface of the eyelid to be very close to the temperature at the meiboimian glands.

Further, note that while the exact reduction in times to heat the meibomian glands will vary from patient to patient when force is applied, and may be based on the amount of pressure applied to the patient's eyelid, in general, the change in heating times can vary by as much as several hundred percent, for example, when compared to previous methods. As an example, this can translate into five (5) or more minutes that one has to expel an obstruction or occlusion before such re-solidifies when compared with prior methods.

The force may be regulated, meaning that a force generating means is controlled to be within the pressure ranges that are safe to be applied to the eyelid and at sufficient pressure to allow the temperature at the meibomian gland to be raised sufficiently. The force can also be a constant force and be provided manually. For example, force may be provided by a technician or doctor's finger or thumb as heat is applied. The force may be applied during heating, after heating, or both during and after heating. In either case, the force may assist in expressing occlusions or obstructions when in a loosened, softened, or melted state from the meibomian glands. The force may include vibratory type forces, including those generated mechanically or those using fluid type devices or mechanisms. The force can be applied at a particular location or vector of the patient's eyelid to be specifically directed to the meibomian glands. This may reduce the level of force needed to express obstructions or occlusions in the glands. The level of force needed to express obstructions or occlusions in the glands may also be greatly reduced when heat is applied to the obstructions or occlusions to place them in a melted, softened, or loosened state.

The application of force can also stimulate the movement of fluids or suspensions of occlusions or obstructions from the glands. The present invention can be used with devices which generally apply a regulated force or milking action to the eyelid to express the fluids or suspensions or to otherwise mechanically stimulate the movement of fluids from the glands. In some instances, a small, gentle, continuous force applied to the eyelid will assist in expression of the fluids and suspensions. Vibration can also be used when applying force simultaneously or immediately after the heating to further assist in the expression.

Thereafter, either during heating and/or the application of force or after either, obstructions or occlusions in the meibomian glands may be expressed so that sebum flow is restored from the glands to establish a sufficient lipid layer (step 66).

Just as discussed above in the flowchart of FIG. 6 where only heat is applied, the application of heat may be regulated. Regulated heat can include controlling heat according to a temperature profile. The temperature profile may be a constant temperature, include ramp-ups, ramp-downs, peaks and valleys. Further, the temperature profile may include heat pulses or be modulated with various characteristics, including the use of on/off switching or pulse width modulation (PWM) techniques for example. The use of modulated heat may allow the temperature to be raised even higher at the eyelid without damages to the patient's eyelid since the increased temperatures are applied for shorter periods of time. Obstructions or occlusions in the meibomian glands may have melting, loosening, or softening points that are beyond temperatures that may be applied without the use of modulated heat. The temperature needed to melt, loosen, or soften obstructions or occlusions may depend on how keratinized the obstruction or occlusion is. Not all obstructions or occlusions have the same melting, loosening, or softening points.

By example only, elevated temperatures between 45 and 55 degrees Celsius may be possible when applying regulated heat, especially if the eyelid has been anesthetized. However, heat must always be applied to the eyelid at temperatures that take into consideration the pain response of the patient as well as whether damage will occur to the patient's eyelid and/or surrounding tissues. Depending on the severity of the patient's MGD or the patient's pain tolerance, elevated temperatures may be used with patient's on an individualized basis when applying heat. It has been found that lighter skinned patients can generally tolerate less heat than darker skinned patients, and darker skinned patients tend to exhibit less inflammation as a result of exposure to the heat. Other factors, including humidity, may contribute to a patient's toleranc of greater temperatures. For example, humans can generally tolerate heat up to 70 to 80 degrees Celsius in dry saunas where humidity is low. Application of heat in higher humidity environments may cause pain and/or burns to occur at lower temperatures.

Severe cases of MGD that cause substantial irritation or risk to the patient may even call for temperatures that would produce category one or two burns to the patient's eyelid, since these burns generally heal. Temperatures that cause category three burns should be avoided. In summary, treatment times and/or temperature can be adjusted to account for these differences. The present invention is not limited to any particular temperature or time ranges as long as therapeutic temperature is being applied.

The regulated heat can be maintained at a therapeutic temperature for a treatment period. The treatment period can be approximately 1 to 10 minutes for example. The heat could also be repeatedly applied and maintained for a desired period of time to keep the occlusion or obstruction in a melted, loosened, or softened state. Either during or after such treatment by regulated heat, mechanical expression of lipids and other fluids from the meibomian glands has been found to clear obstructions which have essentially melted or been placed in a suspension state (by virtue of melting materials binding solids together).

Optionally, after expression of the occlusions or obstructions is performed (step 66), an optional pharmacological agent may be applied to the meibomian gland to promote the free flow of sebum and/or reduce or prevent inflammation or infections of the eye or eyelids (step 68). The discussion regarding use of pharmacological agents above for the flowchart in FIG. 6 is equally applicable for this embodiment and thus will not be repeated here. Those compounds are illustrative examples of appropriate pharmacological agents, but those skilled in the art will appreciate that other pharmacological compounds may be utilized.

In one embodiment, a force can be applied to the outside of the eyelid while heat is applied to the inside of the eyelid to treat MGD. The heating of the inner surface of the upper or lower eyelid can be done by any convenient method. The lids can be heated one at a time or both at once, depending on the time available to remove the occlusions once heated. One device for heating the palpebral conjunctiva is illustrated in FIGS. 9-14.

Figure 9:
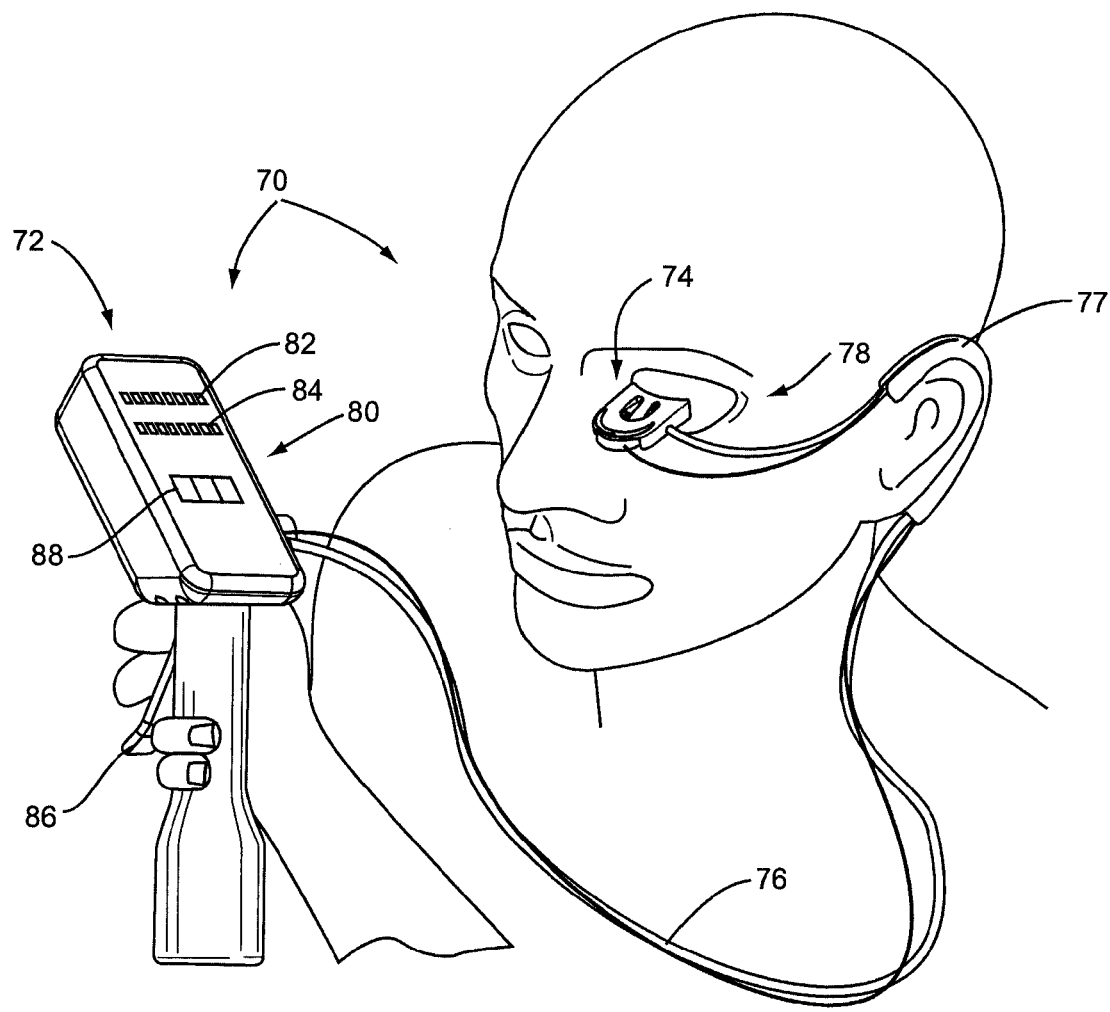
FIG. 9 illustrates a heat and force application device according to one embodiment relating to the present invention to facilitate the application of heat to the inside and force to the outside of a patient's eyelid relating to treating meibomian glands.

FIG. 9 illustrates the overall device referred to as a heat and force application device 70. In this embodiment, the heat and force application device 70 consists of a hand-held, battery-operated controller 72 that contains heat and pressure generating and regulation components. The controller 72 can also be a non hand-held device that is either mounted or rests on a table top, for example. The controller 72 as described herein is intended to describe and encompass any device, including but not limited to electronic and pneumatic controls and supporting components, that is adapted to allow and control the application of heat and/or force to the patient's eyelid. The controller 72 is connected to a disposable component 74, via a controller interface 76, to generate heat and force at an eyelid 78, as illustrated in FIG. 9. The disposable component 74 consists of a lid warmer 90 provided in the form of a lens (illustrated in FIGS. 10-12) that applies heat to the inside of the patent's eyelid and interfaces with an eye cup to apply force to the outside of the patient's eyelid (illustrated in FIGS. 13-14). Both can be used in concert to treat MGD for a single eye. The interface 76 tubing can be wrapped around the patient's ear 77 with any excess clipped to the patient's clothing. The heat and force application device 70 is intended for use by physicians to apply localized heat and pressure therapy for treating MGD.

The controller 72 contains a user interface 80 to allow a physician or other technician to control the heat and force application device 70. Temperature and pressure being applied to the patient's eyelid 78 can be seen on a temperature display 82 and a pressure display 84. By observing temperature and pressure displays 82, 84, the physician can determine when a therapeutic temperature and pressure have been reached. For example, the temperature and pressure displays 82, 84 may be segment bar graphs so that both the temperature and pressure levels and the increasing or decreasing nature of the temperature and pressure levels can be seen. The temperature level to be reached at the patient's eyelid can either be set to a static level within the controller 72, or controllable by a physician or technician. The force and thus the pressure applied to the patient's eyelid is controllable by squeezing a force lever 86. When a physician or technician desires to apply force, the force lever 86 can be squeezed. To release force and thus reduce pressure, the force lever 86 is disengaged. The pressure created by the force applied to the patient's eyelid is displayed on the pressure display 84.

A timer display 88 can be provided on the controller 72 to display the amount of time that heat and/or force has been applied to the patient's eyelid 78. The timer display 88 can display a cumulative amount of time passed or provide a countdown timer if an initial duration is set. For example, the timer display 88 may be comprised of a number of seven segment displays. In one embodiment, the timer display 88 will count down from one hundred eighty (180) seconds and will flash at one hundred twenty (120) seconds and sixty (60) seconds, which is an indicator to the physician to release the force lever 86 and then reapply force and pressure by squeezing the lever 86 again.

Figure 10:
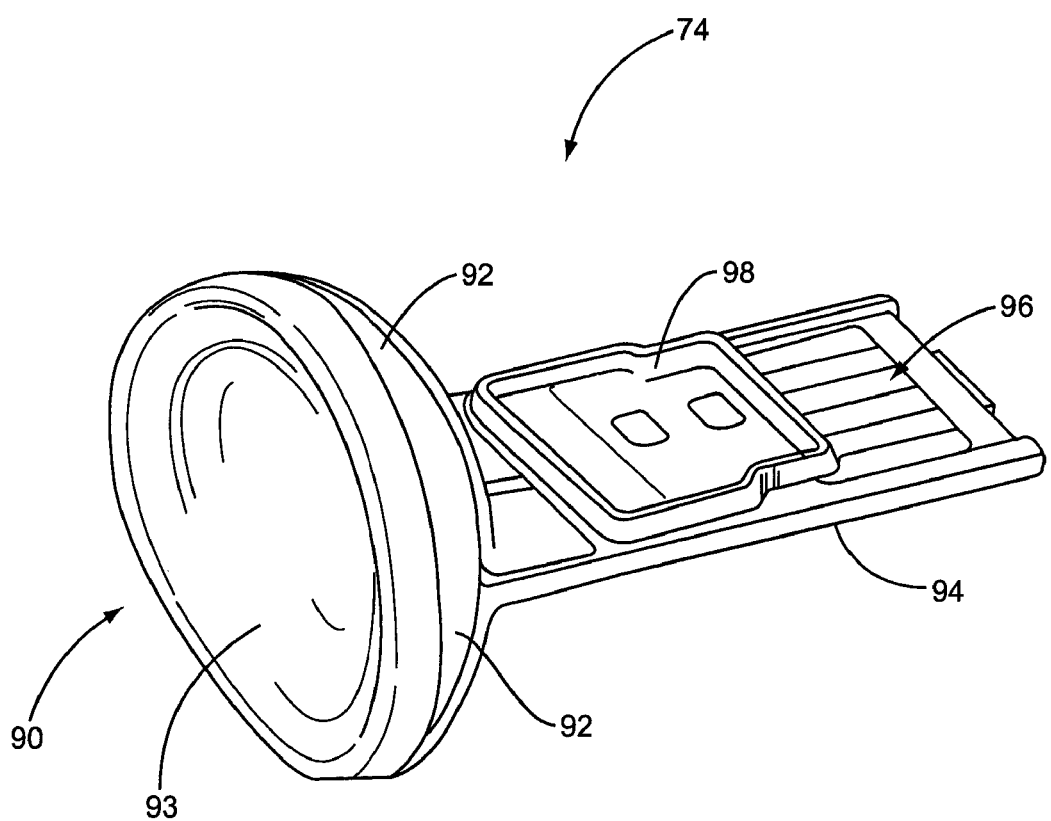
FIG. 10 illustrates a lid warmer component of the heat and force application device illustrated in FIG. 9, which is adapted to fit onto a patient's eye to controllably deliver heat to the inside of the patient's eyelid, according to one embodiment relating to the present invention.
Figure 11:
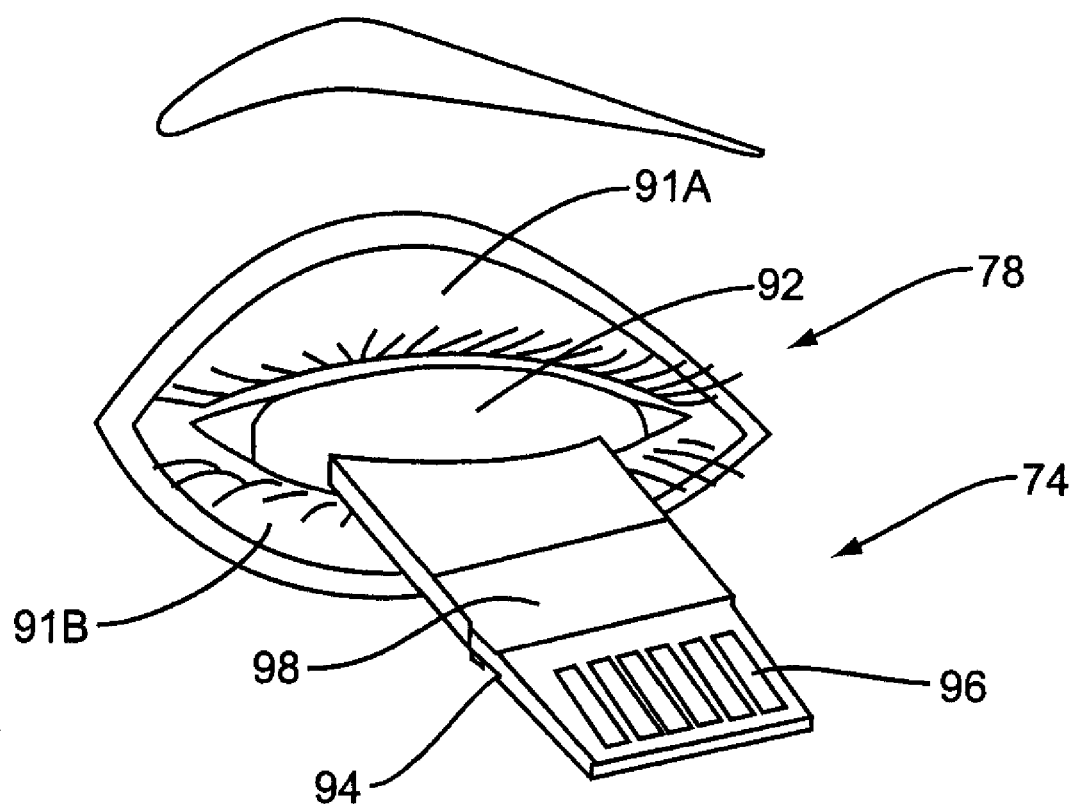
FIG. 11 illustrates the process of placing the lid warmer on the patient's eye inside the eyelid to install the heat application device onto a patient's eye for treating the meibomian glands, according to one embodiment relating to the present invention.

FIG. 10 illustrates the disposable component 74 in more detail. The disposable component 74 consists of a lid warmer 90 that includes a lens in the disclosed embodiment. The lens 90 contains a heating element to apply heat to a patient's eyelids 91A, 91B, but also provides an insulating back plate against which force may be applied. As illustrated in FIG. 11, the lens 90 is placed on the patient's eye with the patient's upper and lower eyelids 91A, 91B resting on the outside surface of the lens 92. Before installation, the scleral side of lens 90 may be lubricated with saline, or equivalent lubricating drops. The lens 90 is then inserted onto the patient's eye under the eyelids 91A, 91B. A heating element (not shown) is contained within the lens 90 that can apply heat to the inside of the patient's eyelid when installed. The material used to construct the lens 90 is not electrically conductive, but is thermally conductive to allow heat from the heating element inside to be transferred to the patient's eyelid. The lens 90 can be constructed out of a plastic, including a clear plastic such as LEXAN HPS2 for example. Further, the lens 90 can be constructed from a biocompatible material, such as polymethylmethacrylate (PMMA), epoxy, or other materials well known to those skilled in the art. The lens 90 may be flexible, but ideally should be only minimally compressible to fit against the patient's eyeball.

The lens 90 also contains a lid warmer platform or tab 94 that is attached to the lens 90. The lid warmer platform 94 may be connected perpendicularly to the lens 90 such that it extends away from the patient's eye when installed. The lid warmer platform 94 provides several benefits. First, provides a handle for insertion and movement or adjustment of the lens 90 and its heating element. Second, it provides a guide post for a compression force device to attach to apply a force to the patient's eyelid while the lens 90 applies heat to the inside of the patient's eyelid. It can also support a lens electrical interface 96 to allow the lens 90 to electrically connect the heating element inside the lens 90 to the controller 72 via the interface 76. The controller 72 can then apply electrical energy to the heating element to generate heat within the lens 90 and thus to the inside of the patient's eyelid when installed. Second, it provides a support structure for interface circuitry 98. The interface circuitry 98 provides electrical connections for energizing the heating element and communicating temperature measured at the lens 90 back to the controller 72 for heat regulation. The interface circuitry 98 will discussed later in this application and in regard to FIG. 16.

Figure 12:
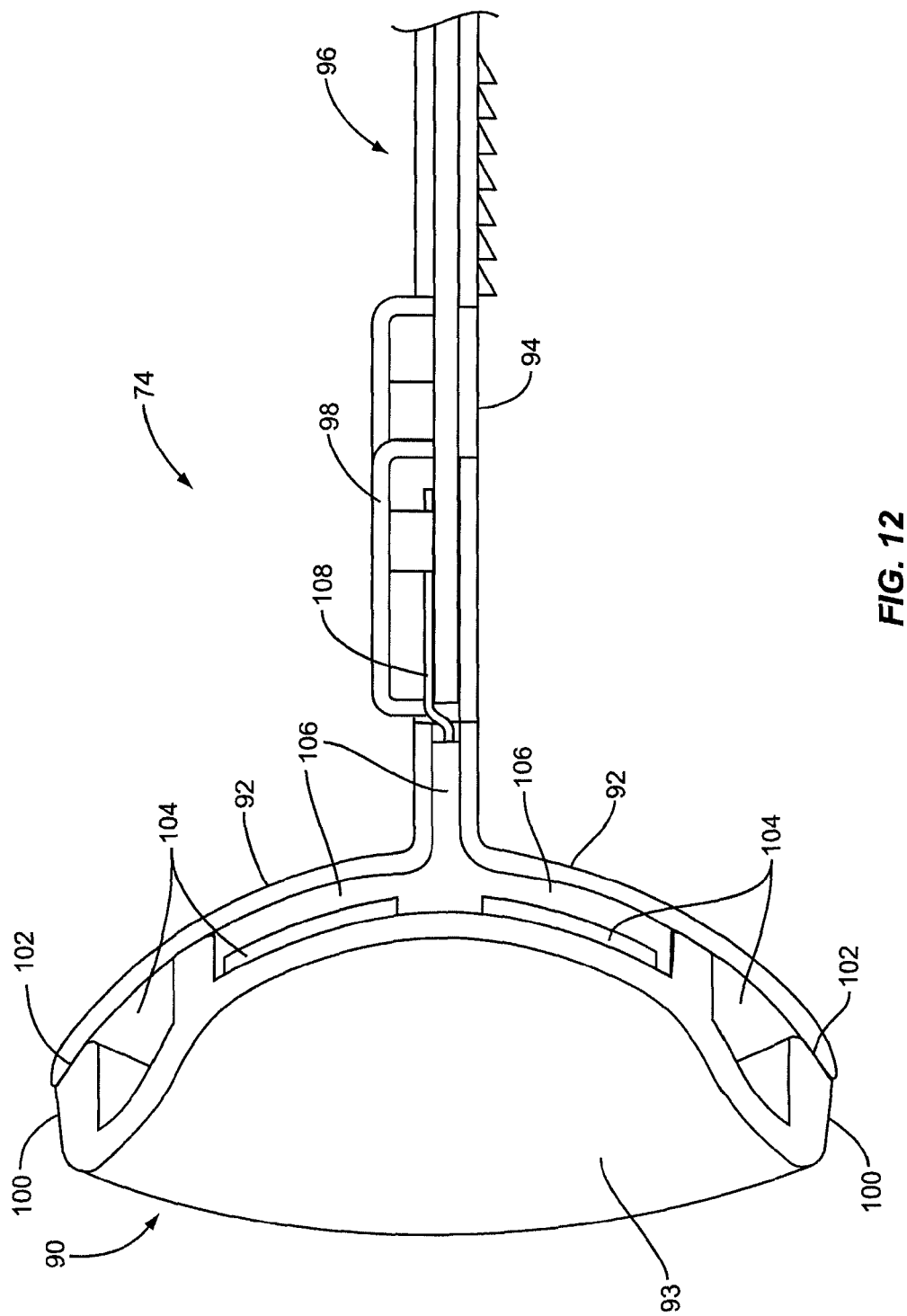
FIG. 12 illustrates a cross-sectional view of the lid warmer illustrated in FIGS. 9-11 to further illustrate heat delivery components and features of the lid warmer, according to one embodiment relating to the present invention.

FIG. 12 illustrates a cross-sectional view of the lid warmer employing the lens 90 illustrated in FIGS. 9-11 to further illustrate heat delivery components and features of the lid warmer, according to one embodiment of the present invention. The lens 90 is formed by a scleral side 93 being attached to an eyelid side 92. The scleral side 93 of the lens 90 contains a bend 100 around its circumference edge to provide an attachment edge 102 to support attachment of the eyelid side 92. Because of the bend 100, a hollow chamber 104 is formed inside the lens 90. The hollow chamber 104 supports a heating element 106 contained inside the lens 90 to generate heat when energized. The heating element 106 abuts against the eyelid side 92 of the lens 90 so that the heat generated is located adjacent the inner eyelid to apply heat to the meibomian glands. The heating element 106 is attached to the interface circuitry 98 via a fused link 108, which is then attached to the controller 72 via the lid warmer platform 94 being attached to the controller interface 76. In this manner, the controller 72 can cause the heating element 106 inside the lens 90 to generate heat by applying an electrical signal to the interface circuitry 98 which is connected to the heating element 106. If the temperature exceeds the threshold temperature level of the fused link 108, the link 108 would melt and create an open circuit to disable the heating element 106 for safety reasons. Alternatively, the fused link 108 could be a thermal link provided as an integrated part of the heating element such that the fused link 108 would melt and create an open circuit at a given threshold temperature.

The heating element 106 may be provided in any form or material. The heating element 106 may be a resistive type heater, a thick film heater, or any one of a number of other types, such as a "flex circuit" (etched metal on flexible substrate) well known to those skilled in the art. The heating element 106 can be formed to the shape of the lens 90. In the illustrated example, the heating element 106 is a material that is both electrically and thermally conductive. This may be important. The electrical conductivity characteristic allows current to be applied to the heating element 106 to generate resistive heat. The thermal conductivity characteristic serves to evenly distributes the resistive heat over the entire heating element 106 to more evenly distribute the heat to the patient's eyelid. Without these characteristics, it may be more difficult to regulate heat generated by the heating element to efficiently and effectively melt, loosen, or soften obstructions or occlusions in the meibomian glands. Examples include the E5101 carbon-loaded polyphenylene sulfide and the E2 liquid crystal polymer, both manufactured by Cool Polymers, Inc.

The size of the lens 90 may also play a part in the heating element 106 selection and the amount of heat it must generate to be effective in MGD treatment. The lens 90 distributes heat generated by the heating element 106. A larger lens 90 may distribute the heat generated by the heating element 106 more uniformly and over a larger surface area. Also note that the application of heat to the patient's eyelid does not necessarily have to include an embedded heating element 106 in the lens 90. Heat application may be provided as part of the environment, such as air for example. The amount of heat applied, the temperature reached at the meibomian glands as a result, where the heat is applied on the patient's eyelid or surrounding tissue, and the duration of heat applied can control the selection of the heating source.

In addition to the insulation provided by the material used to construct the lens 90, the lens 90 may also contain an integrated insulator inside the chamber 104 as an additional measure of insulation. Insulation prevents substantial heat from reaching the eyeball and thus protects the cornea and sclera. As employed herein, the term "insulate" or "insulation" is intended to include any component or material and/or specific geometries of components or materials, wherein there is greater resistance to thermal conduction or radiation towards the surface of the eye than towards the eyelid. Stated alternatively, in the insulator thermal energy radiates more easily towards the eyelid 91A, 91B than towards the eyeball surface in order to minimize the possibility of causing injury to the eyeball. In the lens 90 example of FIG. 12, the integrated insulator is air and is formed by the natural gap that exists by the space left by the heating element 106 not filling up the entire volume of the chamber 104. The heating element 106 is biased according to its location in the lens 90, and in particular to be located behind the integrated insulator, to produce more heat on the insides of the patient's eyelid than on their eyeball.

Figure 13A:
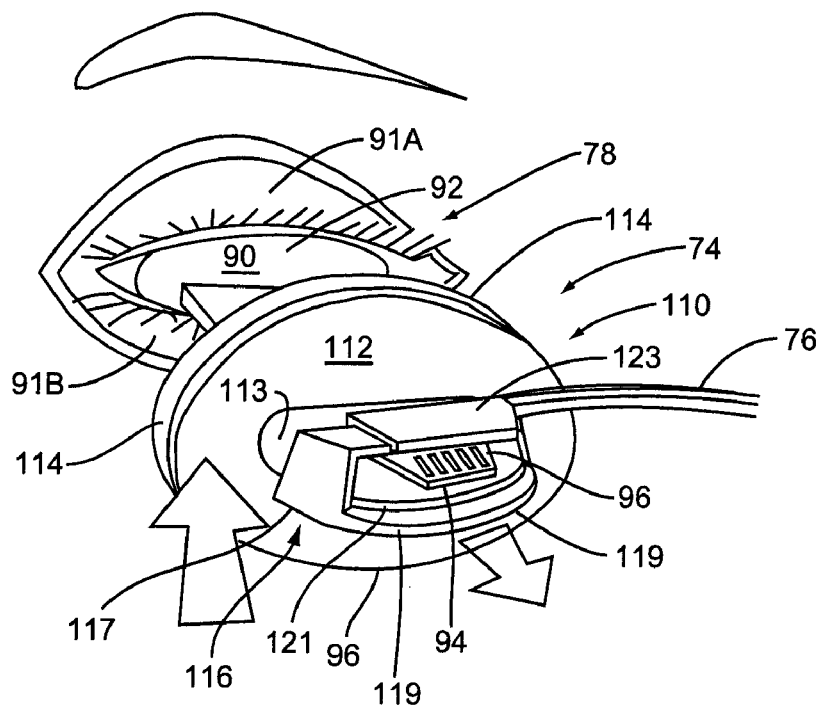
FIGS. 13A and 13B illustrate embodiments of a lid warmer and eyecup heat and force application device for securing the eyecup to the lid warmer as part of installing the force application device onto a patient's eye for treating the meibomian glands.

FIG. 13A illustrates an eyecup 110 that is adapted to allow the controller 72 to apply a force to the patient's eyelids 91A, 91B in addition to heat. The eyecup 110 is a curved carrier 112 that supports an inflatable bladder 114. The inflatable bladder 114 is attached to the curved carrier 112. The inflatable bladder 114 is then connected to the controller 72 via a tubing 118 in the controller interface 76 (see FIG. 14) such that the controller 72 can pump air into the tubing 118 to inflate the inflatable bladder 114. When inflated, the eyecup 110 applies force to the outside of the eyelid 91A, 91B while heat can be applied via the lens 90 and heating element 106. To apply force to the patient's eyelids 91A, 91B, the bladder 114 is inflated under control of the controller 72. To release the force and thus reduce pressure, the air in the bladder 114 is released by the controller 72.

When desired to be used, the lid warmer platform 94 is inserted into an eyecup orifice or slot 113 in the eyecup 110 between a latching mechanism 116. The latching mechanism 116 provides a means to secure the lid warmer platform 94 to the eyecup 110 when in use as well as provide an interface to electrically connect the lid warmer electrical interface 96 to the controller 72 via the controller interface 76. The latching mechanism 116 is comprised of a carrier 117 having a semi-circular carrier base 119. The carrier base 119 receives an eyecup platform 121 attached to the eyecup 110. The carrier base 119 and eyecup platform 121 can be squeezed together like a clip to control an opening through which the lid warmer platform 94 is inserted into the carrier 117 when inserted into the orifice 113 of the eyecup 110. When the carrier base 119 is not squeezed against the eyecup platform 121, the carrier opening through which the lid warmer platform 94 is inserted closes to secure the lid warmer platform 94 to the carrier 117, and thus the eyecup 110. The eyecup platform 119 is adapted to allow the lid warmer platform 94 to rest on top when inserted into the eyecup orifice 113. When inserted, the electrical interface 96 of the lid warmer 74 contacts a carrier interface 123, which provides an electrical connection between the electrical interface 96 and the controller interface 76.

Figure 13B:
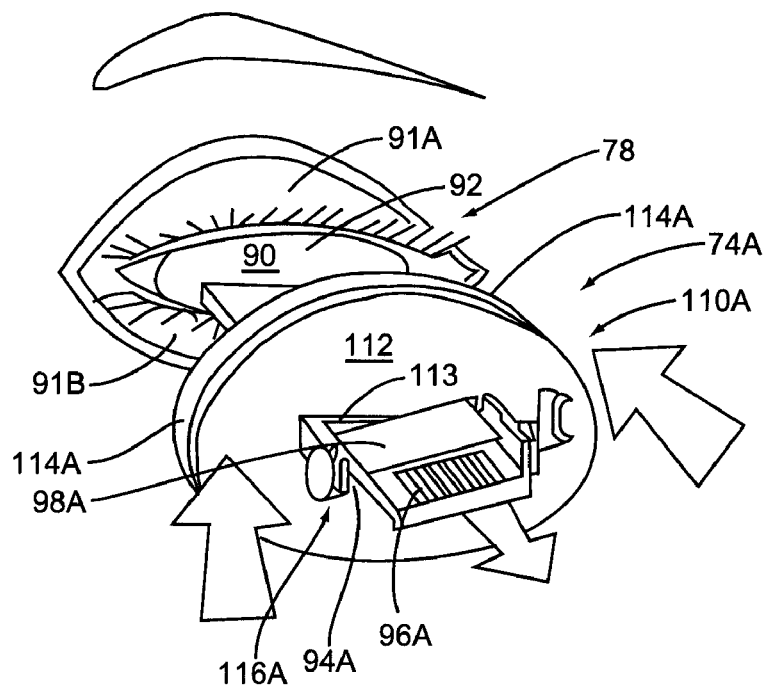

FIG. 13B illustrates an alternative latching mechanism 116A to one illustrated in FIG. 13A. The latching mechanism 116 is compressed in the horizontal plane while the eyecup 110 is moved forward along the lid warmer tab 94 until it rests against the outside of the patient's eyelids 91A, 91B. When the latching mechanism 116 is released, the eyecup 110 is fixed in place in its location along the lid warmer tab 94. In this manner, the patient's eyelids 91A, 91B are "sandwiched" between the lens 90 and the eyecup 110. More information and detail regarding the latching mechanism 116 is illustrated in FIGS. 27-30 and will be described later in this application.

Figure 14:
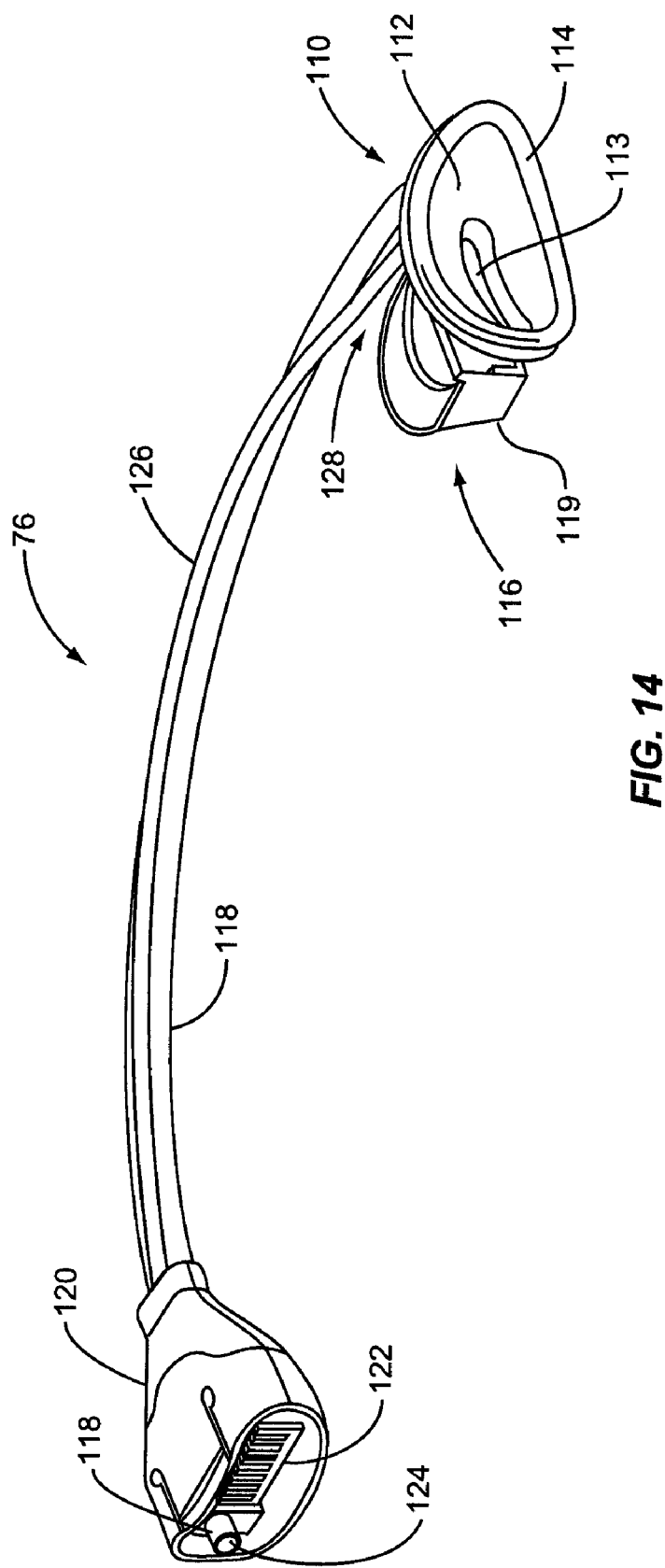
FIG. 14 illustrates an interface adapted to be attached between the eyecup and the controller of FIGS. 9-13B for facilitating selective and controllable communication of heat and/or force to the eyelid, according to one embodiment of the present invention.

FIG. 14 illustrates more detail regarding the controller interface 76. The controller interface 76 couples the controller 72 to the lens 90 and eyecup 110 to allow the controller 72 to controllably apply heat and/or force to the patient's eyelid as part of a MGD treatment. The controller interface 76 contains a connector 120 on one end that connects to the controller 72. The connector 120 includes both an electrical interface 122 and a pneumatic interface 124. The electrical interface 122 allows the controller 72 to send and receive electrical signals over an electronics wiring 126 to and from the lid warmer 90, as will be described in more detail below. The electronics wiring 126 interfaces with an eyecup electrical connector 128 on the eyecup 110 such that the lid warmer electrical interface 96 of the lid warmer 90 is connected to the electronics wiring 126 when the lid warmer platform 94 is inserted into the eyecup 110, as illustrated in the examples of FIGS. 13A and 13B. The pneumatic interface 124 allows the controller 72 to pump into the tubing 118 to inflate the inflatable bladder 114 on the eyecup 110 to apply force to the patient's eye and to deflate the air in the inflatable bladder 114 to release force and relieve pressure. In the illustrated embodiment, the pneumatic interface 124 is securely coupled to the inflatable bladder 114 on the eyecup 110.

Figure 15:
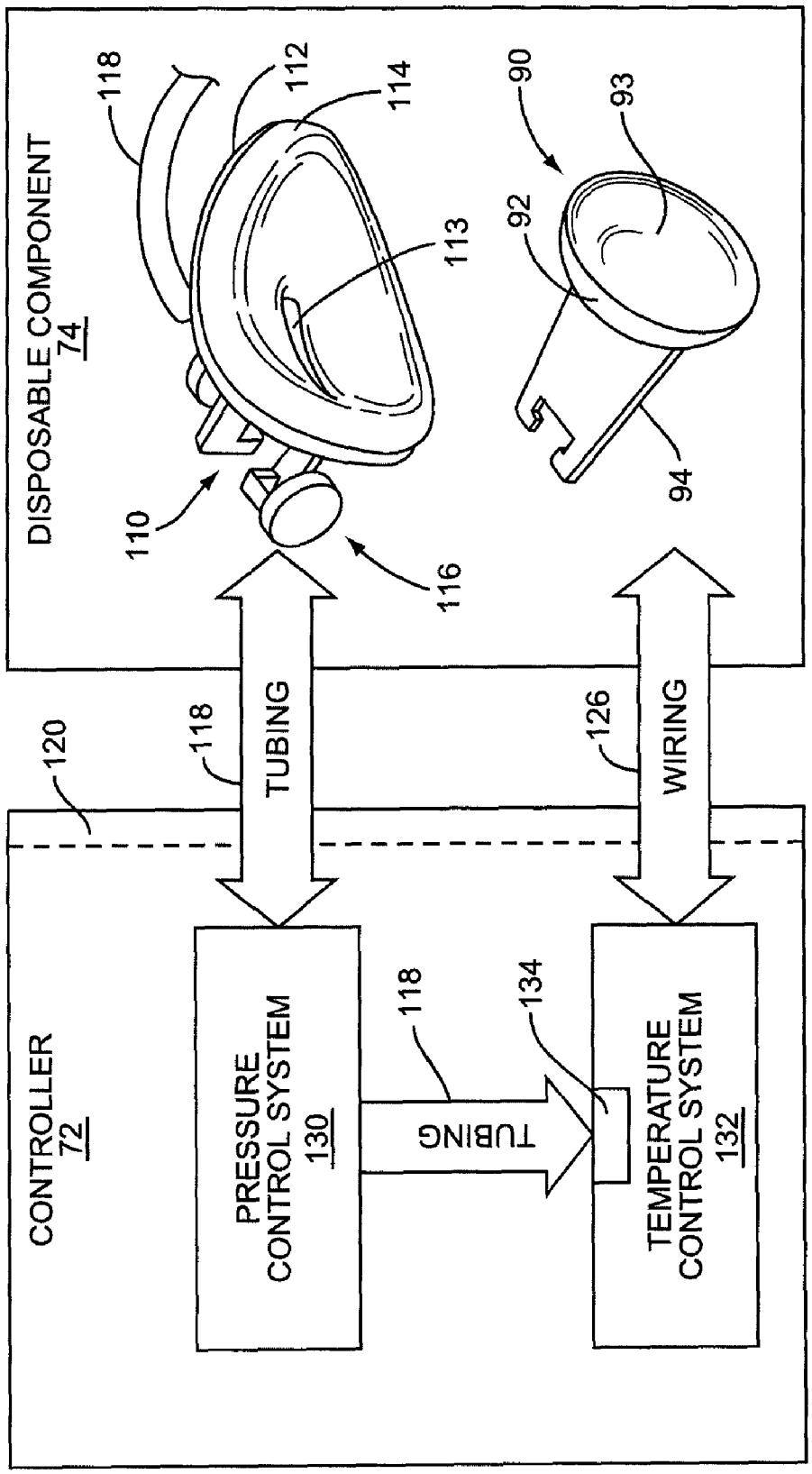
FIG. 15 illustrates a top level system diagram of the temperature and pressure control and communication components of the heat and force application device for selectively and controllably communicating to the lid warmer and eyecup components to apply heat to the inside of a patient's eyelid and/or force to the outside of the patient's eyelid, according to one embodiment relating to the present invention.

FIG. 15 supplements FIG. 14 to illustrate the interface components between the controller 72 and the disposable component 74 and the eyecup 110, at a system level. The controller 72 of the heat and force application device 70 contains a pressure control system 130 and a temperature control system 132. The pressure control system 130 is the control component within the controller 72 that controls the pressure from the force applied to the patient's eye via the eyecup 110. The temperature control system 132 is the control component within the controller 72 that controls the heat applied to the patient's eye via the lid warmer 90. The pressure control system 130 also communicates the pressure in the tubing 118 to a pressure sensor 134 within the pressure control system 130. The pressure sensor 134 is used to determine the pressure level in the tubing 118 to display the pressure on the pressure display 84 as well as to provide feedback to the controller 72 to provide the various functions and controls for the system, as will be described in more detail below. The pressure sensor 134 also allows the recordation of pressure data to be recorded by the controller 72, or an external data acquisition device (not shown) coupled to the controller 72, if desired.

FIG. 15 also illustrates more detail regarding the latching mechanism 116 on the eyecup 90. The latching mechanism 116A facilitates providing a connection between the lid warmer 90 and the lid warmer platform 94 and the eyecup 110, and the lid warmer 90 to the electronics wiring 126 when the eyecup orifice 113 is slipped over to the lens platform 94 to secure the eyecup 110 to the patient's eyelid. Two different types of latching mechanism 116, 116A were previously illustrated in FIGS. 13A and 13B, either of which can be used to secure the platform 94 to the eyecup 110, or any other type may be used.

Figure 16:
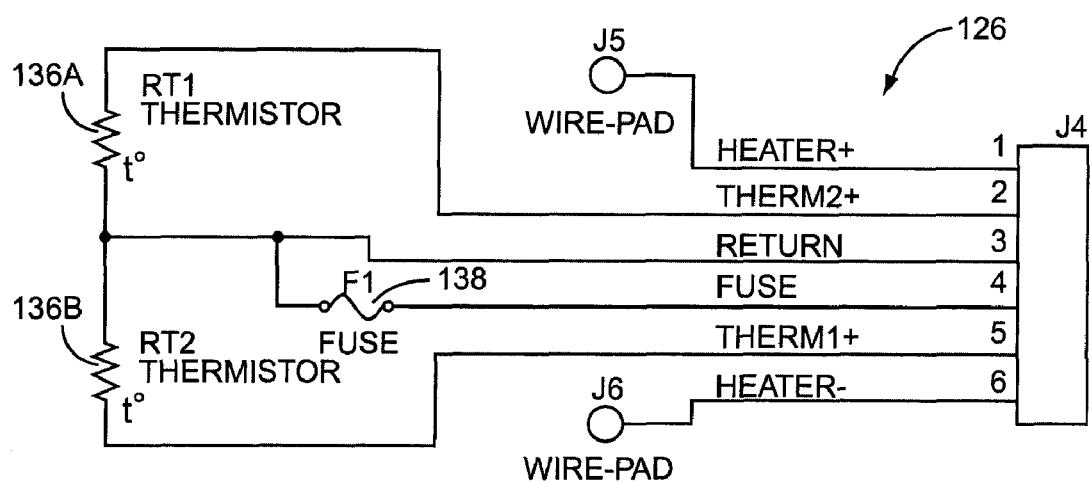
FIG. 16 illustrates an interface circuit diagram for the heating and force application device, according to one embodiment relating to the present invention.

FIG. 16 illustrates the specific wiring and supporting circuitry that comprises the electronics wiring 126 to interface the controller 72, and particularly the temperature control system 132, to the lid warmer 90 to apply heat to the patient's eye for the disclosed embodiment. Six wires make up the electronics wiring 126. The six interface wires are connected to the interface circuitry 98 that is embedded in the disposable component 74. HEATER+ and HEATER− are connected to the heating element 106 in the lid warmer 90 when the platform 94 is connected to the controller interface 76. THERM1+ and THERM2+ are coupled to two thermistors 136A, 136B. The two thermistors 136A, 136B provide an indication of temperature at the patient's eyelid as part of a temperature feedback mechanism to allow the temperature control system 132 to monitor the temperature for control. Because in the preferred embodiment, the temperature drop between the heating element 106 and the inside of the patient's eyelid is minimal, regulating temperature is simpler. This is because the thermistors 136A, 136B record temperatures closer to the actual temperatures at the glands and thus temperature overshooting is minimized. It is important to attempt to minimize temperature overshoot so as to not damage the patient's tissue. Temperature thermostats or other more complicated regulation circuits may be employed to regulate temperature as well if desired, especially if temperature overshooting is an issue. Further, the size of the heating element and power supply could also be selected so that only a known maximum amount of heat could be generated even if the heating element 106 were energized all the time. This would avoid use of a regulation circuit to prevent temperature overshoot.

Two thermistors 136A, 136B are provided for redundancy and error checking in the event one fails. Both thermistors 136A, 136B should provide the same signal indicative of temperature. Both thermistors are coupled to a common RETURN to provide common current return/grounding. Lastly, a FUSE line is provided and linked to a fuse 138, which is also coupled to the RETURN line. As will be discussed later in this application, the controller 72 can send a current over the FUSE line sufficient to blow fuse 138. The controller 72 can blow the fuse 138 to provide an indication that the lid warmer 90 has been previously used. Thus, if the lid warmer 90 is reused, the controller 72 can detect the open circuit on the FUSE line and know that the fuse 138 has been previously blown.

Figure 17:
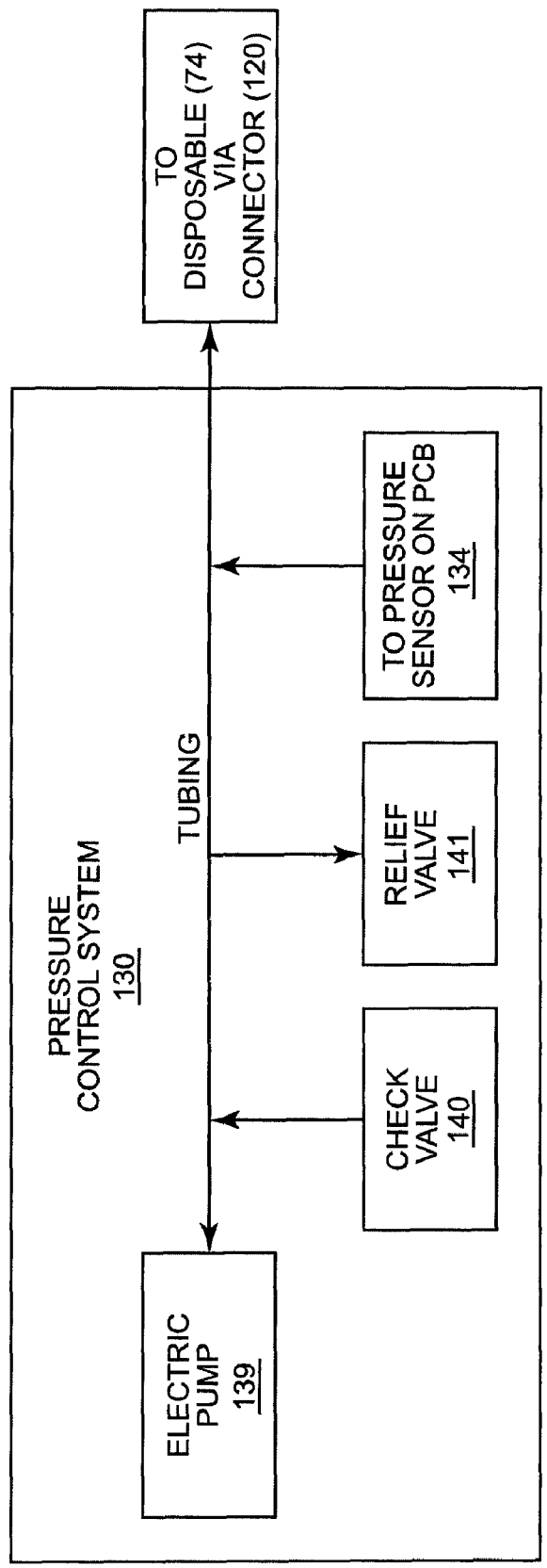
FIG. 17 illustrates a pressure control system for the heating and force application device to selectively and controllably apply force to the outside of a patient's eyelid, according to one embodiment relating to the present invention.

FIG. 17 illustrates additional components of the pressure control system 130 to provide more detail for the disclosed embodiment. The pressure control system 130 contains an electric pump 139 to pump air into the tubing 118. Other types of pumps may be used. A check valve 140 is provided inline in the tubing 118 between the electric pump 139 and the inflatable bladder 114 to allow the controller 72 to draw in air to the system to use to inflate the inflatable bladder 114 without backflow release. A relief valve 141 is also provided as a safety measure to ensure that line pressure to the eyecup 110 does not exceed maximum pressure settings in the controller 72. As illustrated in FIG. 15 and discussed above, the pressure sensor 134 is coupled to the tubing 118 to communicate the pressure in the tubing 118 to the pressure control system 130 for various functions.

Figure 18:
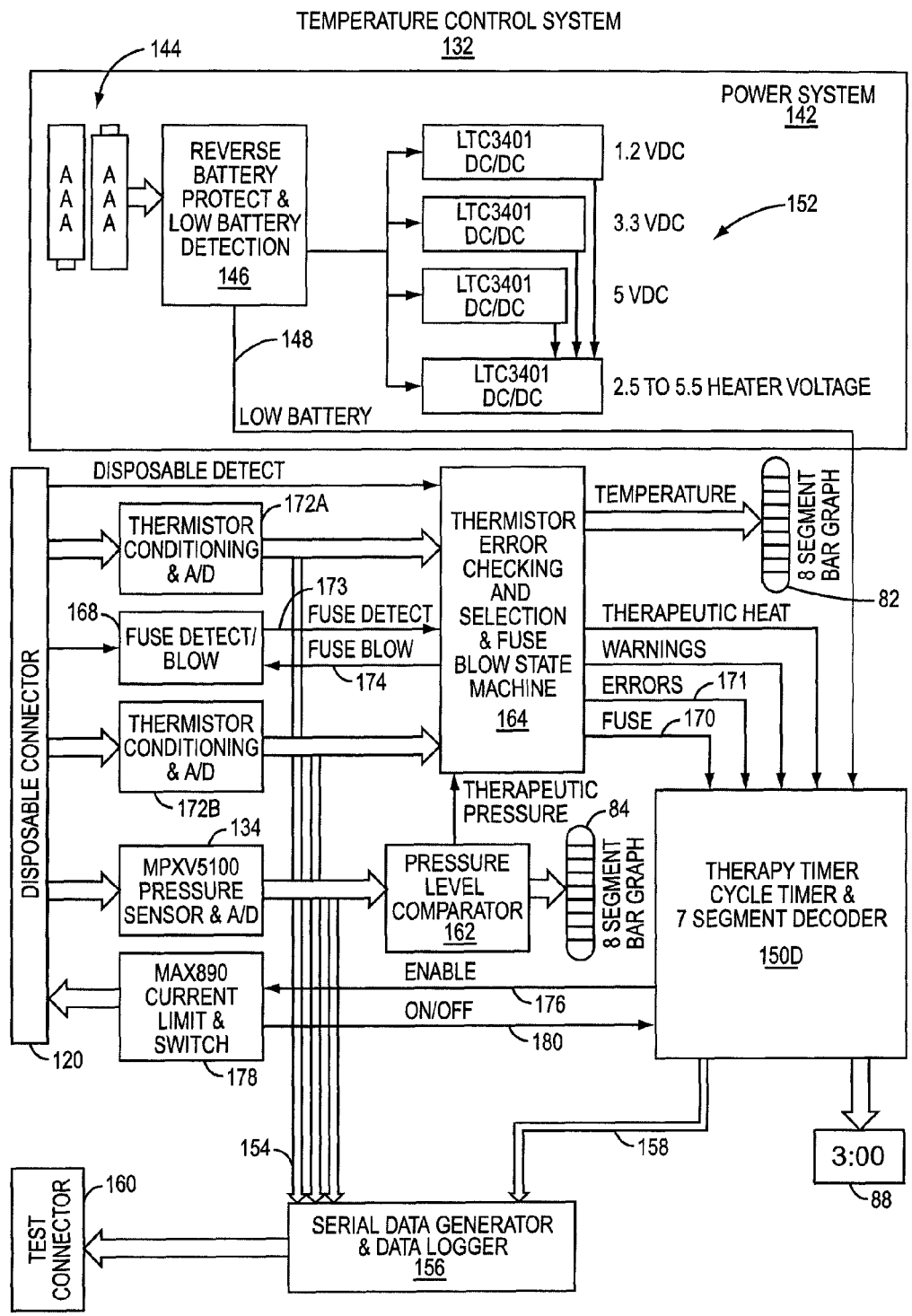
FIG. 18 illustrates a temperature control system for the heating and force application device to selectively and controllably apply heat to the inside of a patient's eyelid, according to one embodiment relating to the present invention.

FIG. 18 illustrates the temperature control system 132 in more detail for the preferred embodiment. The temperature control system 132 includes a power system 142 to provide power to the system components. In the disclosed embodiment, batteries 144 are used as the power supply. Energy from the batteries 144 are provided to a reverse battery protection and low battery detection circuit 146. If the batteries 144 are low in power, a low battery signal is communicated over a low battery signal line 148 to a timer and display controller 150. The timer and display controller 150 is responsible for controlling therapy timers and displaying them on the timer display 88. The timer and display controller 150 is also used to communicate other codes to the user regarding the controller 72, including the low battery signal. The energy from the batteries 144 are also routed to various DC-DC converters 152 to provide various voltage levels needed by the controller 72 and its components for operation. Note that the present invention is not limited to any particular type of power system or specific power components.

The temperature control system 132 may also contain a data interface 154 to provide pressure and temperature data to a data logger 156. The data logger 156 may also contain a timer interface 158 to the timer and display controller 150 so that times can be recorded for the data. The data logger 156 may be used to record data regarding patient treatments for analysis and/or to provide data for test purposes. The data logger 156 may be coupled to a test connector 160 so that logged data regarding the system may be viewed and/or recorded via an external device (not shown) coupled to the test connector 160.

The remainder of the temperature control system 132 consists of various components of the controller 72 that provide the overall operation and control of the heat and force application device 70. These components are provided in the form of various circuits and control components, including programmable gate arrays (PGA). The components interact together to provide a system logic for operation of the system. These components will be described in conjunction with FIGS. 21-26 below, which describe the logic control of the system. Note that these components can be provided by either analog or digital circuitry, and can be provided using a microprocessor-based architecting, including software, if desired.

Figure 19:
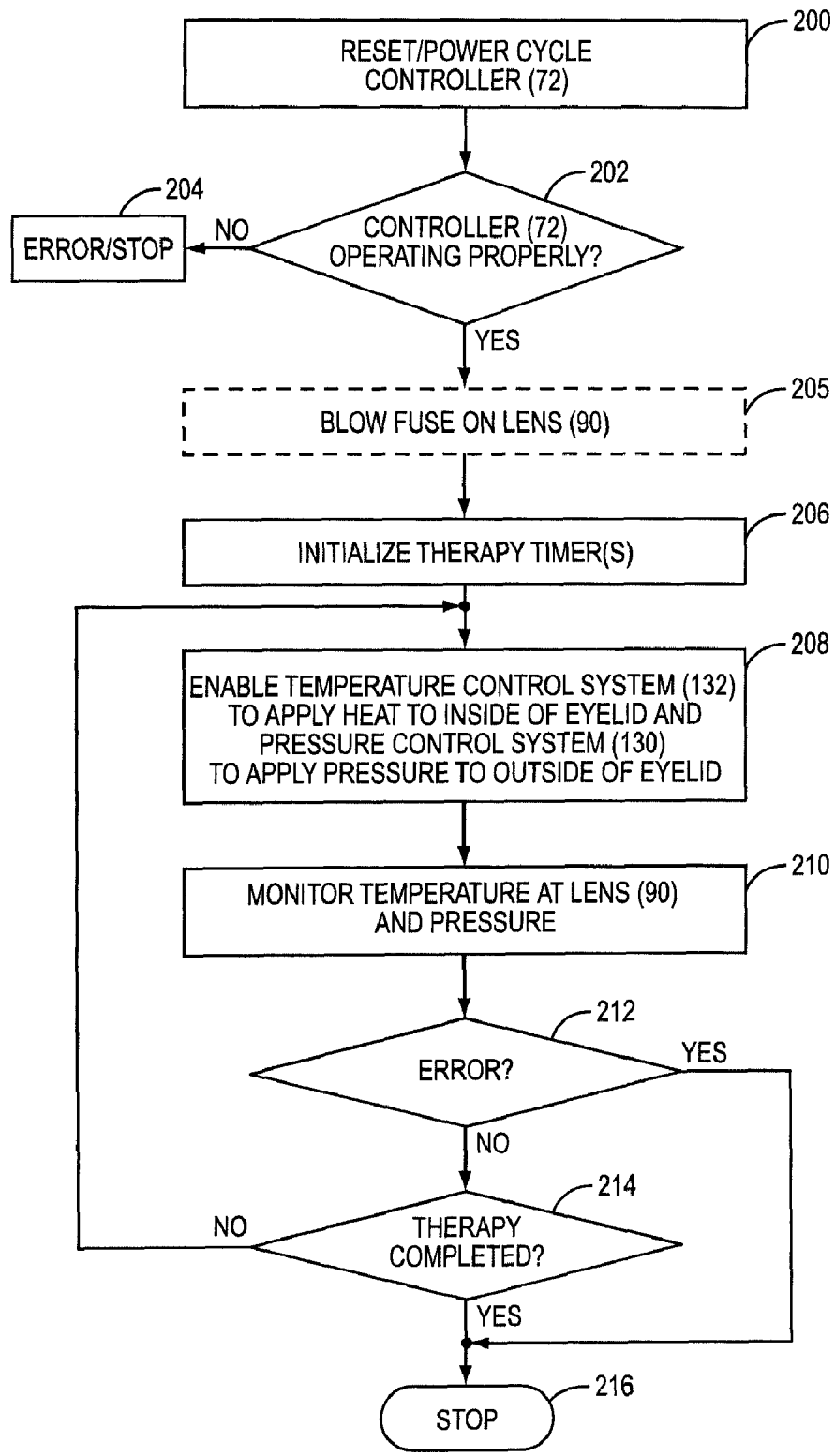
FIG. 19 is a flowchart illustrating the basic process employed by the heat and force application device to selectively and controllably apply heat to the inside of a patient's eyelid and/or force to the outside of the patient's eyelid, according to one embodiment relating to the present invention.

FIGS. 21-26 illustrate the state machine of the controller 72 and the various operations performed in the states that provide the operation and logic of the heat and force application device 70. However, before turning the state machines and the logic of the various states, a high level overall operation of the controller 72 is described with respect to the flowchart of FIG. 19. FIG. 19 will be discussed in conjunction with the various states that make up the state machine of the controller 72 illustrated in FIG. 19.

FIG. 19 illustrates a flowchart which describes the overall operation and logic of the heat and force application device 70 that is carried out by the controller 72 and its systems, including the pressure control system 130 and the temperature control system 132, according to an embodiment of the present invention. The process starts by the controller 72 resetting in the reset state (step 200 in FIG. 19, reset state 220 in FIG. 20). The controller 72 always starts in a reset state in the disclosed embodiment. The reset state may occur as a result of a power cycle or if a new disposable component 74 is connected to the controller 72. After resetting, the controller 72 performs a series of tests prior to beginning treatment to determine if the controller 72 and its components are operating properly (decision 202 in FIG. 19). If not, an error is noted and the controller 72 stops operation by entering into the stop state (step 204 in FIG. 19, stop state 224 in FIG. 20). The stop state disables the heater. If the controller 72 is operating properly (decision 202 in FIG. 19), the controller 72 proceeds with the operations to begin a treatment by entering the run and monitor states (states 226 and 228 in FIG. 20).

Figure 20:
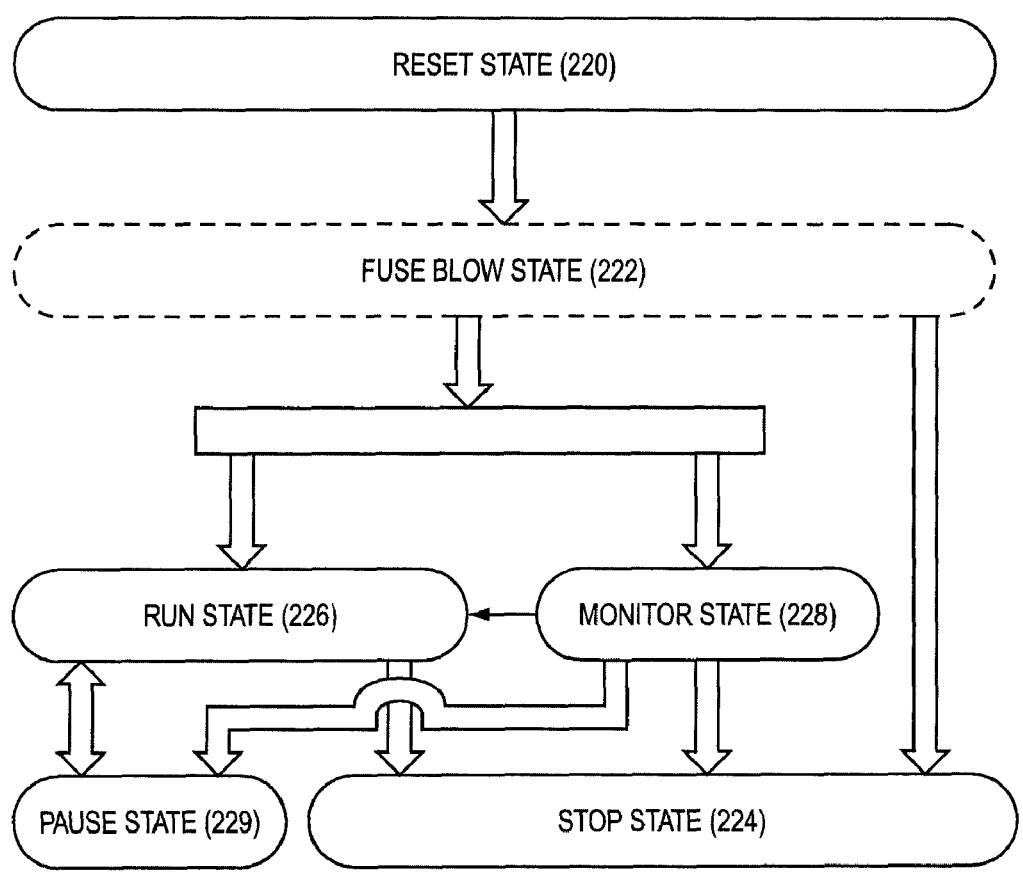
FIG. 20 illustrates a system state flow diagram for the heating and force application device, according to one embodiment relating to the present invention.

As an option, the controller 72 may first blow a fuse on the lid warmer 90 to create an open circuit in a fuse blow state (step 205 in FIG. 19, fuse blow state 222 in FIG. 20). This is so a lid warmer 90 cannot be reused for subsequent treatments for safety and contamination reasons. As part of the operation check in decision 202, the controller 72 may determine if the fuse on the lid warmer 90 has been blown in the reset state (220 in FIG. 20). If so, this would be an indication that the lid warmer 90 has already been used, and the controller 72 would enter the stop state (step 204 in FIG. 19, stop state 224 in FIG. 20). The controller 72 will continue to allow operation with the installed lid warmer 90 after the fuse is blown until the lid warmer 90 is removed. In such case, the controller 72 will enter the reset state (step 200 in FIG. 19, reset state 220 in FIG. 20).

Next, the controller 72 prepares for a therapy. The controller 72 may first initialize therapy timers in the timer and display controller 150. Timers allow the user of the controller 72 to track the amount of time that therapy has occurred, including heat and force application. Different patients may require different amounts of time for the application of heat and force during treatments. For example, a treatment cycle may include the application of heat for three minutes, but force may need to be applied, disengaged, and reapplied several times during the three minute therapy time period.

Subsequently, the controller 72 enables the temperature control system 132 and the pressure control system 130 to apply heat and force to the patient's eyelid as part of a run state (step 208 in FIG. 19, run state 226 in FIG. 20). In the disclosed embodiment of the lid warmer 90 and eyecup 110, heat is applied to the inside of the patient's eyelid, and force is applied to the outside of the patient's eyelid, as previously discussed. However, note that the controller 72 could also be used to apply heat and/or force to any part of the patient's eye or supporting structure, including but not limited to both to the outside of the patient's eyelid, and heat to the outside and force to the inside of the patient's eyelid. The controller 72 then monitors the temperature and force applied to the patient's eyelid as part of the heat and pressure regulation in a monitor state (step 210 in FIG. 19, monitor state 228 in FIG. 20). The run and monitor states 226, 228 operate simultaneously in the preferred embodiment so that heat and force are constantly being applied and temperature and pressure monitored during therapy. If during the run or monitor 226, 228, an error is detected (decision 212 in FIG. 19), the controller 72 enters the stop state to discontinue therapy (step 216 in FIG. 19, stop state 224 in FIG. 20). If an error is not detected, the run and monitor states 226, 228 continue until either an error is detected (decision 212 in FIG. 19) or the therapy is completed (decision 214 in FIG. 19).

FIGS. 21-26 illustrate flowcharts that detail the operation of the various states executed by the controller 72 to control temperature and pressure to provide MGD treatment, according to the disclosed embodiment. Each of these states were described generally above with respect to the flowchart in FIG. 19 and the state diagram in FIG. 20. Now, each state and their specific operations and functionalities as it contributes towards the operation of the heat and force application device 70 and its controller 72 will be described in more detail. Since some operations require information from various components in the pressure and temperature control systems 130, 132, references to these various components will be made as the operations of the states are described. This includes reference to components previously and not previously introduced in the temperature control system 132 in FIG. 18.

Figure 21A:
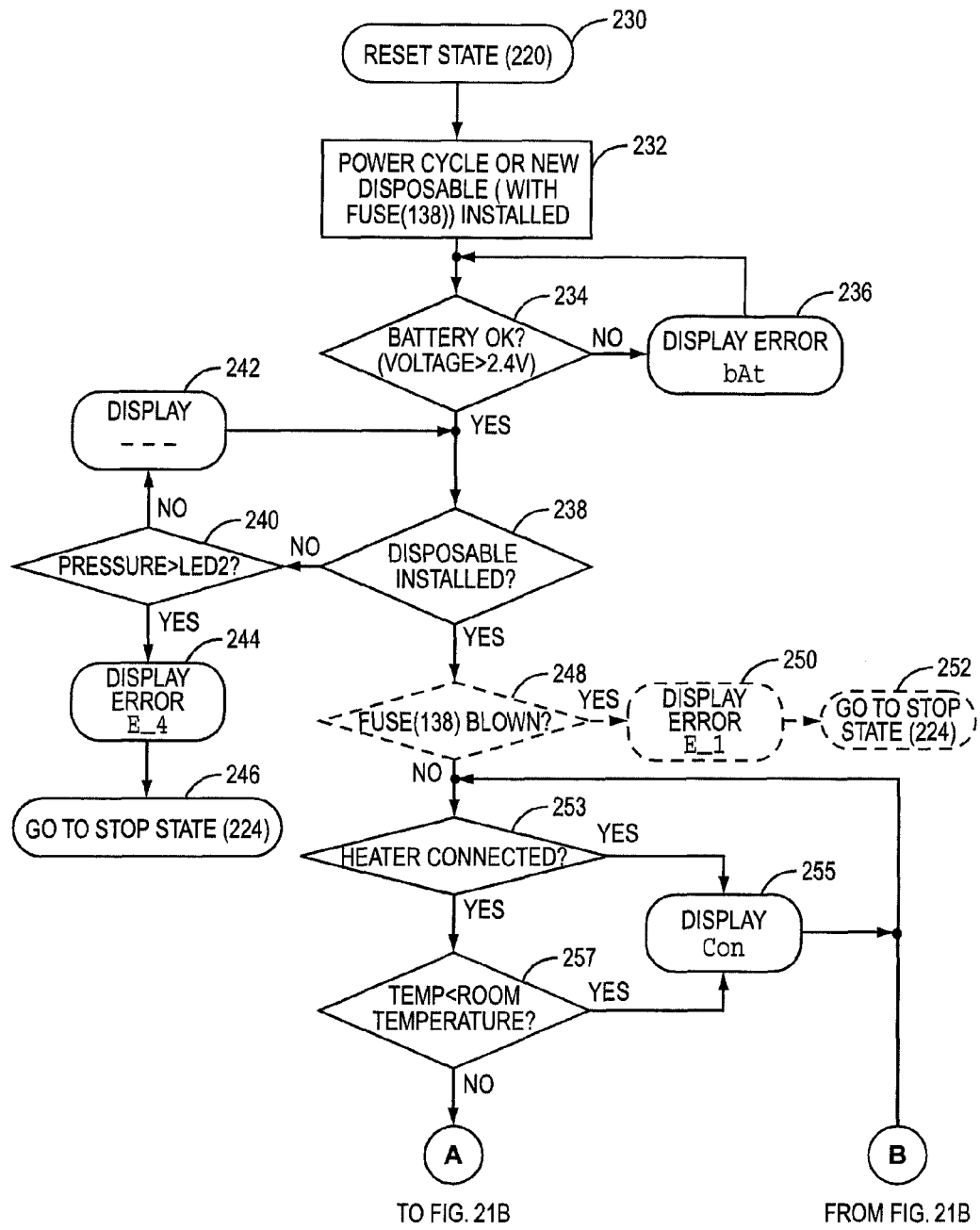
FIGS. 21A and 21B illustrate the "Reset" state flow diagram according to the system state flow diagram of FIG. 20, according to one embodiment relating to the present invention.
Figure 21B:
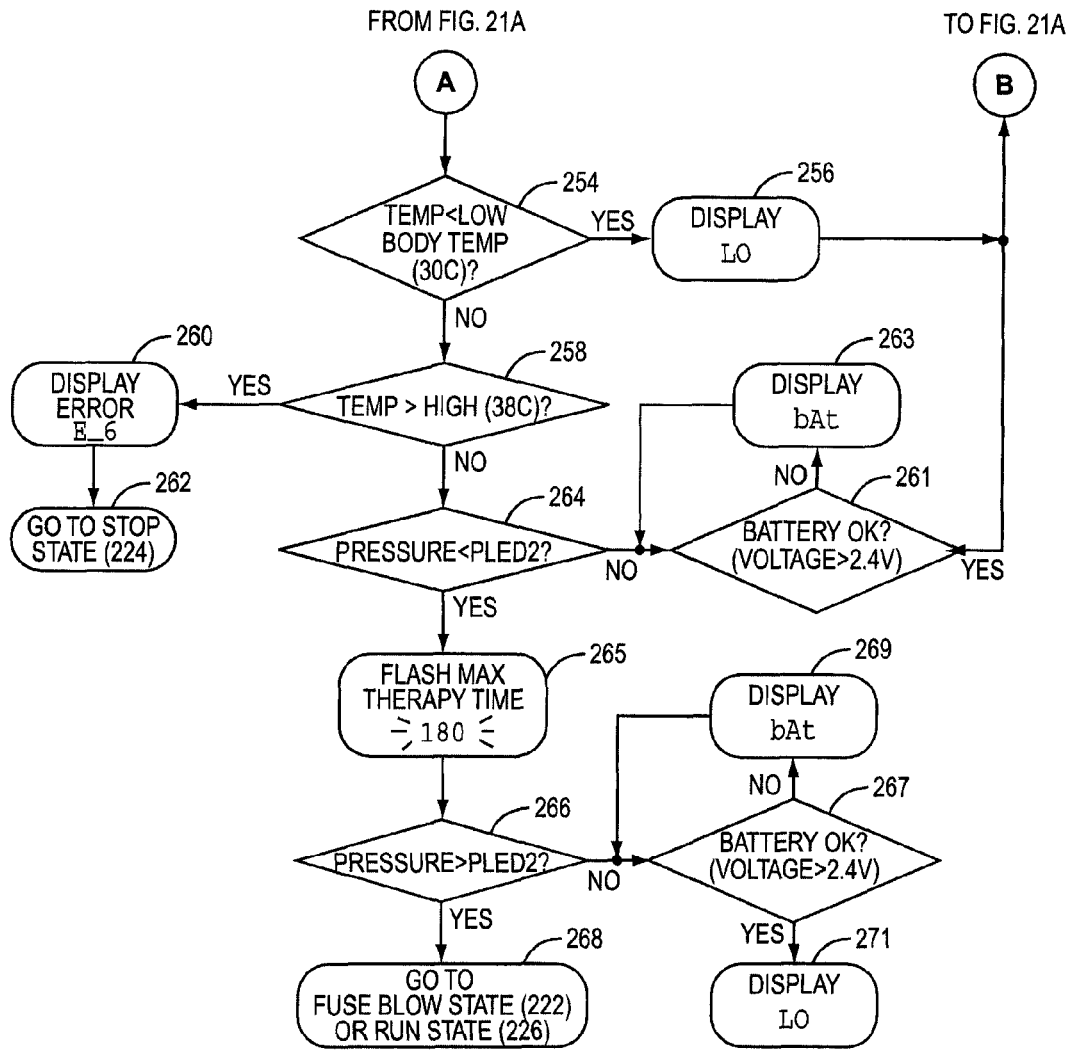

FIG. 21 illustrates a flowchart of the reset state 220 (step 230). The controller 72 enters the reset state 220 when either a power cycle occurs or a new disposable lid warmer 90 (with an intact fuse 138 as an optional feature) is installed (step 232). Thereafter, the controller 72 checks to determine if the power supply voltage is above a set minimum voltage level (decision 234). In the disclosed embodiment, the batteries 144 must provide at least 2.4 Volts. If they do not, an battery error (e.g. "bAt") is displayed on the timer display 88 (step 236). Referring to FIG. 19, the low battery error is displayed by timer and display controller 150 on the timer display 88 in response to the low battery signal sent from the low battery detection circuit 146 over the low battery signal line 148.

If the batteries 144 are producing a sufficient voltage, the controller 72 continues with the reset state 220 by next determining if the disposable component 74 is installed (decision 238). If not, the controller 72 is not ready for operation. However, before going to the stop state 224 (step 246), the controller 72 takes the opportunity to perform a pressure diagnostic test. Referring to FIG. 18, the pressure sensor 134 signal indicative of measured pressure in the tubing 118 is communicated to a pressure level comparator 162, which communicates the pressure level to the pressure display 84 and to an error checking control system 164. Ideally, the pressure in the tubing 118 should not be greater than ambient pressure. If the pressure sensor 134 does not provide a signal indicative of ambient pressure (decision 240), this is an indication that the pressure sensor 134 may not be operating properly. Thus, a pressure sensor 134 error message (e.g. "E_4") may be displayed on the timer display 88 (step 244), via the ERRORS signal line 171 (see FIG. 18), before the controller enters the stop state 224 (step 246). If the pressure sensor 134 is properly measuring pressure, the timer display 88 remains in the reset display state (e.g. "_ _ _ _") (step 244) and the controller 72 waits until a disposable component 74 is installed (decision 238). Note that because ambient pressure may not be 0 mm Hg depending on where the heat and force application device 70 is located, a threshold pressure level is used. In the disclosed embodiment, the threshold pressure level is 1 psi.

Once the disposable component 74 is installed, the controller 72 can next optionally determine if the fuse 138 on the lid warmer 90 is blown (decision 248). This check is only performed if the lid warmer 90 is equipped with a fuse 138 that can be blown by the controller 72 to indicate when the disposable component 74 has been previously used for a treatment. In this instance and referring to FIG. 18, a fuse detect and blow circuit 168 communicates a fuse detect signal over the FUSE DETECT line 173 from the interface circuitry 98 on the disposable component 74 to the error check controls system 164. This is so the controller 72 can determine if the disposable component 74 has been previously used. If the fuse 138 is blown, the controller 72 will not allow therapy to be provided using the currently installed disposable component 74 for safety and sterility reasons until the disposable component 74 is replaced with a previously unused disposable one (which will have an intact fuse 138 on the interface circuitry 98). The controller 72 will display an error message (e.g. "E_1") on the timer display 88, via the FUSE signal line 170 to indicate to the user that the disposable component 74 must be replaced (step 250) before going to the stop state 224 (step 252).

If the fuse 138 is not blown on the disposable component 74 (decision 248) or if the fuse check feature is not included in the controller 72, the controller 72 next determines if the heating element 106 is connected (decision 253). If not, the controller displays a connect message (e.g. "Con") on the timer display 88 to indicate to the user that the heating element 106 (i.e. the lid warmer 90) is not connected to the controller 72 and thus therapy cannot begin (step 255). Once the heating element 106 is connected to the controller 72, the controller 72 next determines if the temperature level at the lid warmer 90 is lower than room or ambient temperature (decision 254). If so, this is an indication that the disposable component 74 may not be installed on a patient's eyelid such that the user is ready for the controller 72 to begin therapy. Referring to FIG. 18, thermistor conditioning circuits 172A, 172B communicate signals from each of the thermistors 136A, 136B at the disposable component 74 to the error checking control system 164. In response, the connect message (e.g. "Con") may again be displayed on the timer display 88 (step 255). The controller 72 will continue to check the heating element 106 connection and the temperature at the lid warmer 90 until the thermistors 136A, 136B read a temperature of room temperature or greater (decision 254). This provides some assurance that the disposable component 74 is installed on the patient.

Next, the controller 72 will check to determine if the temperature level at the lid warmer 90 is lower than body temperature (e.g. 30 degrees Celsius) (decision 254). This enables the controller 72 to determine if the disposable component 74 is installed on the patient's eye, because if so installed, the temperature at the lid warmer 90 should be at least body temperature. If the temperature at the lid warmer 90 is not at least body temperature, an error message (e.g. "LO") may be displayed on the timer display 88 in response to indicate to the user that the temperature at the lid warmer 90 is abnormally low (step 256). The controller 72 will thereafter cycle back through the series of checks to ensure that the lid warmer 90 is properly installed and ready for use in therapy (decisions 253, 257, 254, 258).

Once the temperature of the lid warmer 90 is at or above room temperature (decision 254), the controller 72 then determines if the temperature at the lid warmer 90 is at a temperature level that is higher than would be expected before therapy has begun (i.e. an over temperature level, e.g. 30 degrees Celsius) (decision 258). This may be indicative of an ambient temperature that is deemed to high to begin therapy. If so, an error message (e.g. "E_6") may be displayed on the timer display 88 by the error check control system 164 (step 260) before the controller 72 enters the stop state 224 (step 262). If not, the controller will check the pressure level in the tubing 118, via the pressure sensor 134, to ensure pressure level is at ambient pressure since the controller 72 has not inflated the bladder 114 to generate a pressure to the patient's eyelid (decision 264). If the pressure level is lower than ambient pressure, this may be an indication of an error, such as an error with the pressure sensor 134 or the power source. If the pressure level is lower than ambient pressure, the controller 72 will check to determine if the battery voltage is sufficient (decision 261) and repeat through the series of checks (decisions 253, 257, 254, 258, 264) before allowing therapy to start. Once these series of checks have been satisfied, therapy can begin. In response, the controller 72 will cause the timer display 88 to be reset to indicate the beginning of a therapy session (e.g. a 180 second countdown)(step 265). The controller 72 will then check to ensure that the pressure level in the tubing 118 is not higher than ambient pressure or a desired pressure level that would be indicative of a pressure sensor 134 or other problem (decisions 267, steps 269, 271) before proceeding to the run state 226, or the fuse blow state 222 if provided (step 268).

Figure 22:
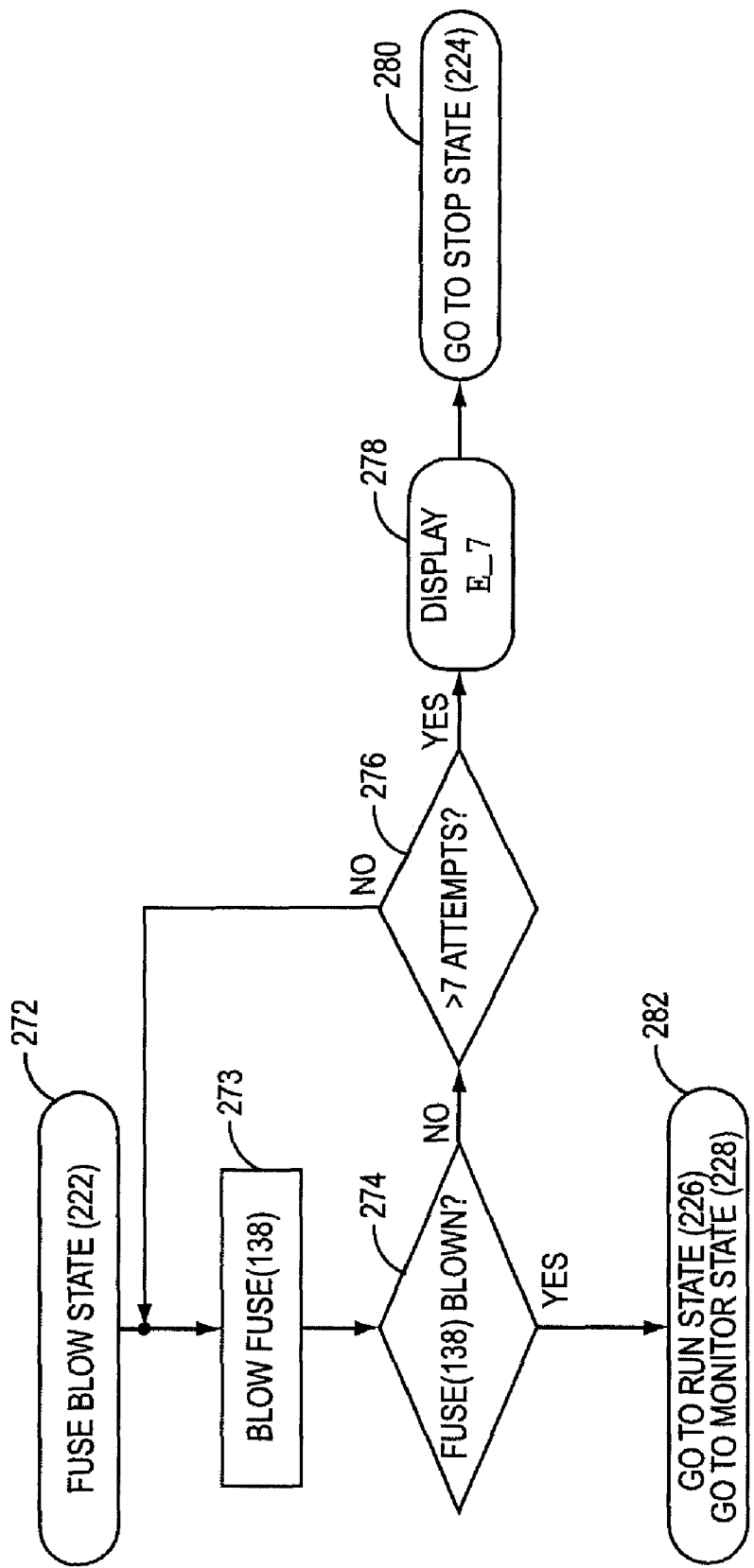
FIG. 22 illustrates the optional "Fuseblow" state flow diagram according to the system state flow diagram of FIG. 20, according to one embodiment relating to the present invention.

After leaving the reset state 220, the controller 72 may go into the fuse blow state 222 (step 272), which is illustrated in FIG. 22. If provided, the controller 72 blows the fuse 138 on the lid warmer 90 so that it cannot be reused after the controller 72 is reset (step 273). Referring to FIG. 18, the error checking control system 164 causes a sufficient current to be sent over the FUSE BLOW line 174 and to the fuse detect and blow circuitry 168 to blow the fuse 138 at the disposable component 74. The controller 72, via the error check control system 164, then checks to see if the fuse 138 was successfully blown via the FUSE DETECT line 173 (decision 274). If not, and after seven unsuccessful attempts to do so (decision 276), an error message (e.g. "E_7") may be generated on the timer display 88 (step 278) before going to the stop state 224 (step 280). It the fuse 138 is successfully blown, the controller 72 is ready to provide therapy. The controller 72 enters the run and monitor states 226, 228 (step 282) to be executed simultaneously to apply heat and force to the patient's eyelid as well as monitor the temperature and pressure applied for control purposes.

Figure 23:
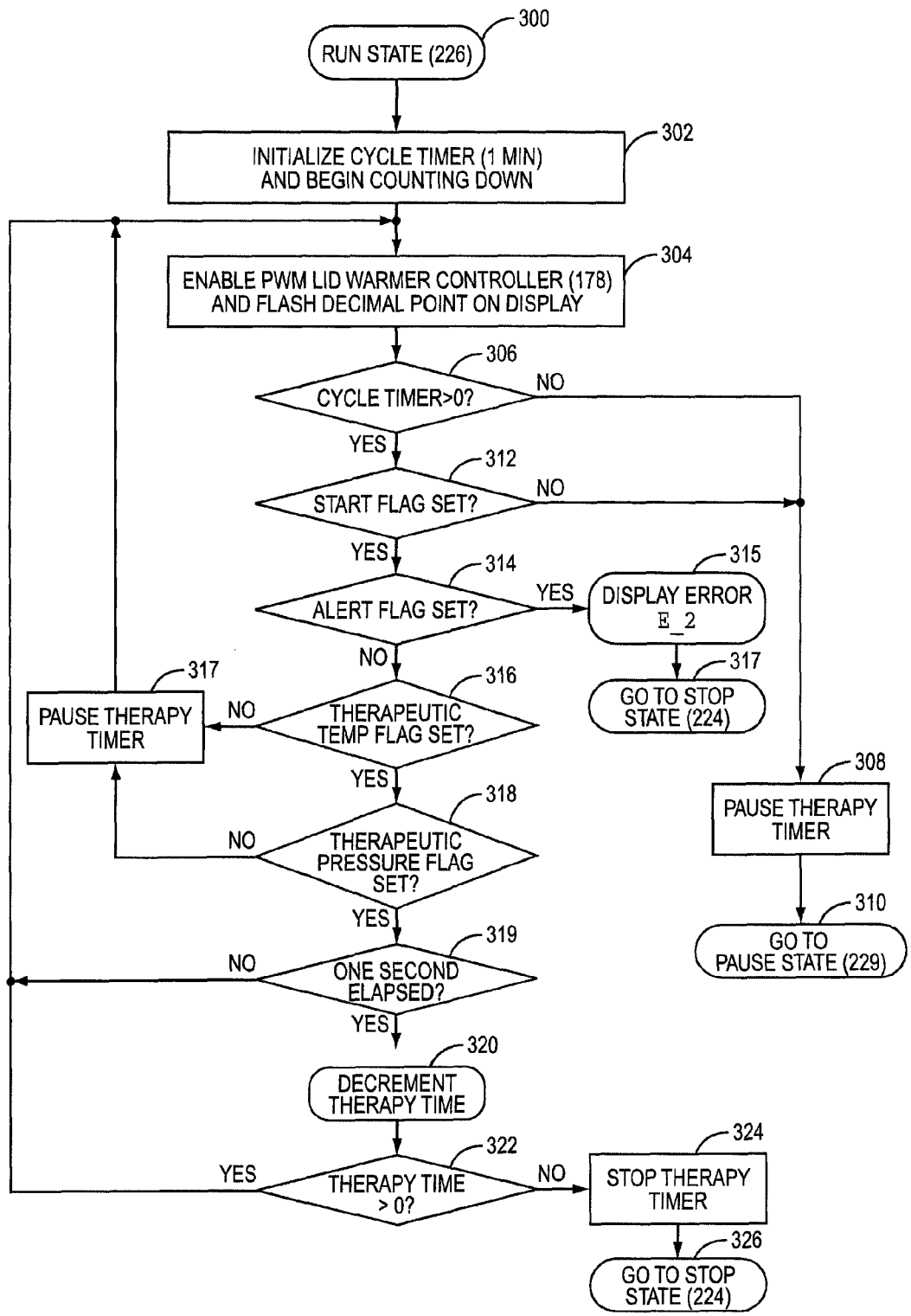
FIG. 23 illustrates the "Run" state flow diagram according to the system state flow diagram of FIG. 20, according to one embodiment relating to the present invention.
Figure 25A:
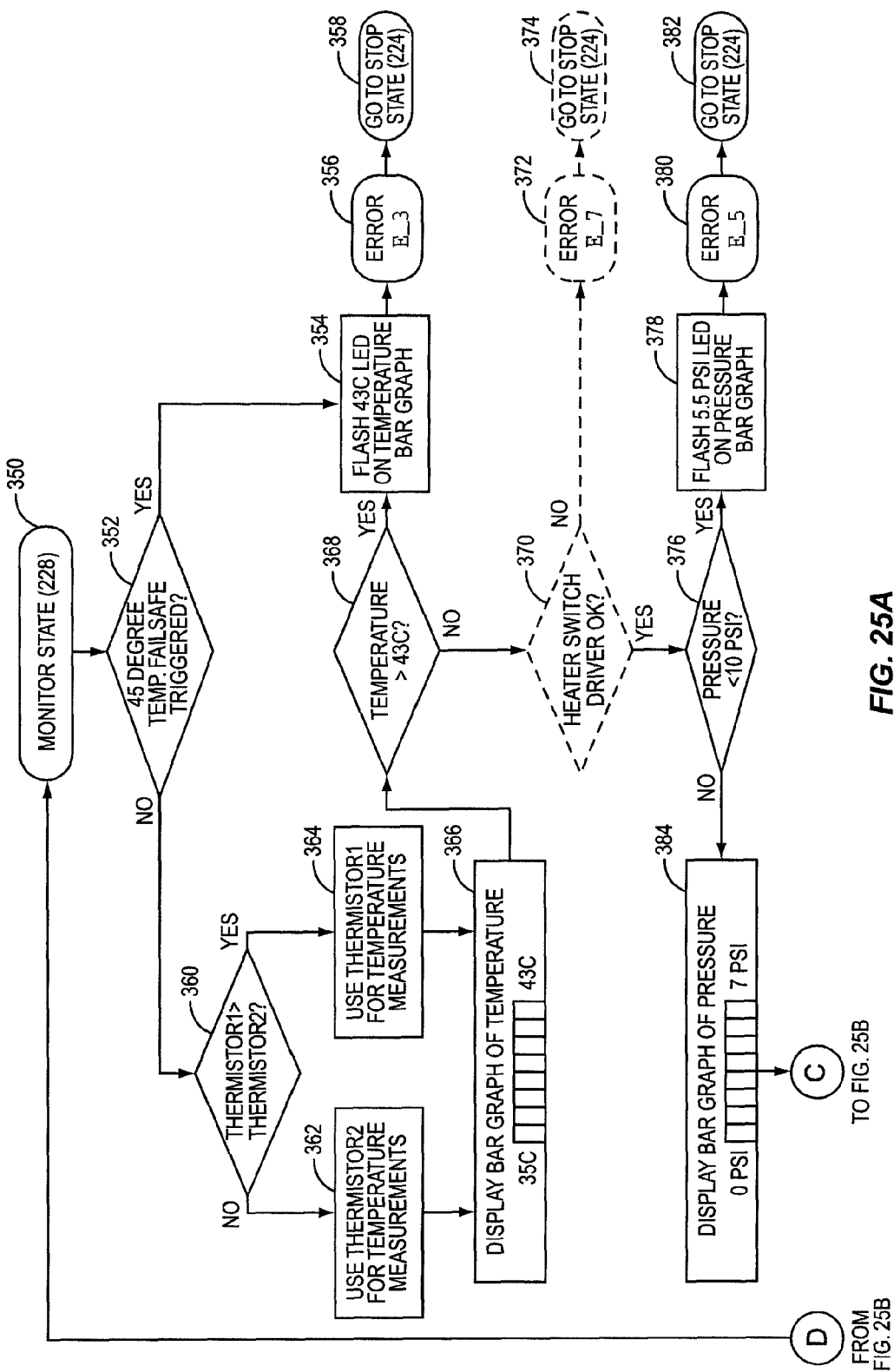
FIGS. 25A and 25B illustrate the "Monitor" state flow diagram according to the system state flow diagram of FIG. 20, according to one embodiment relating to the present invention.
Figure 25B:
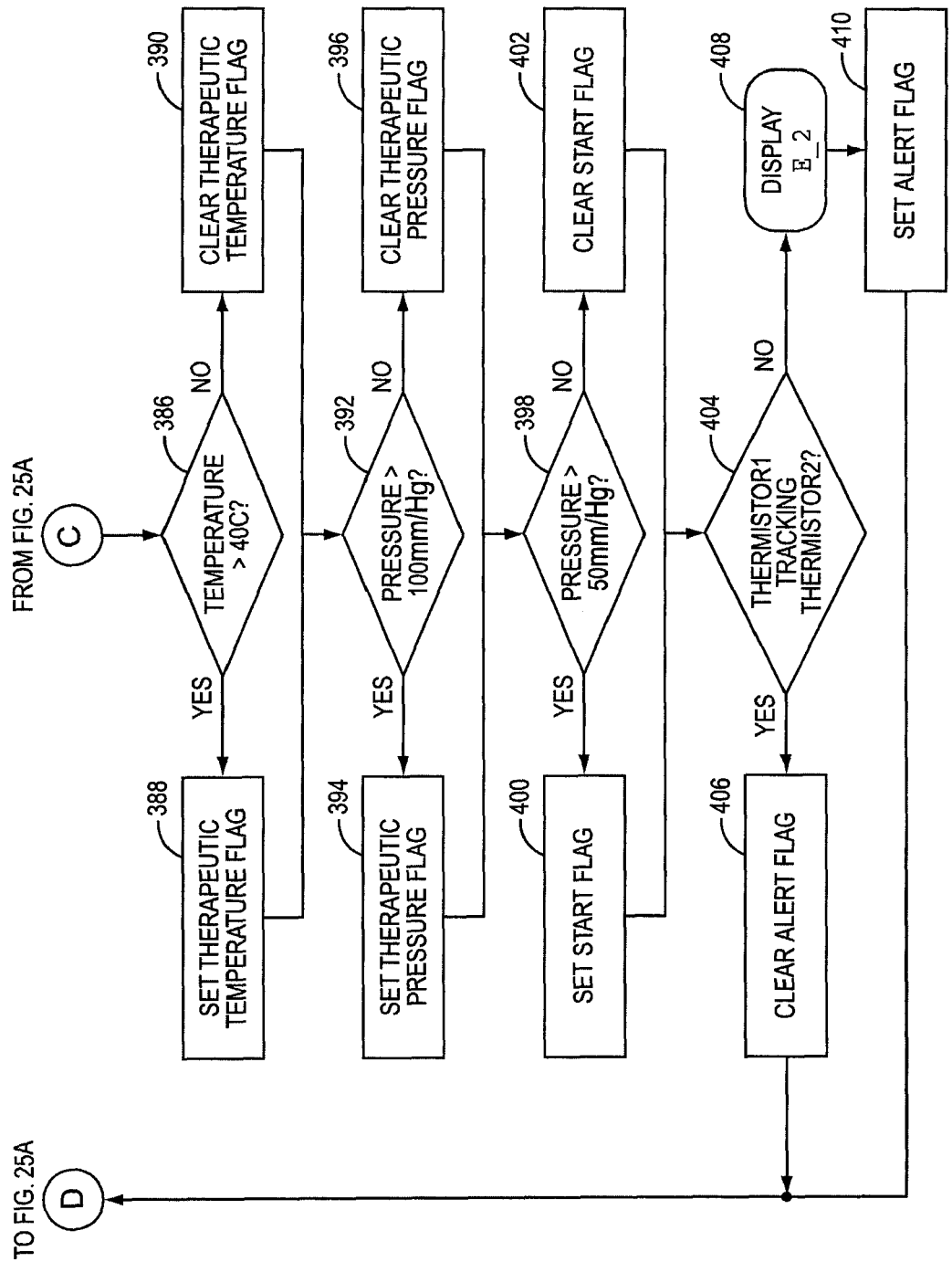

FIG. 23 illustrates the run state 226 (step 300). The controller 72 enters the run state 226 to begin therapy either from the reset state 220 (step 268 in FIG. 21) or optionally from the fuse blow state 222 (step 282 in FIG. 22). The run state 226 will be discussed before the monitor state 228, which is illustrated in FIGS. 25A and 25B. Turning to FIG. 23, the run state 226 begins by the controller 72 initializing a cycle timer and beginning a count down timer at the count down time value programmed into the system (step 302). Turning to FIG. 18, the timer and display controller 150 resets the timers. The count down timer is displayed on the timer display 88. The cycle timer will cause the timer display 88 to blink at the end of a cycle such that the timer display 88 is used to provide the cycle timer and countdown timer information to a user.

In the disclosed embodiment, the cycle timer is the amount of time that force should be applied continuously to the patient's eyelid before being released. In the disclosed embodiment, this is set at one minute. The count down timer is the total therapy time for heat to be applied to the patient's eyelid. In the disclosed embodiment, the count down timer is set at three minutes. Thus, there will be three cycles during the therapy. The timers are not only used to provide a visual timing indicator to the user, but are also used to control heat and force application to the patient's eyelid as will be further discussed. These timer values could also be based on programming instructions provided by the user to the controller 72.

Figure 24:
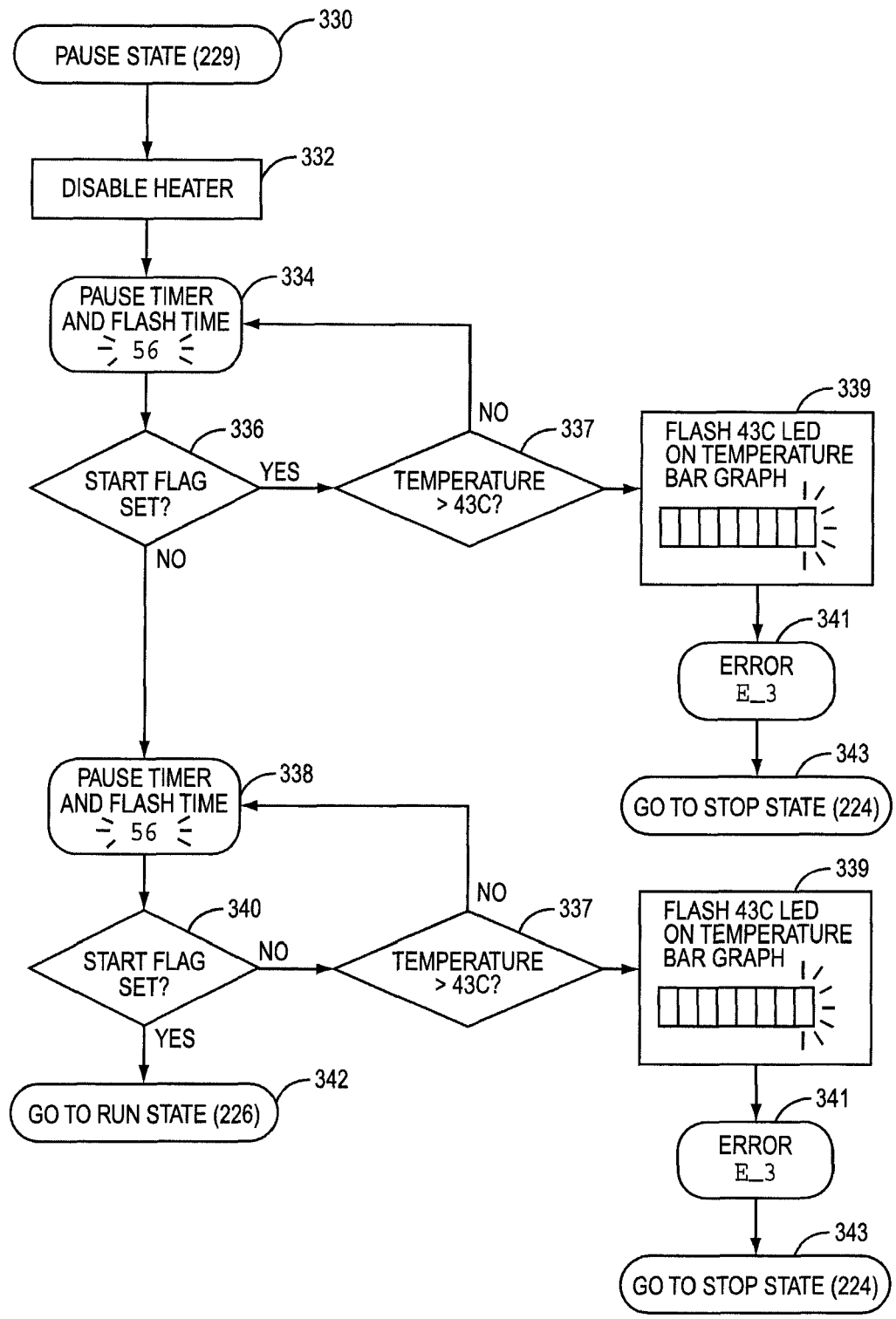
FIG. 24 illustrates the "Pause" state flow diagram according to the system state flow diagram of FIG. 20, according to one embodiment relating to the present invention.

Thereafter, the temperature control system 132 enables heat to be applied to the patient's eyelid via the lid warmer 90 and its lens (step 304). The beginning of heat therapy is signaled to the user by flashing the decimal point on the timer display 88 in the disclosed embodiment (step 304). Referring to FIG. 18, the therapy timer controller 150 causes an enable signal to be generated over an ENABLE line 176 to activate a lid warmer controller 178 to apply an electrical signal to the HEATER+ and HEATER− lines in the electronics wiring 126 (see FIG. 16). This causes the heating element 106 in the lid warmer 90 to energize and generate heat to the patient's eyelid. The lid warmer controller 178 controls the heating element by turning on and off the electrical signal to the heating element 106. However, any type of heating control can be employed, including but not limited to PWM techniques. Thereafter, the timer and display controller 150 determines if the cycle timer has not expired (decision 306). If it has expired, the therapy timer is paused (step 308) and the pause state 229 is entered (step 310). This is because the force must be released before therapy can continue. The pause state 229 is illustrated in FIG. 24 and will be discussed later below.

If the cycle timer has not expired (decision 306), a start, alert, therapeutic temperature, and therapeutic pressure flags are checked (decisions 312, 314, 316, 318). These flags are set by the monitor state 228 as part of error checking, which is illustrated in FIGS. 25A and 25B and will be discussed later below. At this point, all that is required to understand is that these flags being set means that heat therapy can continue. If not, either the stop state 224 (step 317) or the pause therapy timer state 229 (step 308, 317) will be entered before returning back to the run state 226. If the flags are properly set, the therapy timer will be decremented with the elapsed time as each second elapses (steps 319, 320) with heating element 106 continuing to be energized to produce heat at the lid warmer 90 until the therapy time is complete (decision 322). When the therapy time has completed, meaning that the therapy timer time has counted down to zero time in the disclosed embodiment, the therapy timer is stopped (step 324) and the stop state 224 is entered to discontinue heating the patient's eyelid (step 326).

Before describing the monitor state 228, which is illustrated in FIGS. 25A and 25B, the pause state 229 will next be described. The pause state 229 is illustrated in FIG. 24. The pause state 229 is entered to disable energizing the heating element 106 and wait for the user to release the force lever 86 (or other pressure control mechanism) before re-entering the run state 226. This ensures that force is not continuously applied to the patient's eyelid during the entire therapy session without some relief to allow blood flow in the eyelids for safety precaution reasons. The timer and display controller 150 first disables the heating element 106 by removing the enable signal from the ENABLE line 176 to the lid warmer controller 178 (step 332). The timer display 88 is paused from changing, and the cycle time is flashed indicating that the end of the cycle has occurred (steps 334, 338). The start flag is checked (decisions 336, 340) to ensure that the user has released force so that therapy can be restarted, in which case the system returns back to the run state 226 (step 342). The start flag is set and reset in the monitor state 228.

If the start flag is set (decision 336, 340), the controller 72 may also check to determine if the temperature at the lid warmer 90 is above a defined threshold temperature level. If so, this may be indicative of the heating element 106 producing a heat exceeding an upper temperature level of heat to be applied to the patient (decisions 337, 343). In the disclosed embodiment, this upper temperature threshold level is 43 degrees Celsius. However, this threshold temperature level can be set to be any temperature level threshold desired. If the threshold temperature level is exceeded, the temperature display 82 may be flashed to indicate this condition to the user as well as an error (e.g. "E_3") being displayed on the timer display 88 (step 341, 343) before the controller 72 enters the stop state 224 (steps 343, 349).

The monitor state 228 is illustrated by the flowchart of FIGS. 25A and 25B. The monitor state 228 will continuously check the temperature and pressure applied to the patient's eyelid. Temperature is checked using thermistors 136A, 136B, and pressure is checked using pressure sensor 134 coupled to the tubing 118. The results of the measured temperature and pressure are displayed on the controller 72, via the temperature and pressure displays 82, 84. The temperature and pressure measurements are analyzed to ensure that no error conditions have occurred. In addition, the monitor state 228 will signal to the run state 226, which is executing simultaneously with the monitor state 228, when therapeutic temperatures and pressures have been reached.

Turning to FIG. 25A, the temperature control system 132 determines if the temperature is above a threshold maximum temperature level failsafe for safety reasons (decision 352). This threshold maximum temperature level may be set to 45 degrees Celsius. If so, the over temperature condition is flashed on the temperature display 82 to indicate to the user that the temperature is over the allowed temperature setting (step 354). Further, an error message (e.g. "B_3") may be displayed on the timer display 88 in the same regard (step 356). The controller 72 will enter the stop state 224 (step 358) to halt therapy. If the temperature at the lid warmer 90 is not above the set safe temperature threshold, the error checking controller checks to see if the two temperature thermistors 136A, 136B are different in value (decision 360). The thermistor 136A, 136B providing the higher reading is used for temperature monitoring as an additional precaution to prevent an unsafe temperature from being applied to the patient's eyelid (steps 362, 364). The measured temperature is then displayed on the temperature display 82 (step 366).

The temperature at the thermistor 136A, 136B used to measure the temperature is checked again to ensure that the temperature at the lid warmer 90 has not exceeded the maximum allowable temperature again as a safety precaution (decision 368). If the temperature has exceeded the maximum allowable temperature, the same steps previously performed earlier for this check are performed (steps 354, 356, 358). If not, the heater switch driver in the lid warmer controller 178 may be optionally checked to ensure that it is working correctly to ensure that heat will not be applied to the patient's eyelid when the switch is turned off via the ON/OFF signal line 180 in FIG. 18 (decision 370). If the heater switch driver has a malfunction, and error message (e.g. "E_7") may be generated on the timer display 88 to indicate the hardware failure to the user (step 372). The system then enters the stop state (224) to disable the application of heat (step 374).

If the heater switch driver is operating properly (decision 370), the system determines if the pressure level in the tubing 118 is above the maximum allowable pressure as a safety precaution to prevent too much pressure from being applied to the patient's eyelid (decision 376). If so, the over pressure condition is displayed on the pressure display 84 and the timer display (e.g. "E_5") to indicate the over pressure condition to the user (step 378, 380) before entering the stop state 224 (step 382). If no over pressure condition exists, the measured pressure is displayed on the pressure display 84 (step 384).

Next, as illustrated in FIG. 25B, the system determines if the temperature at the lid warmer 90 is above the therapeutic temperature setting (decision 386). This is an indication that the temperature has risen at the lid warmer 90 necessary to provide therapy and so that the therapy timer will accumulate in the run state 226. The therapeutic temperature setting is set by the system. Alternatively, it may be programmed by the user into the controller 72. If the temperature is above the therapeutic temperature setting (decision 386), the therapeutic temperature flag is set (step 388). If not, the therapeutic temperature flag is cleared (step 390).

In a similar manner to temperature, the system also determines if the pressure in the tubing 118 indicative of the pressure applied to the patient's eyelid is above the therapeutic pressure setting (decision 392). This is an indication that the pressure has risen to a level necessary to provide therapy and so that the therapy timer will accumulate in the run state 226. The therapeutic pressure setting is set by the system. Alternatively, it may be programmed by the user into the controller 72. If the pressure level is above the therapeutic pressure setting (decision 392), the therapeutic pressure flag is set (step 394). If not, the therapeutic pressure flag is cleared (step 396). The system also checks to determine if the pressure level has increased to a minimum threshold level indicative of the force lever 86 being engaged by the user to allow therapy to start (decision 398). If so, the start flag is set (step 400). If not, the start flag is cleared (step 402).

The system also monitors the temperature thermistors 136A, 136B to determine if their measured signals track each other as an indication of whether the thermistors 136A, 136B may have malfunctioned (decision 404). Two thermistors are unlikely to produce the same output for a given temperature, but they change in like kind in response to the same conditions. If they are properly tracking each other, the alert flag is cleared indicating that no error condition exists for the thermistors (step 406). If not, an error message (e.g. "E_2") may be displayed on the timer display 88 (step 408) before the alert flag is set (step 410). As previously discussed, the run state 226 checks the alert flag as a condition of allowing therapy to continue. The monitor state 228 continues to execute in a looping fashion until a condition occurs to place the controller 72 in the stop state 224.

Figure 26:
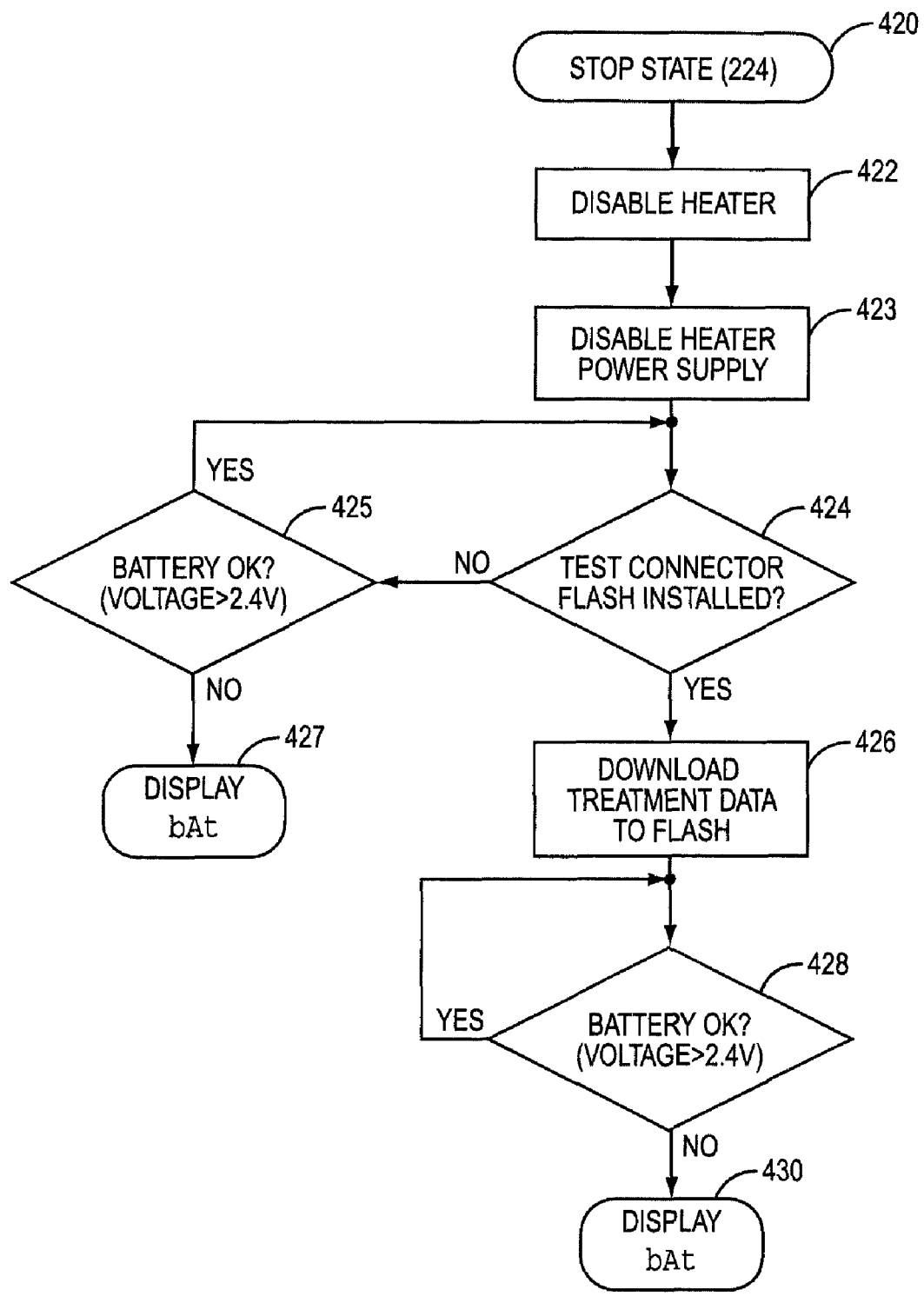
FIG. 26 illustrates the "Stop" state flow diagram according to the system state flow diagram of FIG. 20, according to one embodiment relating to the present invention.

FIG. 26 illustrates the last state of the controller state machine, the stop state 224. The stop state 224 is entered when the total therapy time has reached its preset maximum time or any error condition occurs (step 420). Once in the stop state 224, the controller 72 cannot be restarted with the same disposable component 74 for safety reasons. The heating signal to the heating element 106 is disengaged to stop heat from being applied to the patient's eyelid (step 422). Further, the power supply to the heating element 106 can also be disabled as a further measure to ensure that heat will no longer be applied to the patient's eyelid (step 423). An optional test connector may be installed to download sensor or other operational data to memory for data logging or for testing. If installed (decision 424), the data may be downloaded to memory (step 426). Once the treatment data is downloaded, the controller 72 can check the status of the battery until the controller 72 is reset to enter the reset state 230 (see. FIG. 21), since the controller 72 is not performing therapy and is otherwise dormant (decision 428, step 430). If the test connector is not installed, the controller 72 continues to check for installation of the optional test connector as well as performing a battery level check (decision 425, step 427) until either installed or the controller 72 is reset to enter the reset state 220 (see FIG. 21). Thereafter, the system enters the run state 226, in which case, therapy can begin again once the error conditions are eliminated and a new disposable component 74 is installed.

Figure 27:
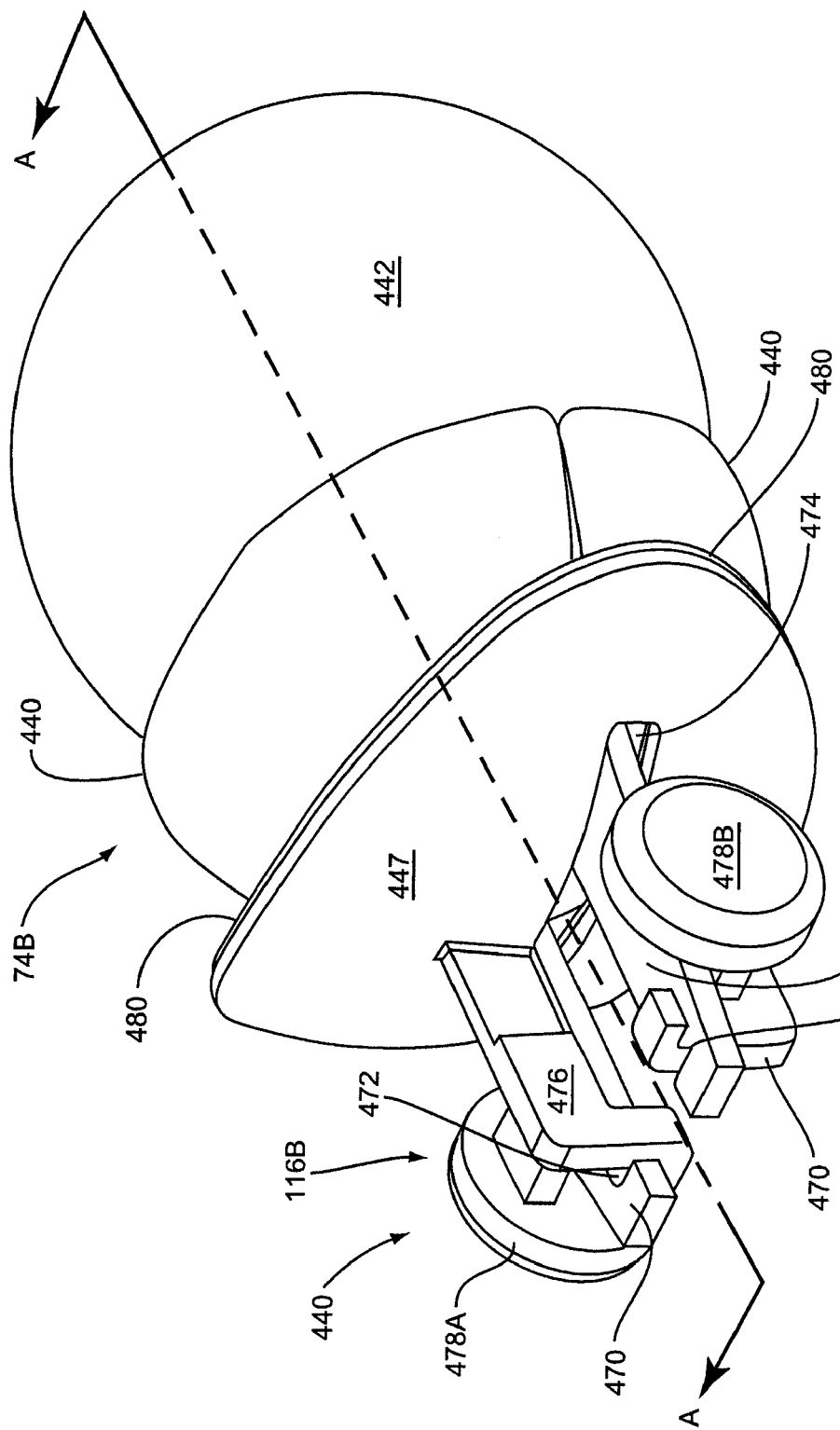
FIG. 27 illustrates an exploded perspective view of an alternative heat and force application device for treating MGD, according to one embodiment relating to the present invention.
Figure 28:
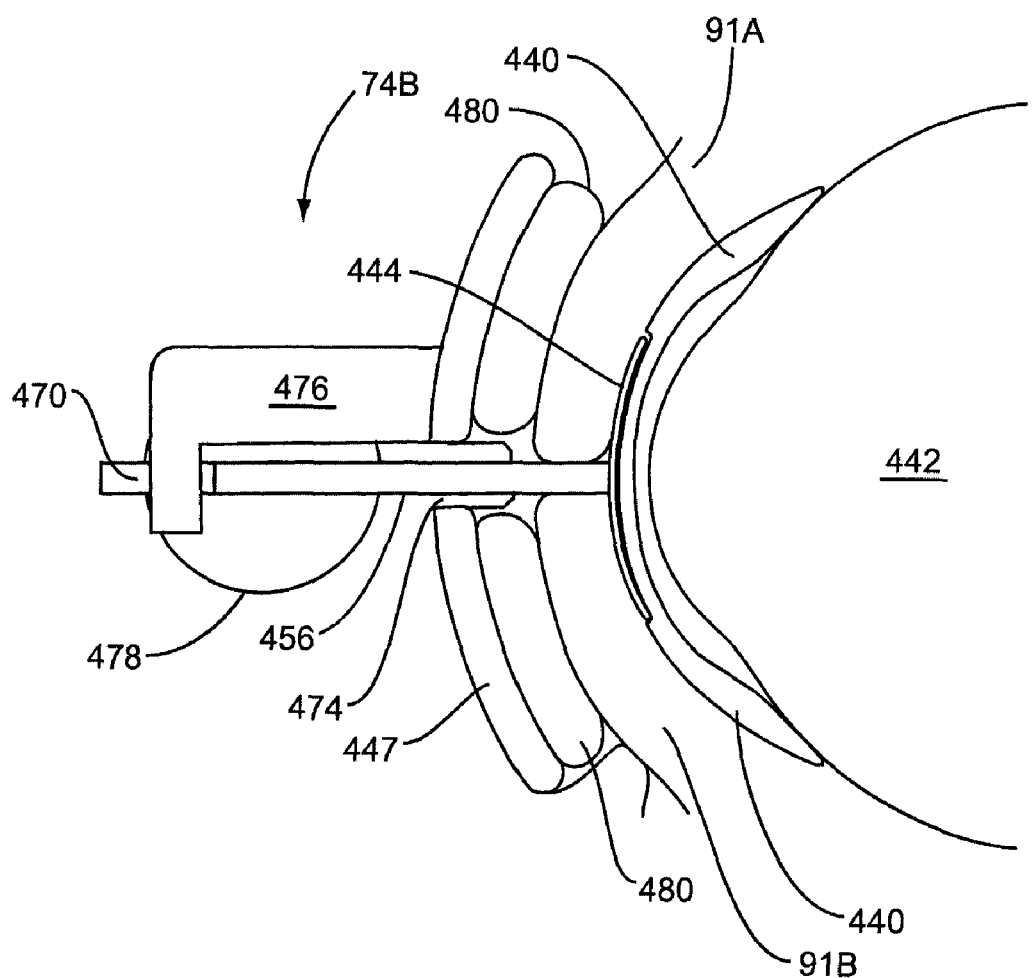
FIG. 28 is an illustration of the alternative heat and force application device according to a cross section taken along line A-A in FIG. 27, according to one embodiment relating to the present invention.

FIGS. 27-30 illustrate an alternative embodiment of the disposable component 74B that may be employed by the present invention to apply heat and/or force to the patient's eyelid as part of treating MGD. As illustrated in FIGS. 27 and 28, the apparatus comprises an insulator 440 and a means for applying force to the eyelid 91A, 91B, or lens 440 In the most basic form, the insulator 440 is concave in shape and mirrors the curvature of the eyeball 442, substantially similar to a contact lens. As employed herein, the term "insulator" is intended to include any component or material wherein there is greater resistance to thermal conduction or radiation towards the surface of the eye than towards the eyelid. Stated alternatively, in the insulator thermal energy radiates more easily towards the eyelid than towards the eyeball surface in order to minimize the possibility of causing injury to the eyeball 442. In the model that was constructed, the diameter was sufficient to more than cover the cornea or in the approximate range of 15 mm to 25 mm would be sufficient for most eyes assuming a corneal relief zone of approximately 16 mm. It will be noted however, that the diameter of the insulator 440 can vary beyond the ranges stated above.

Further, the insulator 440 is constructed from a biocompatible material such as polymethylmethacrylate (PMMA), or in the case of the prototype that was constructed, epoxy or other materials well known to those skilled in the art. The insulator 440 may be flexible, but ideally should be only minimally compressible, as will become clear from the discussion that follows. According to the invention, the insulator 440 is inserted on the surface of the eye 442, behind the rear surface of the eyelid and should include smooth edges so as not to scratch or cut either the eyelid or the eye. As used herein the term "eyelid" or "eyelids" is intended to include the upper lid and the lower lid, either in singly or in combination. The insulator 440 provides a back plate against which force may be applied. In limited circumstances when the obstruction in the meibomian gland channel is minimal, the meibomian gland may be cleared merely through the application of force externally applied to the eyelid, such as gentle finger press. More specifically, with the insulator 440 in place behind the eyelid, finger pressure is applied to the external surface of the eyelid, the eyelid being "sandwiched" between the finger and the insulator 440.

In other instances, the meibomian gland obstruction may be blocked to a degree greater than can be treated with simple pressure alone. In such cases it is necessary to apply thermal energy to the eyelid in order to loosen, break up, fracture, soften or liquefy at least a portion of the occlusion. Thermal energy may be applied by any one of the well known means for applying thermal energy such as modalities such as resistive, IR (infrared), ultrasonic heating, microwave, any one of the numerous "hot pads" that chemically produce an exothermic reaction or in the simplest form a hot compress. Experimentation has revealed that in order to be clinically effective the eyelid should be heated to a temperature of between about 35 degrees Celsius and 47 degrees Celsius. The length of time for which thermal energy (i.e. heat) is applied to the eyelid depends upon the extent that the obstruction blocks the meibomian gland channel as well as the composition of the obstruction. In very minor cases, heat may be applied to the eyelid for less than three minutes or even as little as five to fifteen seconds. On the other hand, extreme blockage may require as much as thirty minutes of heating to melt, loosen, or soften the obstruction prior to the application of force to the eyelid to express the softened obstruction. Experimentation has further revealed that the eyelids are efficient heat exchangers with circulating blood acting as the cooling mechanism and that the eyelid temperature returns to normal in less than two minutes at which time the obstruction re-hardens making extraction difficult. It is therefore necessary to apply the aforesaid expressive force to the eyelid within that time frame in order for the treatment to be successful. Thus, gentle finger pressure, preferably in a milking type action, to urge the obstruction upward and out of the meibomian gland orifice should be employed. Again, depending on the nature and location of the obstruction, mere compressive force may be effective in some instances.

The insulator 440 is inserted between the rear of the eyelid on the surface of the eyeball 442, as previously described. An eyecup 447 is employed to provide force and thus pressure to the eyelid. In one embodiment of the invention, thermal energy is applied as described above such as with a hot compress, and thereafter, within the one to two minute time frame, an eyecup (which may be unheated) is placed on the outer surfaces of the eyelid and force is applied thereto to express the softened obstruction. As illustrated, the eyecup mirrors the size and shape of the eyelids when closed.

Figure 29:
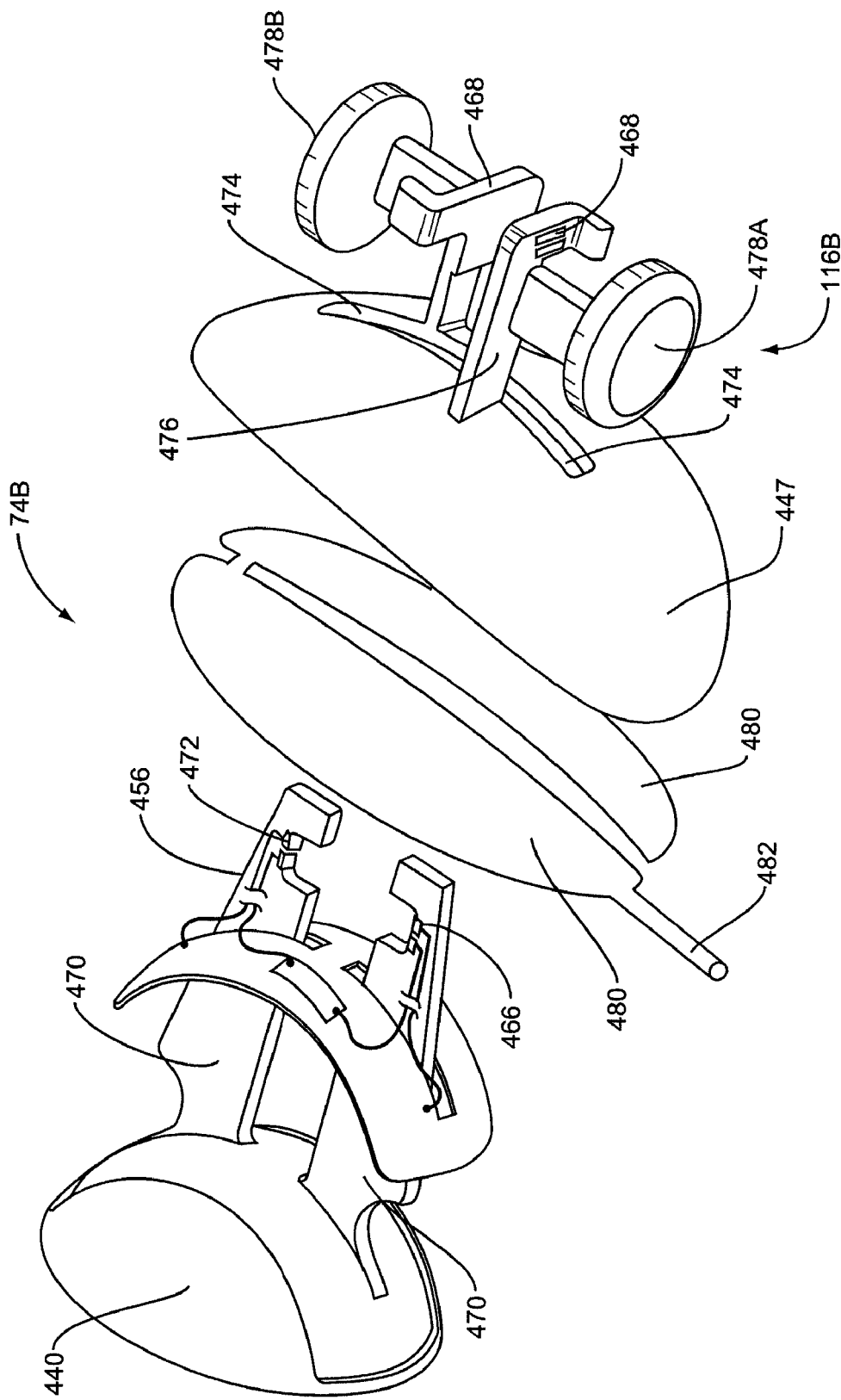
FIG. 29 illustrates an exploded view of the alternative heat and force application device according to FIG. 27, according to one embodiment relating to the present invention.
Figure 30:
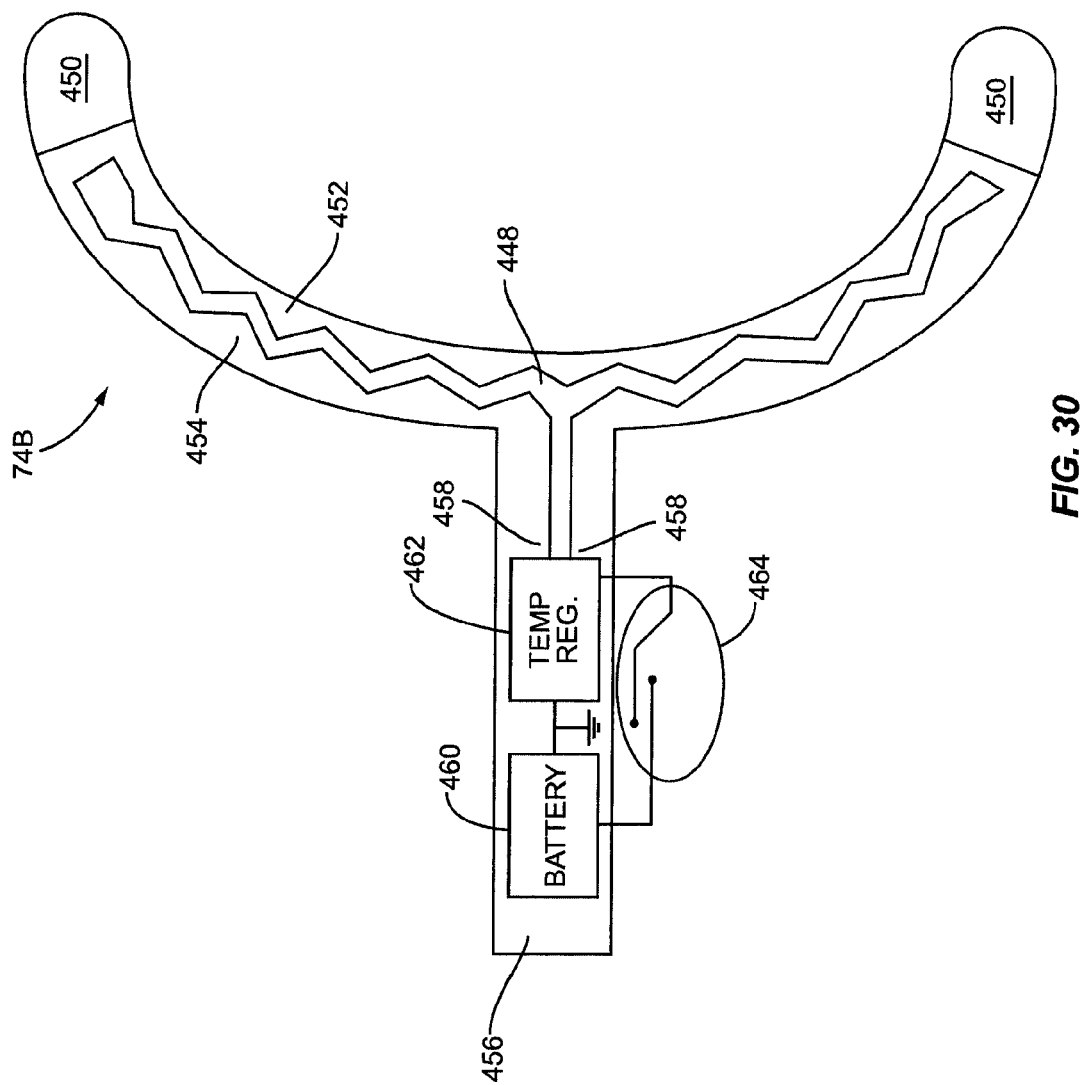
FIG. 30 illustrates a sectional view of the alternative heat and force application device according to FIG. 27, according to one embodiment relating to the present invention.

In FIGS. 29 and 30, the insulator 440 is provided with a heater means or heater 448. In this embodiment, the insulator 440 (e.g. lens) is concave in shape; however, the curvature is greater than that of the eyeball 442 so that an air pocket is formed between the insulator 440 and the eyeball 442. The air pocket provides additional insulation to prevent the heat applied from being conducted to the eyeball 442 surface during the treatment time. Further, ends 450 of the insulator 440 will be the only portion that actually physically contacts the eyeball 442. This section of the insulator 440 may be constructed of a biocompatible material that will not scrape or abrade the eyeball surface such as a soft rubber, plastic, or possibly even a soft metal. It will be noted that the lower surface 452 (i.e., that portion beneath the heater 448) and the upper surface 454 (i.e., that portion above heater 448) may be fabricated from different materials in order to minimize thermal conduction towards the eyeball and to facilitate thermal conduction towards the eyelid. One method of accomplishing the foregoing is to provide small air pockets in the lower surface 452 which would add additional insulation to that layer.

Heater 448 may be a resistive type heater, a thick film heater, or any one of a number of other types, such as a "flex circuit" (etched metal on flexible substrate) well known to those skilled in the art. As shown in FIG. 30, the insulator 440 is provided with a gripping means, handle, or platform 456 in which heater terminals 458 connect to the heater 448, battery 460, a thermal controller unit 462 (i.e. temperature regulator), and on/off switch 464 are located. The circuit comprising the heater 448, a power source such as battery 460, thermal controller unit 462, and on/off switch 464 are connected in series. The thermal controller unit/thermal regulator 462 is selected so that the temperature may be capped at an upper temperature threshold, such as at 47 degrees Celsius for example. The thermal controller unit 462 may also be designed to and turn off the circuit when that temperature is exceeded in order to prevent damage to the eye and surrounding tissue. In an alternate embodiment, the heater 448 may be connected to an "off device" power source through the use of appropriately placed contacts 466 and 468 (see FIG. 29).

Referring now back to the disposable component 74B of FIGS. 26-29, a pair of opposing spaced apart cantilevered arms 470 extend perpendicularly outward from the outer surface of the insulator 440 and together with handle 456 define means for coupling the eyecup 447 to the insulator 440. The respective arms 470 are tapered towards each other and each includes a notch 472 the purpose of which will become evident as the description proceeds. As best illustrated in FIG. 6, the heater 448 fits into a corresponding depression in the insulator 440 such that the two surfaces are flush in order to provide a smooth even surface for the inner eyelid to prevent rubbing and chaffing which upon blinking. Alternatively, the heater 448 could be embedded within insulator 440 or applied or connected to the surface thereof and with a smoothing coating overlay being added.

The eyecup 447 is adapted to overlie the outer surface of the eyelid, substantially conforms to the surface shape thereof and is adapted to cooperate with the insulator 440. The eyecup 447 includes a centrally located longitudinal slot 474. Positioned on above and below slot 474 and extending perpendicularly outward from the body of eyecup 447 is a pair of flexible spaced apart opposing cantilevered engagement arms 476 which include integrally molded finger grips or handles 478 and extensions 468. Positioned on the underside of eyecup 447 is a pair of diaphragms 480, which are in fluid communication with each other and which includes an inlet means or inlet 482. The diaphragms 480 are attached to the eyecup 447 via conventional means, such as glue for example (not shown). Further, it will be noted from the drawings that there is sufficient space provided between the diaphragms 480 to permit the arms 470 to pass therethrough.

While not illustrated, it will be noted that the eyecup 447 could be provided with a single diaphragm 480 with a hole defining an opening through which the arms 470 may pass. The diaphragms 480 may be fabricated from a biocompatible material such as polyurethane foam (open or closed cell), a sealed air balloon, or a gell-filled bladder. Again, depending upon the type and degree of obstruction, the diaphragms will vary in thickness and/or durometer. In an alternate embodiment, the diaphragms 480 may comprise bladders which may be fabricated from any flexible, expandable material such as rubber or plastic. However, it is preferred that the coefficient of expansion be linear with respect to the amount of fluid added. The bladders 480 may be partially filled or inflated with a constant amount of fluid or they may be provided with a rudimentary pump connected to inlet 482 such as is used with a perfume aerosolizer. The fluid is preferably air, but may also be a liquid such as water, saline, etc. Further, while not shown, the fluid may also be heated in order to assist in the softening of any meibomian gland obstructions which may be present. It will be noted that for any given patient, either or both of the insulator and fluid may be heated as required in order to soften any given obstructed meibomian glands.

While not illustrated, the bladders 480 could be fabricated in such a manner that as they inflate, pressure is applied which urges the softened gland obstructive material up the gland channel and out of the gland orifice to clear the gland. One method would be to increase the thickness of the bladders 480 such that there is less resistance (less thickness) to inflation near the bottom of the gland and the resistance increases (greater thickness) as one reaches the gland orifice.

In operation, the insulator 440 is placed on the sclera of the eye 442 in much the same manner as a contact lens is inserted. When properly positioned, arms 470 will extend outward between the eyelids 91A, 91B. The eyecup 447 is then positioned with the concavity facing the eyelid 91A, 91B such that the notch ends of arms 470 are inserted into slot 474. The eyecup 447 is directed along the arms 470 until notches 472 engage arm extensions 468 thus coupling the eyecup 447 to the insulator 440 and connecting contacts 466, 468. The heater 448 is then activated by switch 446 or other means to which the heated fluid in bladders 480 may be added simultaneously or serially for the preselected period of time, for example, two minutes. Thereafter, or simultaneously with the application of heat, the bladders 480 may be expanded which will urge the softened meibomian gland sebum up and out of the gland channel towards the gland orifice, thus, unblocking the gland. When treatment is complete, finger grips 478A, 478B are then pressed towards each other so that the eyecup 447 is free to slide off of and be removed from the arms 470. Thereafter, the insulator 440 is removed from the eyeball 442 and treatment is complete.

It will be noted that various mechanisms to lock the insulator to the eyecup could be employed, such as a ratchet type mechanism on arms 470 which is released upon compression of finger grips 478A, 478B, a press fit of the arms 470 into slot 474 as well as other mechanisms well known to those skilled in the art, not discussed herein. Manual control and release and force as well as manual adjustment of the eyecup may be employed during treatment and/or until expression of the obstruction or occlusion in the meibomian glands is achieved. While not specifically required, it is preferable that the locking mechanisms be near "zero insertion" force in order to minimize the potential for eye injury. Further, different eyecups with different shapes and different rigidities may be employed. Some of these alternate disposable components 74 are disclosed in FIGS. 31-40 of the present application and will be discussed below.

Figure 31A:
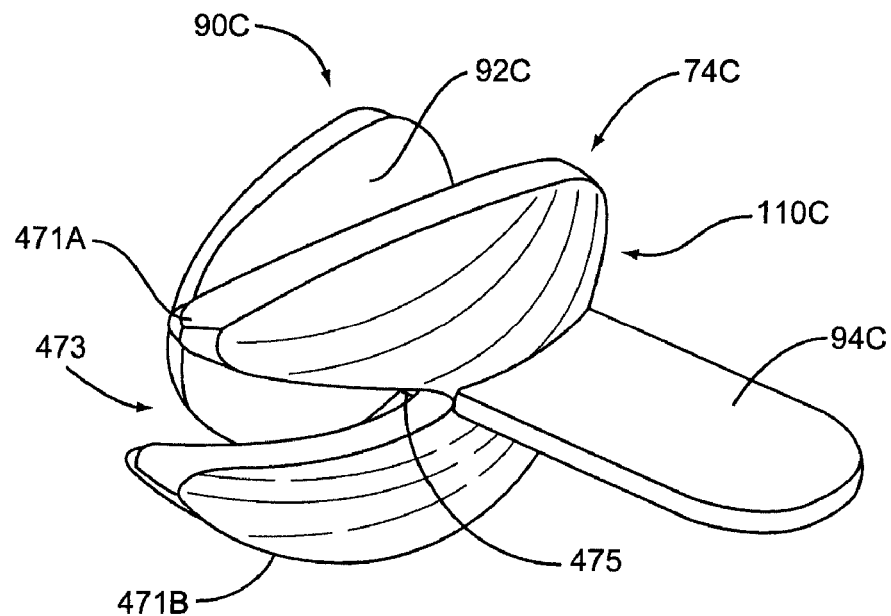
Figure 31B:
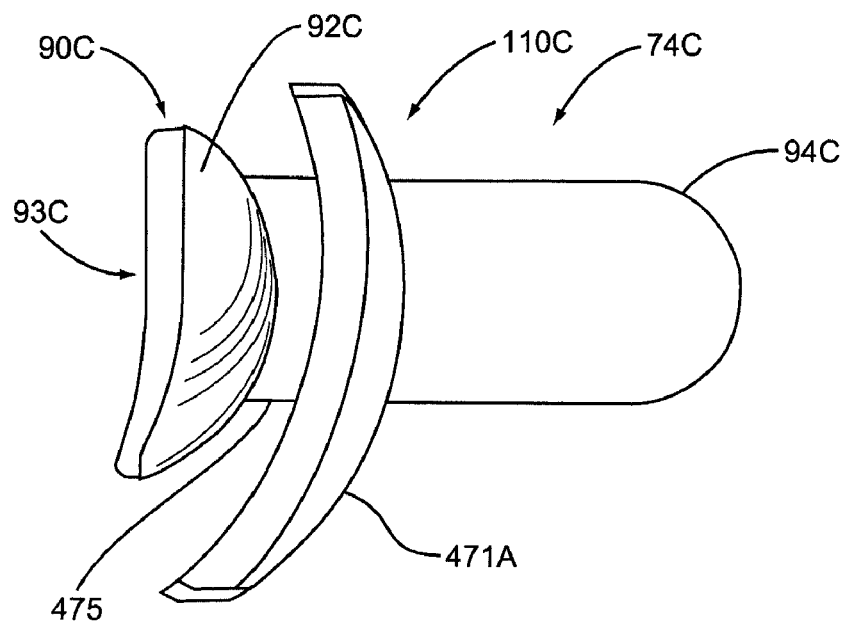

FIGS. 31A and 31B illustrate another alternative embodiment of the disposable component 74C that may be employed by the present invention to apply heat and/or force to the patient's eyelid as part of treating MGD. In this embodiment, the lid warmer 90C is firmly affixed to the eyecup 110C without the ability to separate the two or make adjustments to change the distance between the lens 90C and the eyecup 110C. The only moveable component is an inflatable bladder 114C that is controlled to apply a force to the outside of the patient's eyelid. Such a disposable component 74C may be employed as simpler to install and use by technicians during therapy since no adjustments to the position of the eyecup 110C with respect to the lid warmer 90C are necessary.

Figure 32:
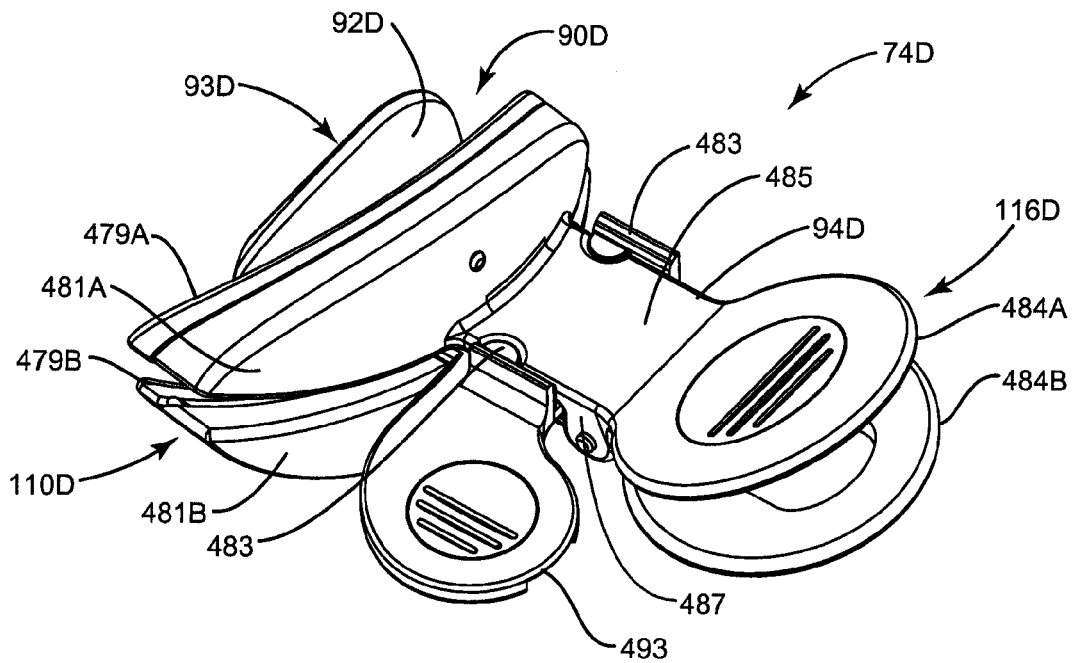
FIG. 32 is an illustration of another alternative heat and force application device, according to one embodiment of the present invention.

The disposable component 74C comprises a lid warmer 90C in the form of a lens similar to previously discussed lid warmer 90A, 90B. The lid warmer 90C contains a heating element (not shown) to apply heat to the inside of the patient's eyelid when the inside surface of the lens 93C is placed on top of the patient's eye. The lid warmer 90C also contains a lid warmer platform 94C to allow a technician or doctor to grasp the lid warmer 90C and install it over top of the patient's eye. An eyecup 110C is also provided to apply force to the outside of the patient's eyelid. The eyecup 110C is formed by an upper and lower concave cups 471A, 471B. An opening 473 is provided between the two cups 471A, 471B about a horizontal center line of the lens 90C for ease in making adjustments and because the meibomian glands are located above and below the center of the lens. Thus, it may not be necessary to apply force in the center of the eyecup 110C where the upper and lower eyelids of the patient meet together when the disposable component 74C is installed. The lid warmer platform 94 is securely fixed to the eyecup 110C at an interface section 475 to provide a fixed distance between the inside of the eyecup 110C and the outside surface of the lens 92C FIG. 32 illustrates another alternative embodiment of the disposable component 74D that may be employed by the present invention to apply heat and/or force to the patient's eyelid as part of treating MGD. In this embodiment, the eyecup 110D contains a latching mechanism 116D that allows the eyecup 110D to be affixed to the lid warmer platform 94D and the distance between an inflatable bladder 479A, 479B and the outside surface of the lens 92D to be adjusted.

In this embodiment, the eyecup 110D design contains split upper and lower eyecups 481A, 481B similar to the eyecup 110C design illustrated in FIG. 31, except that the eyecups 481A, 481B that support membranes or bladders 479A, 479B to apply force to the patient's eyelid are completely separated from each other. The split eyecups 481A, 481B allow the upper eyecup 481A to be lifted independent of the lower eyecup 481B to be able to release the eyecup 110D from the lid warmer 94D. In this regard, the lid warmer platform 94D contains holders 483 that are adapted to secure an eyecup platform 485 attached to the eyecup 110D to secure the eyecup 110D to the lid warmer 94D. The eyecup platform 485 contains a clamp 484A hingedly attached to the lid warmer platform 94D via hinge 487. The lid warmer platform 94D contains an opposing clamp 484B, such that when the clamps 484A and 484B are squeezed together, the eyecup platform 485 is released from the holders 483 to release the eyecup 110D from the lid warmer 94D. The lid warmer platform 94D also contains a grip handle 493 that can be held while the clamps 484A, 484B are squeezed to hold the lid warmer 94D when the eyecup 110D is released.

Figure 33:
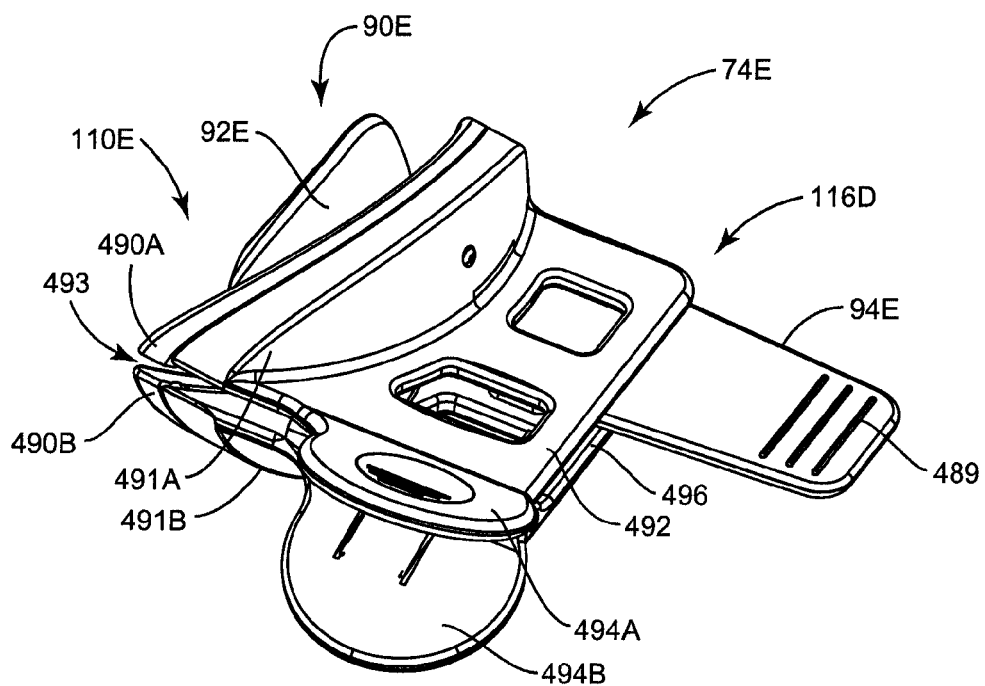
FIG. 33 is an illustration of another alternative heat and force application device, according to one embodiment of the present invention.

FIG. 33 illustrates another alternative embodiment of the disposable component 74E that may be employed by the present invention to apply heat and/or force to the patient's eyelid as part of treating MGD. This embodiment is similar to the disposable component 74E of FIG. 32, except that the latching mechanism 116E to attach and release the eyecup 110E from the lid warmer 90E is provided completely as part of the eyecup 110E. The latching mechanism 116E allows the eyecup 110F to be affixed to the lid warmer platform 94E and the distance between an inflatable bladder 490A, 490B and the outside surface of the lens 92E to be adjusted.

In this embodiment, the eyecup 110E design contains a split upper and lower eyecups 491A, 491B similar to the eyecup 110E design illustrated in FIG. 32. The upper and lower eyecups 491A, 491B support membranes 490A, 490B that apply force to the patient's eyelid. Eyecup platforms 492, 496 extend from the eyecup 110E and contain clamps 494A, 494B hingedly attached to each other via hinge 493. When the clamps 494A and 494B are squeezed together, the eyecup platforms 492, 496 move away from each other to release the lid warmer platform 94E. The lid warmer platform 94E was compressed between the eyecup platforms 492, 496 when the clamps 494A, 494B were not being squeezed to secure the lid warmer 90E to the eyecup 110E. The eyecup 110E can be adjusted with respect to the lid warmer 90E by compressing the clamps 494A and 494B and moving the eyecup platforms 492, 496 to the desired location on the lid warmer platform 94E. The lid warmer platform 94E may also contain a grip 489 at its end to provide better gripping of the lid warmer platform 94E when the eyecup 110E is adjustably placed at the desired location along the lid warmer platform 94E.

Figure 34:
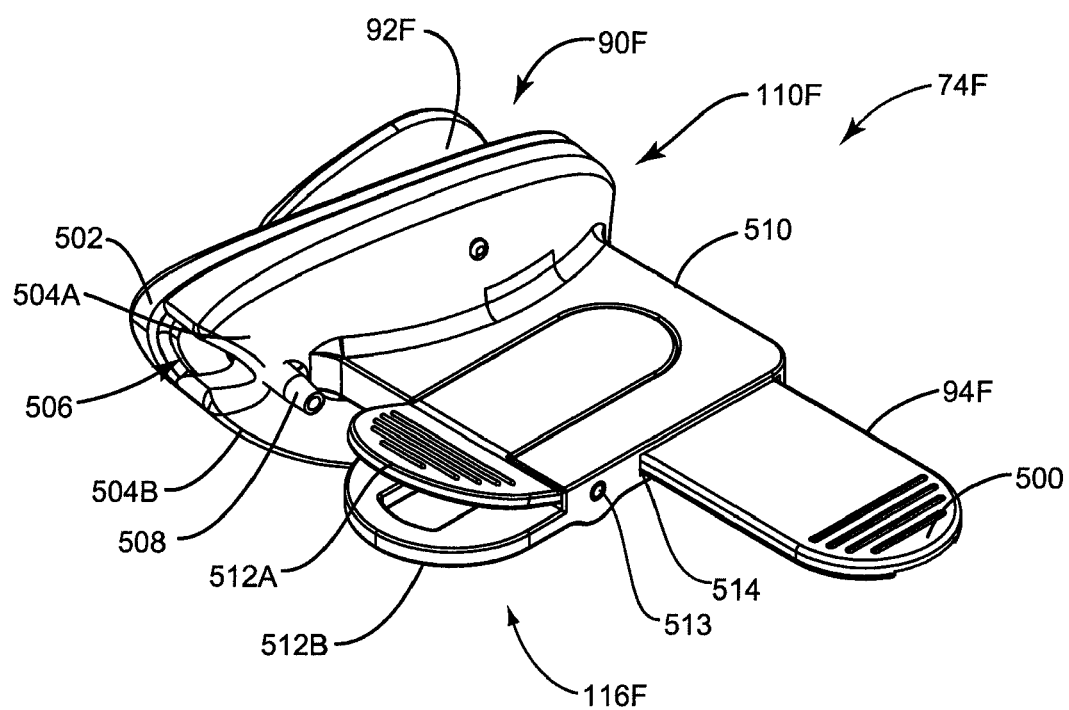
FIG. 34 is an illustration of another alternative heat and force application device, according to one embodiment of the present invention.

FIG. 34 illustrates another alternative embodiment of the disposable component 74F that may be employed by the present invention to apply heat and/or force to the patient's eyelid as part of treating MGD. This embodiment has a latching mechanism 116F similar to the disposable component 74E of FIG. 33, except that the eyecup 110F is one piece having an eyecup 504 that does not contain separable components. The latching mechanism 116F allows the eyecup 110F to be affixed to the lid warmer platform 94F and the distance between an inflatable bladder 502, 490B and the outside surface of the lens 92F to be adjusted. The eyecup 110F contains a pneumatic interface 508 to allow the controller 72 to inflate the bladder 502.

The eyecup 110F also contains an eyecup platform 510 that supports the latching mechanism 116F. The eyecup platform 510 supports eyecups 504A, 504B that support a membrane or bladder 502 to apply force to the patient's eyelid. The latching mechanism 116F is comprised of eyecup clamps 512A, 512B that are hingedly attached to each other via hinge 513. When the clamps 512A and 512B are squeezed together, an orifice 514 in the eyecup platform 510I is unlocked to allow the lid warmer platform 94F to be moved transversely along the eyecup platform 510F. In this manner, the lid warmer 94F can be affixed to the eyecup 110F and moved to the desired distance from the eyecup 110F. If the lid warmer 90F and its platform 94F are pulled away from the eyecup 110F, the lid warmer 90F can be released from the eyecup 110F when platform 94F is pulled through the orifice 514. Just as the platform 94F in FIG. 33, the lid warmer platform 94E may also contain a grip 500 at its end to provide better gripping of the lid warmer platform 94F when the eyecup 110F is adjustably placed at the desired location along the lid warmer platform 94F.

Figure 35:
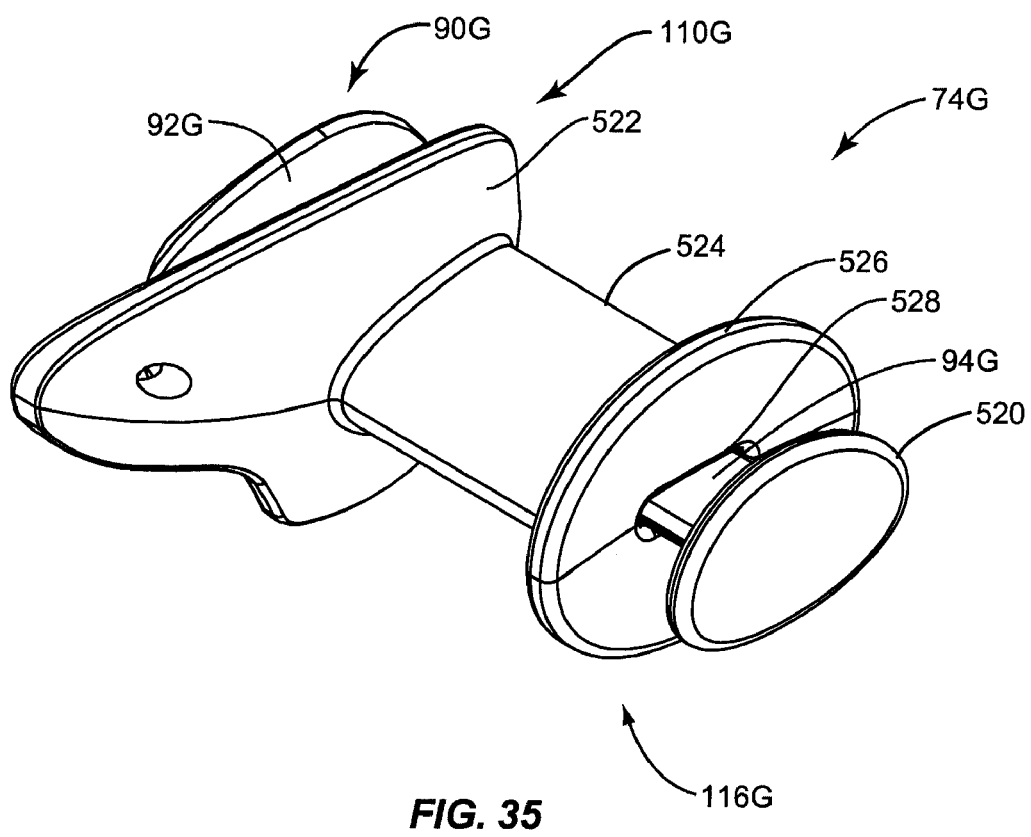
FIG. 35 is an illustration of another alternative heat and force application device, according to one embodiment of the present invention.

FIG. 35 illustrates another alternative embodiment of the disposable component 74G that may be employed by the present invention to apply heat and/or force to the patient's eyelid as part of treating MGD. This embodiment has a latching mechanism 116G that operates similar to the manner in which a syringe works. The eyecup 110G is formed from one piece. An outer surface of the eyecup 522 is attached to a cylindrically-shaped tube 524 having a platform 526 on its end. The lid warmer platform 94G extends through the tube 524 and an orifice 528 through the platform 526 and contains a lid warmer platform 94G in the form of a plunger 520 on its end that rests against the platform 524 when fully pushed down or engaged. To move the eyecup 90G farthest from the lid warmer 90G, the plunger 520 is fully engaged forward or downward. To move the lid warmer 90G closer to the eyecup 110G, the plunger 520 is pulled upward or backwards. The plunger 520 controls the movement of the lid warmer 90G and thus the distance between the lid warmer 90G and the eyecup 110G to administer therapy.

Figure 36A:
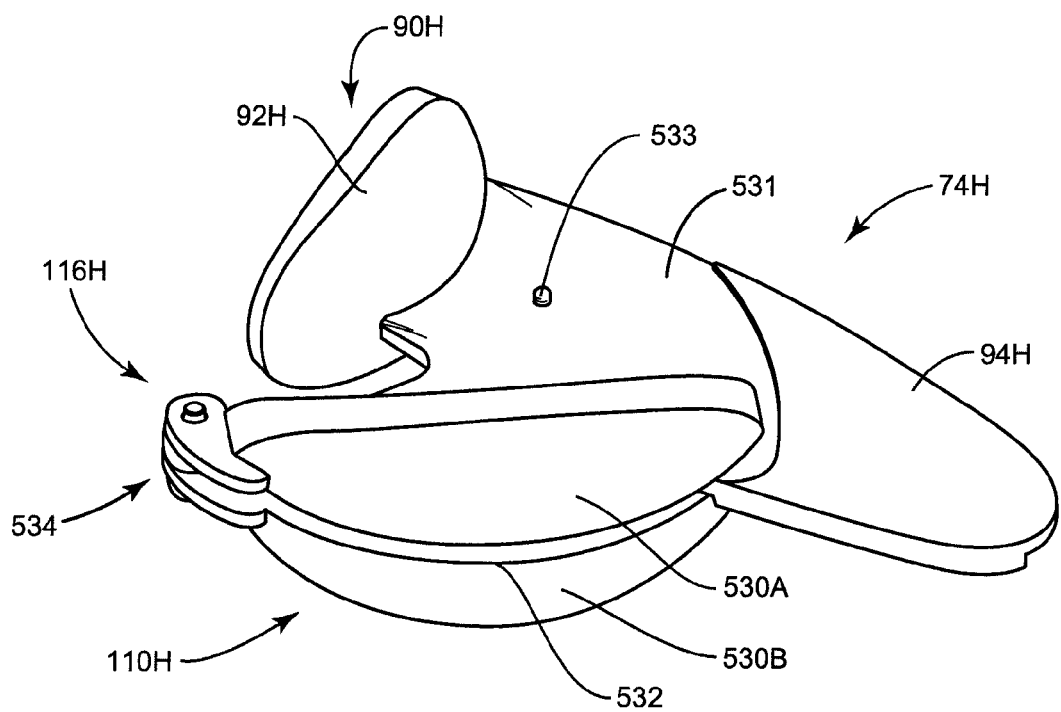
FIGS. 36A and 36B are illustrations of another alternative heat and force application device, according to one embodiment of the present invention.
Figure 36B:
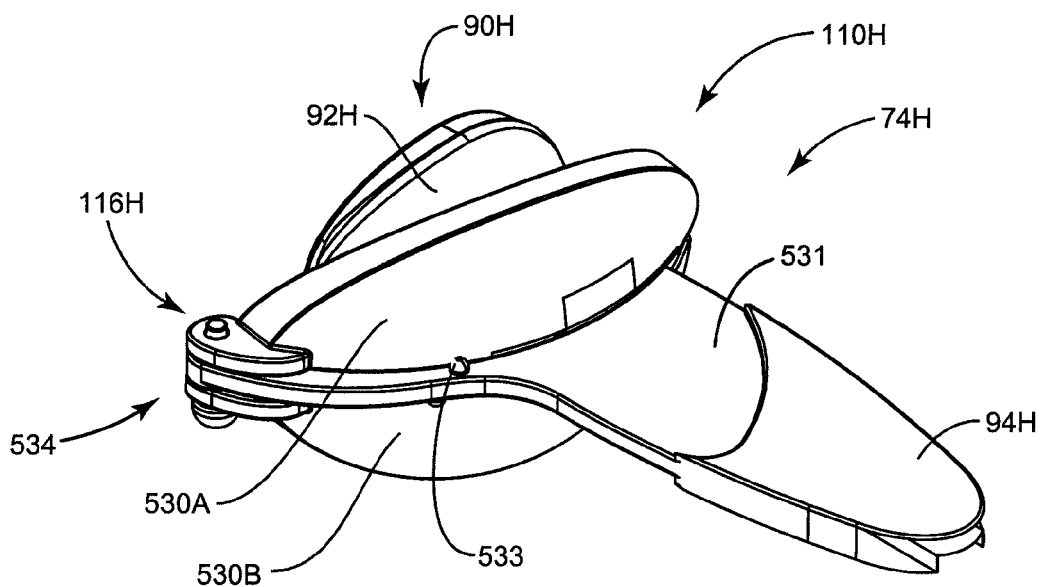

FIGS. 36A and 36B illustrate another alternative embodiment of the disposable component 74H that may be employed by the present invention to apply heat and/or force to the patient's eyelid as part of treating MGD. This embodiment is similar to the disposable component 74E of FIG. 33 in that separate upper and lower eyecups 530A, 530B are provided to apply force to the upper and lower eyelid of the patient. However, both eyecups 530A, 530B do not have to be engaged. Each can be engaged separately. For example, it may be desired to treat the meibomian glands in only the upper or lower eyelid of a patient and not both at the same time. In this manner, the lid warmer platform 94H contains a hinge 534. The upper and lower eyecups 530A, 530B are attached to the hinge 534 such that they can rotate over the lid warmer platform 94H. When not in use, the eyecups 580A, 580B can be rotated away from the lid warmer platform 94H as illustrated in FIG. 36A. The lid warmer platform 94E contains a grooved surface 531 that allows the eyecups 530A, 530B to be rotated about hinge 534 and moved to the outside surface of the lens 92H as illustrated in FIG. 36B. When in use, the eyecups 580A, 580B move past a notch 533 in the lid warmer platform 94H to lock in place.

Figure 37:
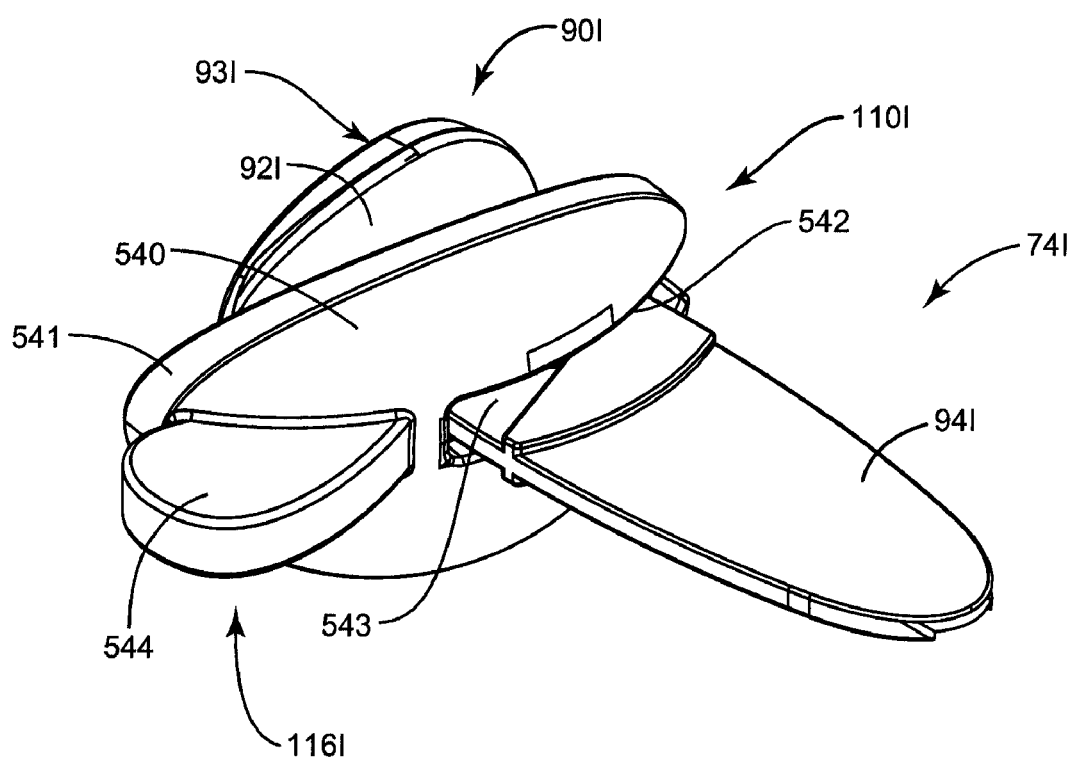
FIG. 37 is an illustration of another alternative heat and force application device, according to one embodiment of the present invention.

FIG. 37 illustrates another alternative embodiment of the disposable component 74I that may be employed by the present invention to apply heat and/or force to the patient's eyelid as part of treating MGD. In this embodiment, the eyecup 110I is formed by eyecup 540 that supports a membrane or bladder 541 to apply force to the patient's eyelid. The eyecup 540 contains an opening 542 through the lid warmer platform 94I and extends through to attach the eyecup 110I to the lid warmer platform 94I when the disposable component 74I is installed. The lid warmer platform 94I contains a thickened surface 543 which locks the lid warmer platform 94I into the split 542 and prevents the eyecup 110I from moving about the lid warmer platform 94I for a secure fit when in use. A handle 544 is also attached to the eyecup 540 to allow a technician to hold the eyecup 540 when adjusting the lid warmer 901 with respect to the eyecup 540.

Figure 38A:
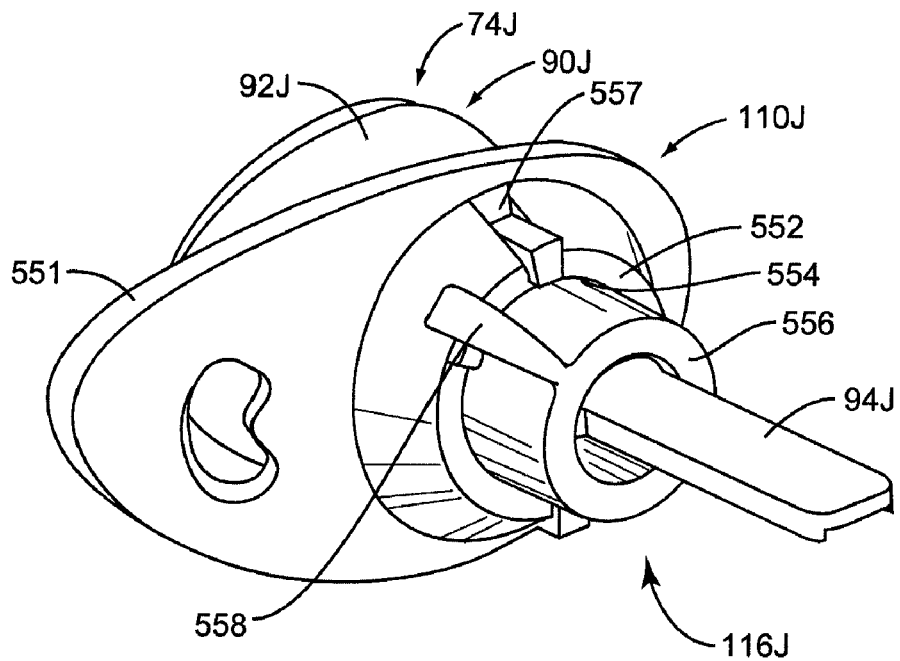
FIGS. 38A and 38B are illustrations of another alternative heat and force application device, according to one embodiment of the present invention.
Figure 38B:
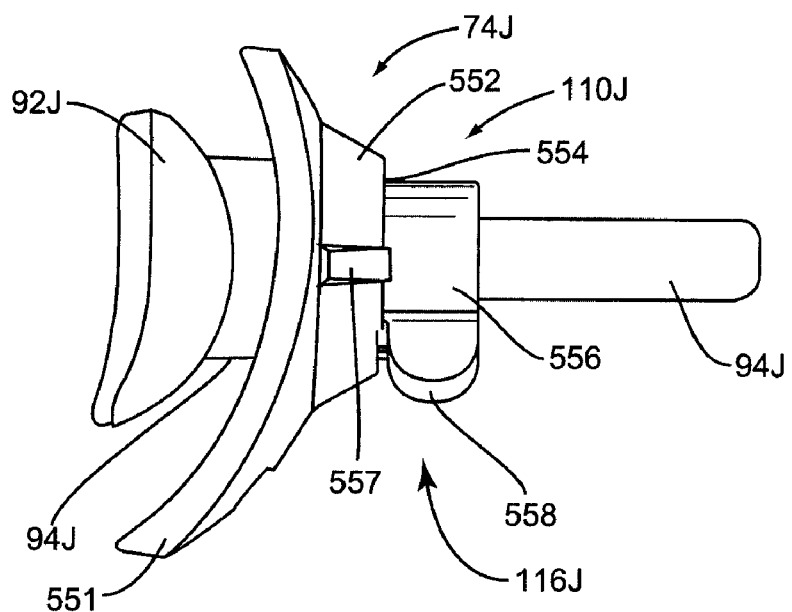

FIGS. 38A and 38B illustrate another alternative embodiment of the disposable component 74J that may be employed by the present invention to apply heat and/or force to the patient's eyelid as part of treating MGD. In this embodiment, the eyecup 110J is provided as one piece. The eyecup 110J supports a membrane or bladder 551 to apply force to a patient's eyelid and contains a ridge 552 through which an orifice 554 protrudes through. A bladder advance mechanism 554 is placed through the orifice 554, wherein the lid warmer platform 94J extends through th orifice 554 in the bladder advance mechanism 556. The bladder (not shown) is attached to the bladder advance mechanism 556. When it is desired to advance the bladder (not shown) to the patient's eyelid to apply force, the bladder advance mechanism 556 is rotated such that notch 558 can fit inside a groove 557 on the ridge 552 to allow the bladder advance mechanism 556 to move forward through the orifice 552 towards the lid warmer 90J and lock in place. When desired to move the bladder away from the lid warmer 90J, the bladder advance mechanism 556 is pulled back so that the notch 558 is removed from the groove 557 and can be rotated away from the groove 557 to be supported by the ridge 552.

Figure 39:
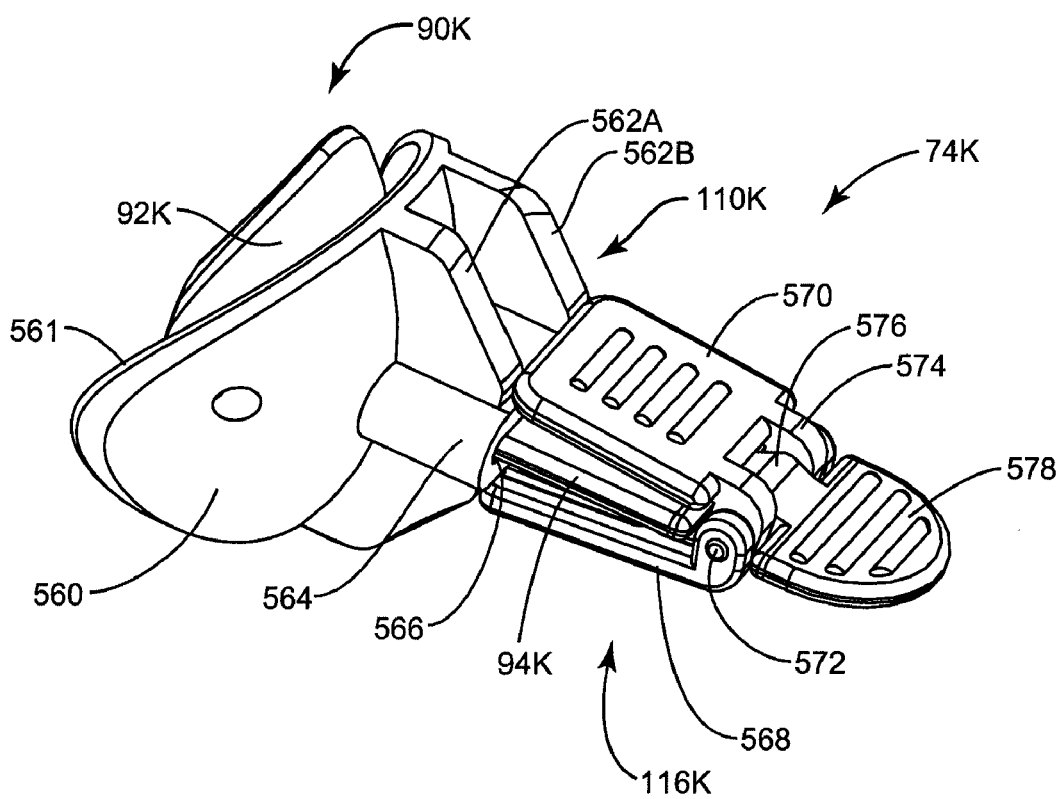
FIG. 39 is an illustration of another alternative heat and force application device, according to one embodiment of the present invention.

FIG. 39 illustrates another alternative embodiment of the disposable component 74K that may be employed by the present invention to apply heat and/or force to the patient's eyelid as part of treating MGD. In this embodiment, the eyecup 110K is provided as one piece. The eyecup 110K supports a membrane or bladder 561 that applies force to the patient's eyelid. The eyecup 110K contains an outer surface 560 that contains rib structures 562A, 562B to support an orifice chamber 564 having an orifice 566 through which the lid warmer platform 94K extends to attach the eyecup 110K to the lid warmer 90K. Squeezable eyecup platforms 568, 570 are attached on each side of the orifice 566 to the rib structures 562A, 562B on one end and to a common hinge 572 on their other end. When the eyecup platforms 568, 570 are squeezed, it allows the lid warmer platform 94K to be move transversally through the orifice 566. When the eyecup 110K is to be placed against the patient's eyelid, a grip 578 is pulled such that a neck 576 of the lid warmer platform 94K is inserted and locked down into a groove 574 formed in the lower eyecup platform 570.

Figure 40:
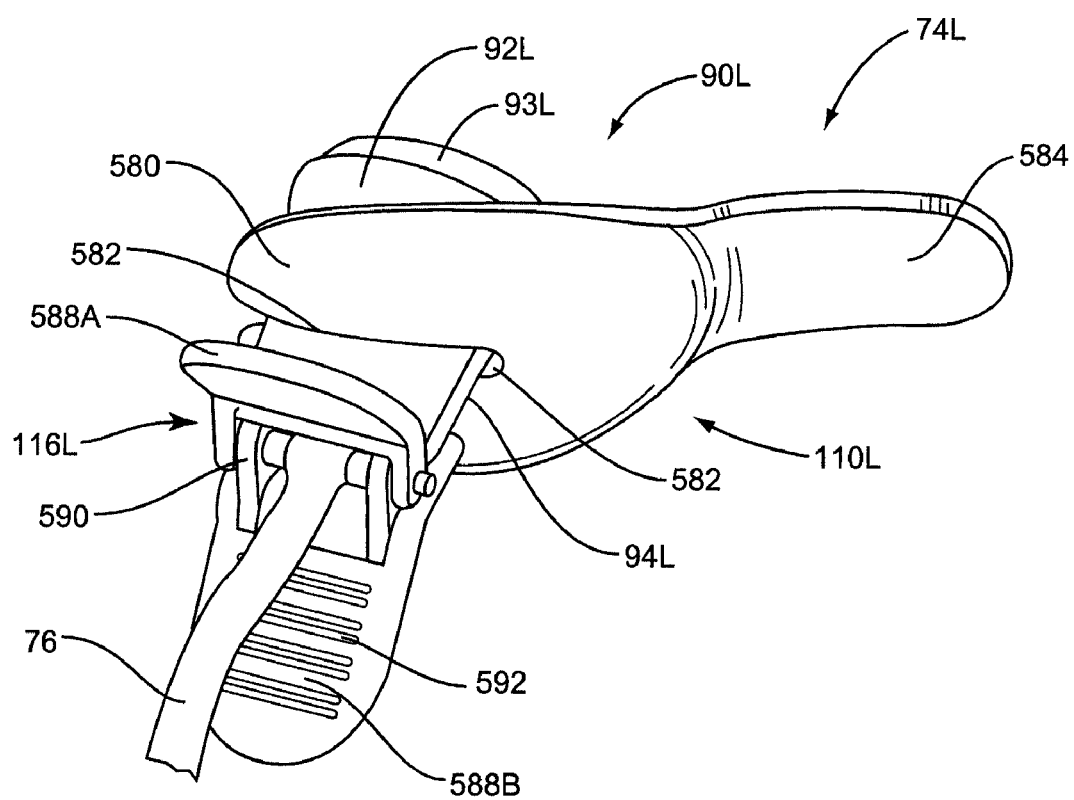
FIG. 40 is an illustration of another alternative heat and force application device, according to one embodiment of the present invention.

FIG. 40 illustrates another alternative embodiment of the disposable component 74L that may be employed by the present invention to apply heat and/or force to the patient's eyelid as part of treating MGD. In this embodiment, the eyecup 110L and lid warmer 94L are provided as two separate pieces. Finger tabs 588A, 588B, attached to hinge 590, can be depressed to allow room for an opening 482 in the eyecup 110L to be inserted over top the lid warmer platform 94L along opening 582 in the eyecup 580 where desired. When the eyecup 110L is placed on the lid warmer platform 94L in the desired location, the finger tabs 588A, 558B are released and the tabs 588A, 588B position and hold the eyecup 110L in place.

Figure 41:
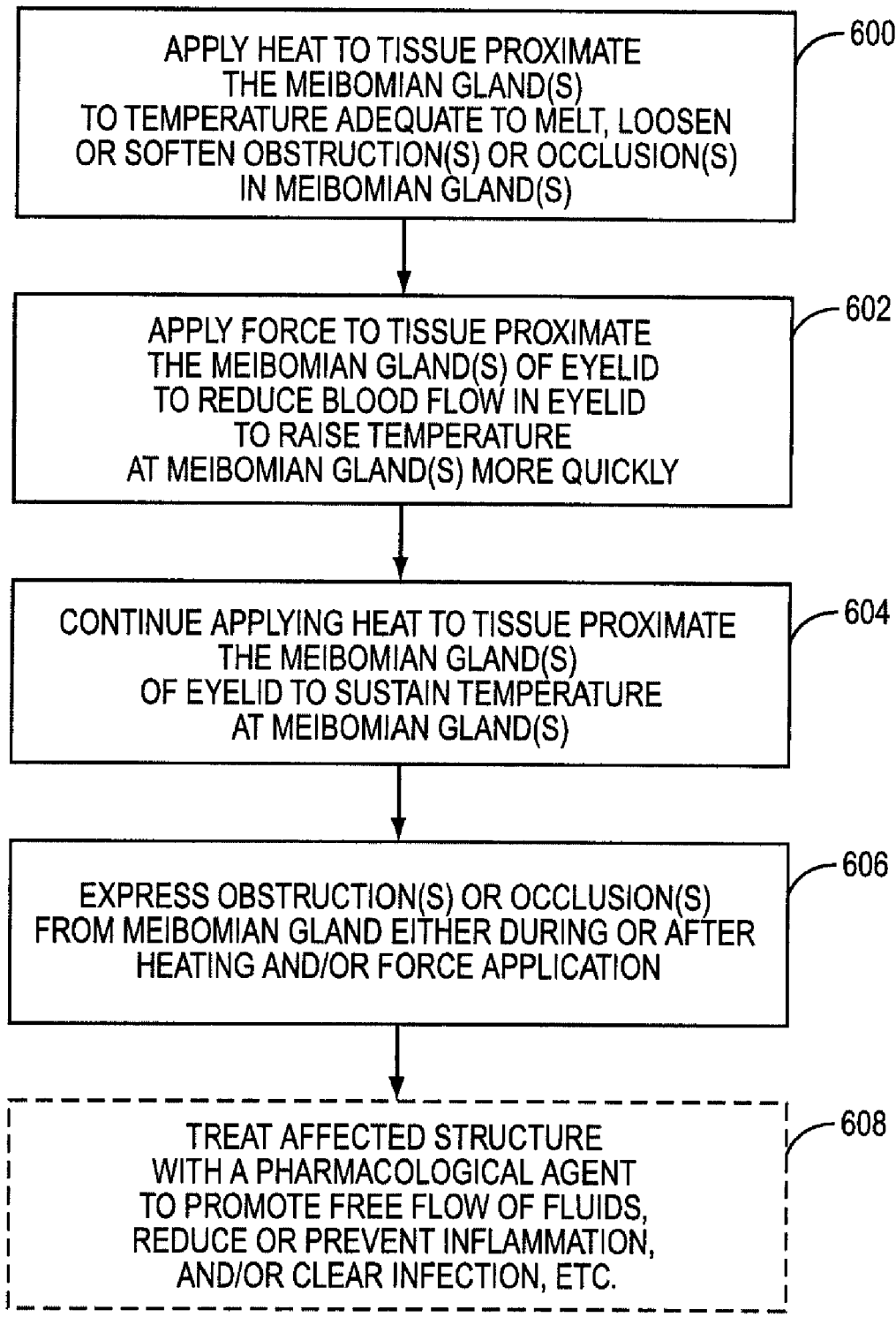
FIG. 41 is a flowchart illustrating an alternative meibomian gland treatment employing applying heat and force to tissue proximate the meibomian gland to reduce heat loss when heat is applied to melt, loosen, or soften obstructions or occlusions.

Although the present application discusses and provides devices for applying heat on the inside of the eyelid and force to the outside of the eyelid to treat MGD, other configurations are possible. Heat and force may be applied in a number of different combinations and manners to treat MGD. For example, FIG. 41 illustrates an alternative embodiment of the present invention for applying heat and force to tissue proximate a patient's meibomian gland to treat MGD. In this embodiment, heat is applied and force is applied. Heat is applied provide conductive heat transfer to the meibomian glands to the desired temperature level (step 600). For example, heat may be applied to raise the temperature at the inside of the eyelid between 43-47 degrees Celsius. The heat may also be regulated, meaning that a heating means or element is controlled to be within the temperatures and means that are safe for the eyelid and at a sufficient temperature for melting, loosening, or softening an occlusion or obstruction in the meibomian gland.

A force may also be applied to tissue proximate the patient's meibomian gland to increase the efficiency of heat transfer. As previously described, the application of force towards the heat source with the patient's eyelid "sandwiched" therebetween provides greater surface contact between the heat source and the eyelid for more efficient conductive heat transfer. Further, the application of force reduces blood flow in the eyelids to reduce convective heat loss through the eyelids and allow the temperature at the meibomian glands to not only rise to higher levels, but do so more quickly and efficiently (step 602).

The heat and/or force may be maintained for a period of time sufficient to raise the temperature at the meibomian glands sufficient to melt, loosen, or soften the obstructions or occlusions (step 604). The force may be maintained after heat is removed, or vice versa depending on the treatment technique desired. Maintaining force after heat is removed may reduce convective heat loss at the meibomian glands and thus keep the temperature level at the meibomian glands to the therapeutic levels for more time than if the force was removed. Maintaining heat without maintaining force may be employed to allow blood flow in the eyelids, such as between successive treatments. For example, it may be desirable to maintain heat to lessen the total amount of treatment time while applying and removing force between treatments. Also, it may not be necessary to apply significant amounts of force, or for the same duration as application of heat, if the obstruction or occlusion is located in close proximity to the lid margin rather than in the deeper portions of the meibomian gland. Thereafter, either during heating and/or the application of force or after either, obstructions or occlusions in the meibomian glands may be expressed so that sebum flow is restored from the glands to establish a sufficient lipid layer (step 606).

The force may be regulated, meaning that a force generating means is controlled to be within the pressure ranges that are safe to be applied to tissue proximate the meibomian glands and at sufficient pressure to allow the temperature at the meibomian gland to be raised sufficiently. The force may be applied during heating, after heating, or both during and after heating. In either case, the force may assist in expressing occlusions or obstructions when in a loosened, softened, or melted state from the meibomian glands. The force may include vibratory type forces, including those generated mechanically or using fluid type devices or mechanisms. The level of force needed to express obstructions or occlusions in the glands may be greatly reduced when heat is applied to the obstructions or occlusions to place them in a melted, softened, or loosened state.

The application of force can also stimulate the movement of fluids or suspensions of occlusions or obstructions from the glands. The present invention can be used with devices which generally apply a regulated force or milking action to the eyelid to express the fluids or suspensions or to otherwise mechanically stimulate the movement of fluids from the glands. In some instances, a small, gentle, continuous force applied to the eyelid will assist in expression of the fluids and suspensions. Vibration can also be used when applying force simultaneously or immediately after the heating to further assist in the expression.

Any device may be employed to generate heat on the outside of the patient's eyelid, including those described herein. Other devices may be employed, such as the apparatus disclosed in U.S. Patent Application Publication No. 2007/1016254, entitled "Method and apparatus for treating gland dysfunction employing heated medium," and incorporated herein by reference in its entirety. In this application, an apparatus is employed to apply heat to the outside of the patient's eyelid via heated fluid transfer. Further, a gas may be employed as opposed to fluid to apply heat to the patient's eyelid.

Just as discussed above in the flowchart of FIG. 6, where only heat is applied, regulated heat can include controlling heat according to a temperature profile. The temperature profile may be a constant temperature, include ramp-ups, ramp-downs, peaks and valleys. Further, the temperature profile may include heat pulses or be modulated with various characteristics, including the use of pulse width modulation (PWM) techniques. The use of modulated heat may allow the temperature to be raised even higher at the eyelid without damage to the patient's eyelid since the increased temperatures are applied for shorter periods of time. Obstructions or occlusions in the meibomian glands may have melting, loosening, or softening points that are beyond temperatures that may be applied without the use of modulated heat. The temperature needed to melt, loosen, or soften obstructions or occlusions may depend on how keratinized the obstruction or occlusion is. Not all obstructions or occlusions have the same melting, loosening, or softening points. By example only, elevated temperatures between 47 and 55 degrees Celsius may be possible when applying modulated heat, especially if the eyelid has been anesthetized.

The regulated heat can be maintained at a therapeutic temperature for a treatment period. The treatment period can be approximately 1 to 10 minutes for example, since the application of force may reduce the amount of time it takes for the heat source to raise the temperature at the meibomian glands to the desired level. The heat could also be repeatedly applied and maintained for a desired period of time to keep the occlusion or obstruction in a melted, loosened, or softened state. Either during or after such treatment by regulated heat, mechanical expression of lipids and other fluids from the meibomian glands has been found to clear obstructions which have essentially melted or been placed in a suspension state (by virtue of melting materials binding solids together).

Optionally, after expression of the occlusions or obstructions is performed (step 606), an optional pharmacological agent may be applied to the meibomian gland to promote the free flow of sebum and/or reduce or prevent inflammation or infections of the eye or eyelids (step 608). The previous discussion in the flowcharts of FIGS. 6 and 8 regarding use of pharmacological agents above is equally applicable for this embodiment and thus will not be repeated here. Those compounds are illustrative examples of appropriate pharmacological agents, but those skilled in the art will appreciate that other pharmacological compounds may be utilized.

Figure 42:
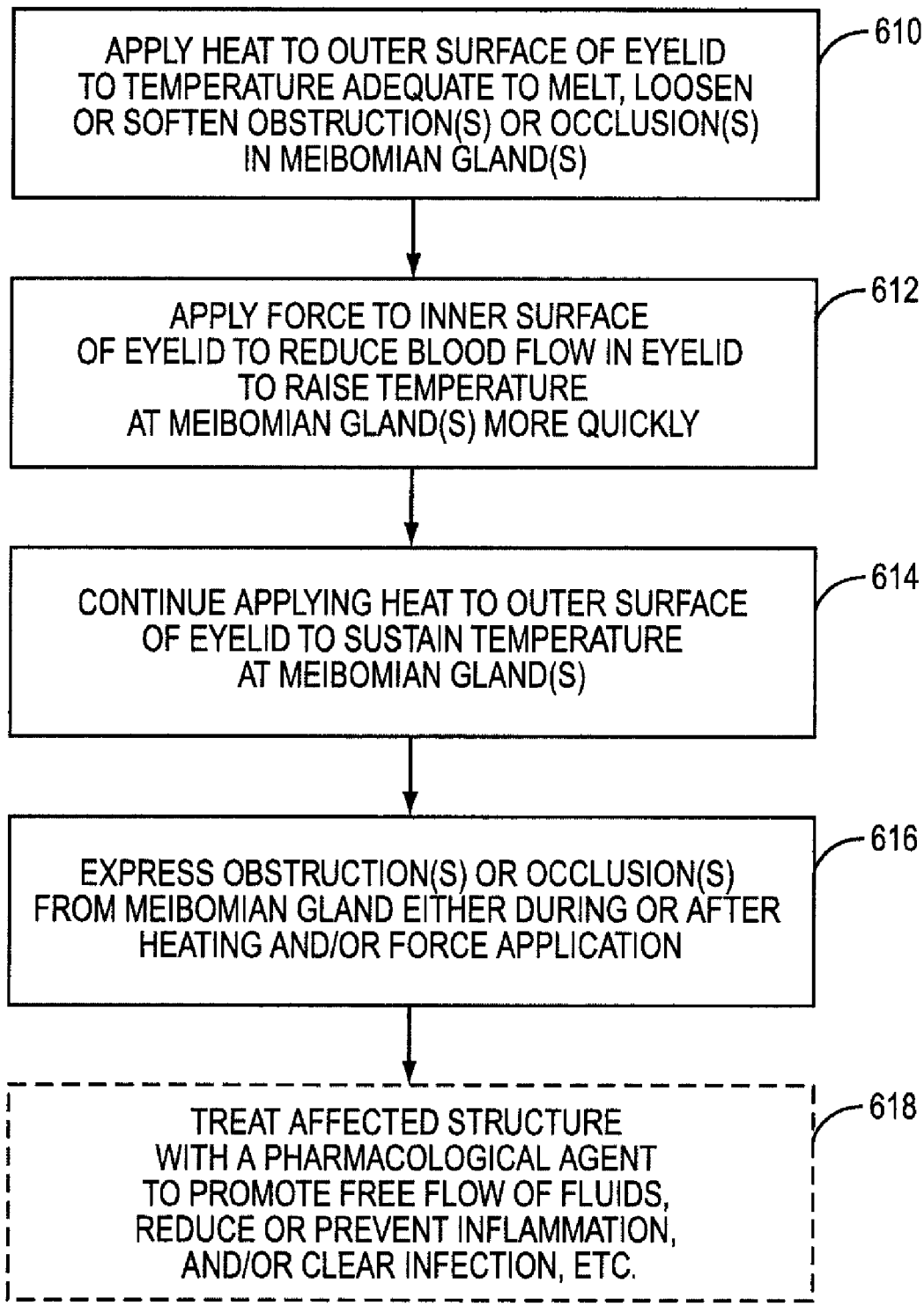
FIG. 42 is a flowchart illustrating an alternate meibomian gland treatment employing applying heat to the outside of a patient's eyelid and force to the inside of the patient's eyelid for treating meibomian glands.

FIG. 42 illustrates an alternative embodiment of the present invention for applying heat and force to a patient's eyelid to treat MGD. In this embodiment, heat is applied to the outside of the eyelid and force is applied to the inside of the eyelid. Heat is applied to the outside of the eyelid to provide conductive heat transfer to the meibomian glands to the desired temperature level (step 610). For example, heat may be applied to raise the temperature at the inside of the eyelid to between 43-47 degrees Celsius. The heat may also be regulated, meaning that a heating means or element is controlled to be within the temperatures and means that are safe for the eyelid and at a sufficient temperature for melting, loosening, or softening an occlusion or obstruction in the meibomian gland.

A force may also be applied to the inside of the eyelid to increase the efficiency of heat transfer. As previously described, the application of force towards the heat source with the patient's eyelid "sandwiched" therebetween provides greater surface contact between the heat source and the eyelid for more efficient conductive heat transfer. Further, the application of force reduces blood flow in the eyelids to reduce convective heat loss through the eyelids and allow the temperature at the meibomian glands to not only rise to higher levels, but do so more quickly and efficiently (step 612).

The heat and/or force may be maintained for a period of time sufficient to raise the temperature at the meibomian glands to a level sufficient to melt, loosen, or soften the obstructions or occlusions (step 614). The force may be maintained after heat is removed, or vice versa depending on the treatment technique desired. Maintaining force after heat is removed may reduce convective heat loss at the meibomian glands and thus keep the temperature level at the meibomian glands to the therapeutic levels for more time than if the force was removed. Maintaining heat without maintaining force may be employed to allow blood flow in the eyelids, such as between successive treatments. For example, it may be desirable to maintain heat to lessen the total amount of treatment time while applying and removing force between treatments. Also, it may not be necessary to apply significant amounts of force, or for the same duration as application of heat, if the obstruction or occlusion is located in close proximity to the lid margin rather than in the deeper portions of the meibomian gland. Thereafter, either during heating and/or the application of force or after either, obstructions or occlusions in the meibomian glands may be expressed so that sebum flow is restored from the glands to establish a sufficient lipid layer (step 616).

The force may be regulated, meaning that a force generating means is controlled to be within the pressure ranges that are safe to be applied to the eyelid and at sufficient pressure to allow the temperature at the meibomian gland to be raised sufficiently. The force may be applied during heating, after heating, or both during and after heating. In either case, the force may assist in expressing occlusions or obstructions when in a loosened, softened, or melted state from the meibomian glands. The force may include vibratory type forces, including those generated mechanically or using fluid type devices or mechanisms. The level of force needed to express obstructions or occlusions in the glands may be greatly reduced when heat is applied to the obstructions or occlusions to place them in a melted, softened, or loosened state.

The application of force can also stimulate the movement of fluids or suspensions of occlusions or obstructions from the glands. The present invention can be used with devices which generally apply a regulated force or milking action to the eyelid to express the fluids or suspensions or to otherwise mechanically stimulate the movement of fluids from the glands. In some instances, a small, gentle, continuous force applied to the eyelid will assist in expression of the fluids and suspensions. Vibration can also be used when applying force simultaneously or immediately after the heating to further assist in the expression.

Any device may be employed to generate heat on the outside of the patient's eyelid, including those described herein. Other devices may be employed, such as the apparatus disclosed in U.S. Patent Application Publication No. 2007/1016254, entitled "Method and apparatus for treating gland dysfunction employing heated medium," and incorporated herein by reference in its entirety. In this application, an apparatus is employed to apply heat to the outside of the patient's eyelid via heated fluid transfer. Further, a gas may be employed as opposed to fluid to apply heat to the patient's eyelid.

Just as discussed above in the flowchart of FIG. 6, where only heat is applied, regulated heat can include controlling heat according to a temperature profile. The temperature profile may be a constant temperature, include ramp-ups, ramp-downs, peaks and valleys. Further, the temperature profile may include heat pulses or be modulated with various characteristics, including the use of pulse width modulation (PWM) techniques. The use of modulated heat may allow the temperature to be raised even higher at the eyelid without damage to the patient's eyelid since the increased temperatures are applied for shorter periods of time. Obstructions or occlusions in the meibomian glands may have melting, loosening, or softening points that are beyond temperatures that may be applied without the use of modulated heat. The temperature needed to melt, loosen, or soften obstructions or occlusions may depend on how keratinized the obstruction or occlusion is. Not all obstructions or occlusions have the same melting, loosening, or softening points. By example only, elevated temperatures between 47 and 55 degrees Celsius may be possible when applying modulated heat, especially if the eyelid has been anesthetized.

The regulated heat can be maintained at a therapeutic temperature for a treatment period. The treatment period can be approximately 1 to 10 minutes for example, since the application of force may reduce the amount of time it takes for the heat source to raise the temperature at the meibomian glands to the desired level. The heat could also be repeatedly applied and maintained for a desired period of time to keep the occlusion or obstruction in a melted, loosened, or softened state. Either during or after such treatment by regulated heat, mechanical expression of lipids and other fluids from the meibomian glands has been found to clear obstructions which have essentially melted or been placed in a suspension state (by virtue of melting materials binding solids together).

Optionally, after expression of occlusions or obstructions is performed (step 616), an optional pharmacological agent may be applied to the meibomian gland to promote the free flow of sebum and/or reduce or prevent inflammation or infections of the eye or eyelids (step 618). The previous discussion in the flowcharts of FIGS. 6 and 8 regarding use of pharmacological agents above is equally applicable for this embodiment and thus will not be repeated here. Those compounds are illustrative examples of appropriate pharmacological agents, but those skilled in the art will appreciate that other pharmacological compounds may be utilized.

Figure 43:
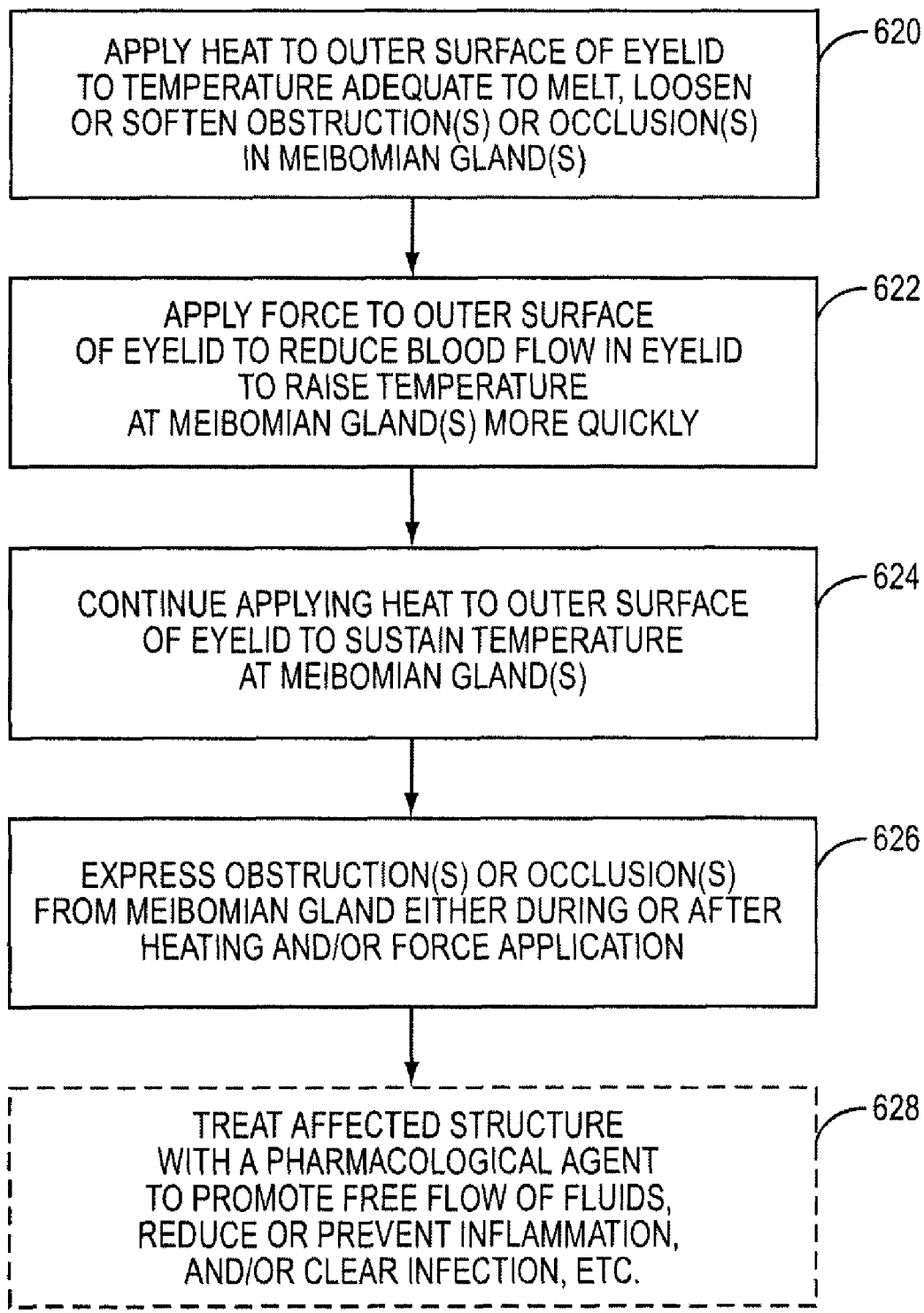
FIG. 43 is a flowchart illustrating an alternate meibomian gland treatment employing applying heat and force to the outside of a patient's eyelid for treating meibomian glands.

FIG. 43 illustrates an alternative embodiment of the present invention for applying heat and force to a patient's eyelid to treat MGD. In this embodiment, heat and force are both applied to the outside of the eyelid. Heat is applied to the outside of the eyelid to provide conductive heat transfer to the meibomian glands to the desired temperature level (step 620). For example, heat may be applied to raise the temperature at the inside of the eyelid between 43-47 degrees Celsius. The heat may also be regulated, meaning that a heating means or element is controlled to be within the temperatures and means that are safe for the eyelid and at a sufficient temperature for melting, loosening, or softening an occlusion or obstruction in the meibomian gland.

A force may also be applied to the outside of the eyelid to increase the efficiency of heat transfer. As previously described, the application of force may provide greater surface contact between the heat source and the eyelid for more efficient conductive heat transfer. Further, the application of force reduces blood flow in the eyelids to reduce convective heat loss through the eyelids and allow the temperature at the meibomian glands to not only rise to higher levels, but do so more quickly and efficiently (step 622).

The heat and/or force may be maintained for a period of time sufficient to raise the temperature at the meibomian glands sufficient to melt, loosen, or soften the obstructions or occlusions (step 624). The force may be maintained after heat is removed, or vice versa depending on the treatment technique desired. Maintaining force after heat is removed may reduce convective heat loss at the meibomian glands and thus keep the temperature level at the meibomian glands to the therapeutic levels for more time than if the force was removed. Maintaining heat without maintaining force may be employed to allow blood flow in the eyelids, such as between successive treatments. For example, it may be desirable to maintain heat to lessen the total amount of treatment time while applying and removing force between treatments. Also, it may not be necessary to apply significant amounts of force, or for the same duration as application of heat, if the obstruction or occlusion is located in close proximity to the lid margin rather than in the deeper portions of the meibomian gland. Thereafter, either during heating and/or the application of force or after either, obstructions or occlusions in the meibomian glands may be expressed so that sebum flow is restored from the glands to establish a sufficient lipid layer (step 626).

The force may be regulated, meaning that a force generating means is controlled to be within the pressure ranges that are safe to be applied to the eyelid and at sufficient pressure to allow the temperature at the meibomian gland to be raised sufficiently. The force may be applied during heating, after heating, or both during and after heating. In either case, the force may assist in expressing occlusions or obstructions when in a loosened, softened, or melted state from the meibomian glands. The force may include vibratory type forces, including those generated mechanically or using fluid type devices or mechanisms. The level of force needed to express obstructions or occlusions in the glands may be greatly reduced when heat is applied to the obstructions or occlusions to place them in a melted, softened, or loosened state.

The application of force can also stimulate the movement of fluids or suspensions of occlusions or obstructions from the glands. The present invention can be used with devices which generally apply a regulated force or milking action to the eyelid to express the fluids or suspensions or to otherwise mechanically stimulate the movement of fluids from the glands. In some instances, a small, gentle, continuous force applied to the eyelid will assist in expression of the fluids and suspensions. Vibration can also be used when applying force simultaneously or immediately after the heating to further assist in the expression.

Any device may be employed to generate heat on the outside of the patient's eyelid, including those described herein. Other devices may be employed, such as the apparatus disclosed in U.S. Patent Application Publication No. 2007/1016254, entitled "Method and apparatus for treating gland dysfunction employing heated medium," and incorporated herein by reference in its entirety. In this application, an apparatus is employed to apply heat to the outside of the patient's eyelid via heated fluid transfer. Further, a gas may be employed as opposed to fluid to apply heat to the patient's eyelid.

Just as discussed above in the flowchart of FIG. 6, where only heat is applied, regulated heat can include controlling heat according to a temperature profile. The temperature profile may be a constant temperature, include ramp-ups, ramp-downs, peaks and valleys. Further, the temperature profile may include heat pulses or be modulated with various characteristics, including the use of pulse width modulation (PWM) techniques. The use of modulated heat may allow the temperature to be raised even higher at the eyelid without damage to the patient's eyelid since the increased temperatures are applied for shorter periods of time. Obstructions or occlusions in the meibomian glands may have melting, loosening, or softening points that are beyond temperatures that may be applied without the use of modulated heat. The temperature needed to melt, loosen, or soften obstructions or occlusions may depend on how keratinized the obstruction or occlusion is. Not all obstructions or occlusions have the same melting, loosening, or softening points. By example only, elevated temperatures between 47 and 55 degrees Celsius may be possible when applying modulated heat, especially if the eyelid has been anesthetized.

The regulated heat can be maintained at a therapeutic temperature for a treatment period. The treatment period can be approximately 1 to 10 minutes for example, since the application of force may reduce the amount of time it takes for the heat source to raise the temperature at the meibomian glands to the desired level. The heat could also be repeatedly applied and maintained for a desired period of time to keep the occlusion or obstruction in a melted, loosened, or softened state. Either during or after such treatment by regulated heat, mechanical expression of lipids and other fluids from the meibomian glands has been found to clear obstructions which have essentially melted or been placed in a suspension state (by virtue of melting materials binding solids together).

Optionally, after expression of occlusions or obstructions is performed (step 626), an optional pharmacological agent may be applied to the meibomian gland to promote the free flow of sebum and/or reduce or prevent inflammation or infections of the eye or eyelids (step 628). The previous discussion in the flowcharts of FIGS. 6 and 8 regarding use of pharmacological agents above is equally applicable for this embodiment and thus will not be repeated here. Those compounds are illustrative examples of appropriate pharmacological agents, but those skilled in the art will appreciate that other pharmacological compounds may be utilized.

Figure 44:
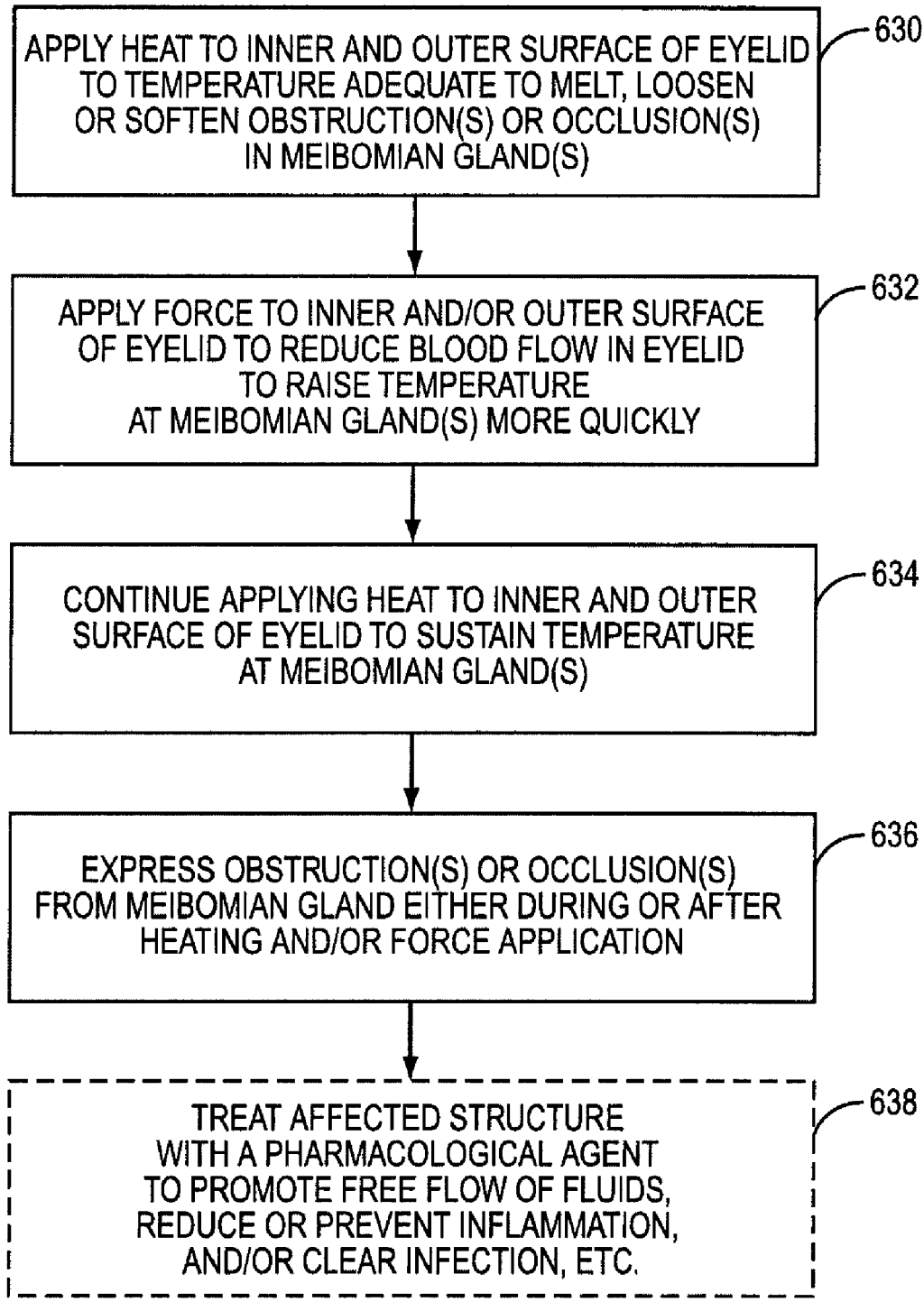
FIG. 44 is a flowchart illustrating an alternate meibomian gland treatment employing applying heat to both the inside and the outside of a patient's eyelid for treating meibomian glands.

FIG. 44 illustrates an alternative embodiment of the present invention for applying heat and force to a patient's eyelid to treat MGD. In this embodiment, heat is applied to both the inner and external surface of the patient's eyelid. Force may also be applied to the patient's eyelid. Heat is applied to the both the inside and outside of the eyelid to provide even more efficient conductive heat transfer to the meibomian glands to the desired temperature level (step 630). For example, heat may be applied to raise the temperature at the inside of the eyelid between 43-47 degrees Celsius. The heat may also be regulated, meaning that a heating means or element is controlled to be within the temperatures and means that are safe for the eyelid and at a sufficient temperature for melting, loosening, or softening an occlusion or obstruction in the meibomian gland.

A force may also be applied to the eyelid to increase the efficiency of heat transfer. As previously described, the application of force may provide greater surface contact between the heat source and the eyelid for more efficient conductive heat transfer. Further, the application of force reduces blood flow in the eyelids to reduce convective heat loss through the eyelids and allow the temperature at the meibomian glands to not only rise to higher levels, but do so more quickly and efficiently (step 632).

The heat and/or force may be maintained for a period of time sufficient to raise the temperature at the meibomian glands sufficient to melt, loosen, or soften the obstructions or occlusions (step 634). The force may be maintained after heat is removed, or vice versa depending on the treatment technique desired. Maintaining force after heat is removed may reduce convective heat loss at the meibomian glands and thus keep the temperature level at the meibomian glands to the therapeutic levels for more time than if the force was removed. Maintaining heat without maintaining force may be employed to allow blood flow in the eyelids, such as between successive treatments. For example, it may be desirable to maintain heat to lessen the total amount of treatment time while applying and removing force between treatments. Also, it may not be necessary to apply significant amounts of force, or for the same duration as application of heat, if the obstruction or occlusion is located in close proximity to the lid margin rather than in the deeper portions of the meibomian gland. Thereafter, either during heating and/or the application of force or after either, obstructions or occlusions in the meibomian glands may be expressed so that sebum flow is restored from the glands to establish a sufficient lipid layer (step 636).

The force may be regulated, meaning that a force generating means is controlled to be within the pressure ranges that are safe to be applied to the eyelid and at sufficient pressure to allow the temperature at the meibomian gland to be raised sufficiently. The force may be applied during heating, after heating, or both during and after heating. In either case, the force may assist in expressing occlusions or obstructions when in a loosened, softened, or melted state from the meibomian glands. The force may include vibratory type forces, including mechanical or those using fluid type devices or mechanisms. The level of force needed to express obstructions or occlusions in the glands may be greatly reduced when heat is applied to the obstructions or occlusions to place them in a melted, softened, or loosened state.

The application of force can also stimulate the movement of fluids or suspensions of occlusions or obstructions from the glands. The present invention can be used with devices which generally apply a regulated force or milking action to the eyelid to express the fluids or suspensions or to otherwise mechanically stimulate the movement of fluids from the glands. In some instances, a small, gentle, continuous force applied to the eyelid will assist in expression of the fluids and suspensions. Vibration can also be used when applying force simultaneously or immediately after the heating to further assist in the expression.

Any device may be employed to generate heat on the inside and outside of the patient's eyelid, including those described herein. Just as discussed above in the flowchart of FIG. 6, where only heat is applied, regulated heat can include controlling heat according to a temperature profile. The temperature profile may be a constant temperature, include ramp-ups, ramp-downs, peaks and valleys. Further, the temperature profile may include heat pulses or be modulated with various characteristics, including the use of pulse width modulation (PWM) techniques. The use of modulated heat may allow the temperature to be raised even higher at the eyelid without damage to the patient's eyelid since the increased temperatures are applied for shorter periods of time. Obstructions or occlusions in the meibomian glands may have melting, loosening, or softening points that are beyond temperatures that may be applied without the use of modulated heat. The temperature needed to melt, loosen, or soften obstructions or occlusions may depend on how keratinized the obstruction or occlusion is. Not all obstructions or occlusions have the same melting, loosening, or softening points. By example only, elevated temperatures between 47 and 55 degrees Celsius may be possible when applying modulated heat, especially if the eyelid has been anesthetized.

The regulated heat can be maintained at a therapeutic temperature for a treatment period. The treatment period can be approximately 1 to 10 minutes for example, since the application of force may reduce the amount of time it takes for the heat source to raise the temperature at the meibomian glands to the desired level. The heat could also be repeatedly applied and maintained for a desired period of time to keep the occlusion or obstruction in a melted, loosened, or softened state. Either during or after such treatment by regulated heat, mechanical expression of lipids and other fluids from the meibomian glands has been found to clear obstructions which have essentially melted or been placed in a suspension state (by virtue of melting materials binding solids together).

Optionally, after expression of occlusions or obstructions is performed (step 636), an optional pharmacological agent may be applied to the meibomian gland to promote the free flow of sebum and/or reduce or prevent inflammation or infections of the eye or eyelids (step 638). The previous discussion in the flowcharts of FIGS. 6 and 8 regarding use of pharmacological agents above is equally applicable for this embodiment and thus will not be repeated here. Those compounds are illustrative examples of appropriate pharmacological agents, but those skilled in the art will appreciate that other pharmacological compounds may be utilized.

Those skilled in the art will recognize improvements and modifications to the preferred embodiments of the present invention. Heat as used in this application can mean the application of thermal energy. Heat may be applied to the patient's eyelid, related structure, or surrounding tissue using any type of thermal energy. Force may be applied to the patent's eyelid to apply pressure to the patient's eyelid, related structure, and/or surrounding tissue using any type of force or force generating means or device. All such improvements and modifications are considered within the scope of the concepts disclosed herein and the claims that follow.

What is claimed is:

1. A system for treating meibomian gland dysfunction, comprising:
   a lid warmer containing a heating element, wherein the lid warmer is adapted to be positioned behind a patient's eyelid on the external surface of the sclera of a patient's eye, wherein the lid warmer applies heat to an inner surface of a patient's eyelid to a temperature level to melt, loosen, or soften an obstruction located within a meibomian gland channel of a meibomian gland;
   a force application device positioned on the inner surface of the patient's eyelid, wherein the force application device applies a compressive force to the inner surface of a patient's eyelid; and
   a controller communicatively coupled to the lid warmer and the force application device,
   wherein the controller is further adapted to:
      send a signal to the lid warmer to apply heat to the inner surface of a patient's eyelid to a temperature level to melt, loosen, or soften an obstruction located within the meibomian gland channel of a meibomian gland;
      control the force application device to generate a compressive force on the inner surface of the patient's eyelid to express the obstruction located within the meibomian gland channel and from within the meibomian gland channel through a meibomian gland orifice of the meibomian gland; and
      maintain the signal to the lid warmer to maintain the heat on the inner surface of the patient's eyelid for a period of time.

2. The system of claim 1, wherein the controller further comprises a lid warmer controller that is adapted to control the heating element to control the amount of heat generated by the heating element.

3. The system of claim 2, wherein the lid warmer controller is a pulse width modulated controller.

4. The system of claim 1, wherein the controller is further adapted to check a fuse on the lid warmer to determine if the lid warmer has been previously used before sending the signal to the lid warmer to apply heat to the inner surface of a patient's eyelid to a temperature level to melt, loosen, or soften an obstruction in a meibomian gland.

5. The system of claim 1, wherein the controller further comprises a therapy timer, wherein the therapy timer controls the amount of time the controller sends the signal to the lid warmer to apply heat to the inner surface of a patient's eyelid.

6. The system of claim 5, wherein the controller further comprises a display having a therapy timer display, wherein the controller is adapted to display the amount of time in the therapy timer on the therapy timer display.

7. The system of claim 1, wherein the lid warmer further comprises a temperature feedback device adapted to measure the temperature level at the lid warmer, wherein the controller is further adapted to monitor the temperature level at the lid warmer using the temperature feedback device.

8. The system of claim 7, wherein the temperature feedback device is comprised of at least one thermistor.

9. The system of claim 7, wherein the controller regulates the signal sent to the lid warmer to regulate the heat generated by the heating element based on the temperature level at the lid warmer from the temperature feedback device.

10. The system of claim 9, wherein the controller is further adapted to generate an error and/or disable the signal to the lid warmer to discontinue the generation of heat by the heating element if the temperature level at the lid warmer exceeds a threshold temperature level.

11. The system of claim 9, wherein the controller is further adapted to generate an error and/or not send the signal to the lid warmer to have the heating element generate heat if the temperature level at the lid warmer does not initially meet or exceed body temperature.

12. The system of claim 7, wherein the controller further comprises a data log, and wherein the controller is further adapted to store information relating to the temperature levels measured by the temperature feedback device.

13. The system of claim 1, wherein the controller further comprises a display comprising a temperature level display that displays the temperature level at the lid warmer.

14. The system of claim 1, wherein the controller further comprises a pressure controller that is adapted to control the force application device to control the amount of compressive force generated by the force application device.

15. The system of claim 1, wherein the controller further comprises a force lever, wherein the pressure controller is further adapted to control the compressive force generated by the force application device in response to engagement of the force lever.

16. The system of claim 1, wherein the controller further comprises a pressure feedback device adapted to measure the compressive force generated by the force application device, wherein the controller is further adapted to monitor the pressure level of the compressive force at the inner surface of the patient's eyelid using the pressure feedback device.

17. The system of claim 16, wherein the controller is further adapted to generate an error and/or disable a compressive force generated by the force application device to discontinue a compressive force generated at the inner surface of the patient's eyelid if the pressure of the compressive force generated by the force application device exceeds a threshold pressure level.

18. The system of claim 16, wherein the controller further comprises a data log, and wherein the controller is further adapted to store information relating to the pressure levels of the compressive force measured by the pressure feedback device.

19. The system of claim 1, wherein the controller further comprises a display comprising a pressure level display that displays the pressure of the compressive force applied to the inner surface of the patient's eyelid.

20. The system of claim 1, wherein the controller further comprises an energy source to power the controller, and wherein the controller is further adapted to generate an error if the energy source cannot generate a threshold energy amount.

21. The system of claim 1, wherein the controller is further adapted to assist in the expression of the obstruction from the meibomian gland channel of the meibomian gland by controlling the compressive force generated by the force application device.

22. The system of claim 1, wherein the controller is further adapted to maintain the compressive force generated by the force application device while the controller is sending a signal to the lid warmer to generate heat.

23. The system of claim 1, wherein the controller is further adapted to maintain the compressive force generated by the force application device while the controller is sending a signal to the lid warmer to generate heat to reduce blood flow in the patient's eyelid to reduce convective heat loss from the heat applied to the inner surface of the patient's eyelid.

24. The system of claim 1, wherein the controller is further adapted to generate a signal to the lid warmer to generate the heat at a temperature level between approximately 35 and 55 degrees Celsius.

* * * * *

UNITED STATES PATENT AND TRADEMARK OFFICE
CERTIFICATE OF CORRECTION

PATENT NO.        : 8,128,673 B2
APPLICATION NO.   : 12/015675
DATED             : March 6, 2012
INVENTOR(S)       : Donald R. Korb et al.

It is certified that error appears in the above-identified patent and that said Letters Patent is hereby corrected as shown below:

Claim 1, at column 50, line 10, change "wanner" to --warmer--.

Claim 4, at column 50, line 30, change "wanner" to --warmer--.

Signed and Sealed this
First Day of May, 2012

David J. Kappos
*Director of the United States Patent and Trademark Office*